US012590150B2

(12) United States Patent
Ren et al.

(10) Patent No.: US 12,590,150 B2
(45) Date of Patent: Mar. 31, 2026

(54) ANTIBODY AGAINST NECTIN-4 AND APPLICATION THEREOF

(71) Applicant: MABWELL (SHANGHAI) BIOSCIENCE CO., LTD., Shanghai (CN)

(72) Inventors: Hongyuan Ren, Shanghai (CN); Jian Zhu, Shanghai (CN); Jian Lin, Shanghai (CN); Lichun Wang, Shanghai (CN); Xiaohong Xu, Shanghai (CN); Xiaofang Deng, Shanghai (CN); Jianjun Bi, Shanghai (CN); Jin Wang, Shanghai (CN); Jian Wu, Shanghai (CN)

(73) Assignee: MABWELL (SHANGHAI) BIOSCIENCE CO. LTD., Shanghai (CN)

( * ) Notice: Subject to any disclaimer, the term of this patent is extended or adjusted under 35 U.S.C. 154(b) by 771 days.

(21) Appl. No.: 17/996,403

(22) PCT Filed: Apr. 21, 2021

(86) PCT No.: PCT/CN2021/088661
§ 371 (c)(1),
(2) Date: Nov. 25, 2022

(87) PCT Pub. No.: WO2021/213434
PCT Pub. Date: Oct. 28, 2021

(65) Prior Publication Data
US 2023/0265183 A1 Aug. 24, 2023

(30) Foreign Application Priority Data
Apr. 21, 2020 (CN) .......................... 202010320420.3

(51) Int. Cl.
| | |
|---|---|
| *C07K 16/28* | (2006.01) |
| *A61K 31/704* | (2006.01) |
| *A61K 39/00* | (2006.01) |
| *A61K 39/395* | (2006.01) |
| *A61K 45/06* | (2006.01) |
| *A61K 47/68* | (2017.01) |
| *A61P 15/00* | (2006.01) |
| *A61P 35/00* | (2006.01) |
| *G01N 33/574* | (2006.01) |

(52) U.S. Cl.
CPC .... *C07K 16/2803* (2013.01); *A61K 47/68031* (2023.08); *A61K 47/6817* (2017.08); *A61K 47/6849* (2017.08); *A61K 47/6855* (2017.08); *A61P 15/00* (2018.01); *A61P 35/00* (2018.01); *C07K 16/28* (2013.01); *G01N 33/57492* (2013.01); *A61K 2039/505* (2013.01); *C07K 2317/24* (2013.01); *C07K 2317/33* (2013.01); *C07K 2317/52* (2013.01); *C07K 2317/565* (2013.01); *C07K 2317/73* (2013.01); *C07K 2317/92* (2013.01); *G01N 2333/705* (2013.01)

(58) Field of Classification Search
None
See application file for complete search history.

(56) References Cited

U.S. PATENT DOCUMENTS

2011/0223176 A1* 9/2011 Barlow .............. C07K 16/2803
536/23.53

FOREIGN PATENT DOCUMENTS

| | | | |
|---|---|---|---|
| CN | 109810039 A | 5/2019 | |
| WO | WO 2005/111076 A1 | 11/2005 | |
| WO | WO-2017042210 A1 * | 3/2017 | .............. A61P 35/04 |
| WO | 2018/158398 A1 | 9/2018 | |
| WO | 2018/226578 A1 | 12/2018 | |
| WO | WO-2019215728 A1 * | 11/2019 | .............. A61K 45/06 |

OTHER PUBLICATIONS

Boylan et al. Oncotarget. 8(6): 9717-9738; Published: Dec. 25, 2016 (Year: 2016).*
Fabre-Lafay et al. BMC Cancer. 7:73; Published: May 2, 2007 (Year: 2007).*
Challita-Eid et al. Cancer Research. 76(10): 3003-3013; Published: May 12, 2016 (Year: 2016).*
Noyce et al. Trends in Microbiology. 20(9): 429-439; Published: Sep. 2012 (Year: 2012).*
Pitot et al. Cancer. 73(3): 962-970; Published: Aug. 1, 1993 (Year: 1993).*
Hanahan et al. Cell. 144(5): 646-674; Published: Mar. 4, 2011 (Year: 2011).*
Lebozec et al. New Biotechnology. 44: 31-40; Published: Sep. 25, 2018 (Year: 2018).*
McGregor, Bradley A. et al., "Enfortumab Vedotin, a fully human monoclonal antibody against Nectin 4 conjugated to monomethyl auristatin E for metastatic orothelial Carcinoma", Expert Opinion on Investigational Drugs, Published online: Sep. 17, 2019 (Year: 2019) DOI: 10.1080/13543784.2019.1667332 (7 pages).
M-Rabet et al., "Nectin-4: a new prognostic biomarker for efficient therapeutic targeting of primary and metastatic triple-negative breast cancer", Annals of Oncology, Published Dec. 20, 2016) (Year: 2016) (37 pages).

* cited by examiner

*Primary Examiner* — Juliet C Switzer
*Assistant Examiner* — Katherine Ann Holtzman
(74) *Attorney, Agent, or Firm* — Lewis Roca Rothgerber Christie LLP

(57) ABSTRACT

Provided is an antibody molecule that binds to human Nectin-4 or a fragment thereof. The antibody is obtained by means of hybridoma screening and humanization techniques, and is used for the prevention or treatment of a cancer, and may be used as a clinical lead drug molecule.

31 Claims, 13 Drawing Sheets
Specification includes a Sequence Listing.

1A

FITC (BL1-H)

1B

APC (RL1-H)

FIG. 2A
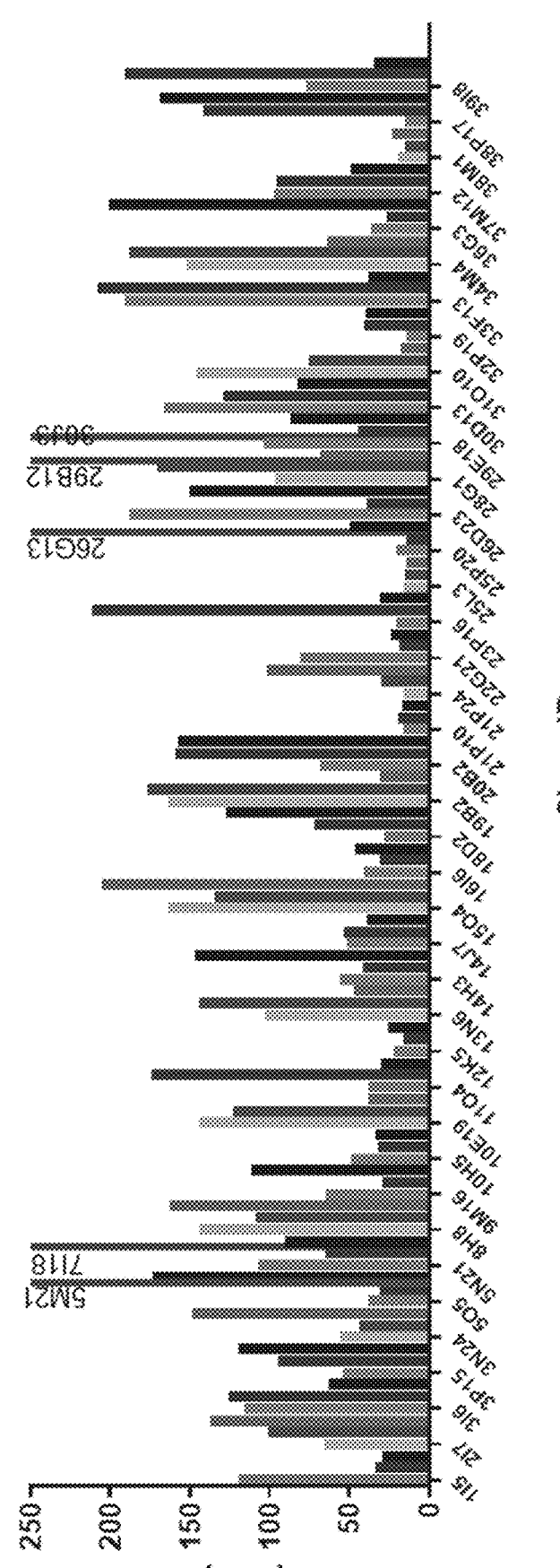
In Fig. 2, bars of different gray tones represent different clones.

In Fig. 2, bars of different gray tones represent different clones.

In Fig. 2, bars of different gray tones represent different clones.

3A

3B

4A

4B

1. Enfortumab
2. 42D20 xiIgG
3. 42D20 hz00
4. 42D20 hz01
5. 42D20 hz03
6. 42D20 hz10
7. 42D20 hz11
8. 42D20 hz13
9. 42D20 hz20
10. 42D20 hz21
11. 42D20 hz23

1. Enfortumab-E
2. 42D20 hz10-E
3. 42D20 hz43-E
4. 42D20 hz44-E
5. 42D20 hz63-E
6. 42D20 hz64-E
7. 20M12 xiIgG-E
8. 42D20 hz01-E
9. 42D20 hz11-E
10. Isotyep control

5A

5B

6A

7A

7B

8A

8B

SEQUENCE LISTING

<160> NUMBER OF SEQ ID NOS: 97

<210> SEQ ID NO 1
<211> LENGTH: 447
<212> TYPE: PRT
<213> ORGANISM: artificial sequence
<220> FEATURE:
<223> OTHER INFORMATION: Enfortumab, HC

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Arg Ala Tyr Tyr Tyr Gly Met Asp Val Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser

-continued

```
                180              185                190
Leu Gly Thr Gln Thr Tyr Ile Cys Asn Val Asn His Lys Pro Ser Asn
            195              200              205

Thr Lys Val Asp Lys Arg Val Glu Pro Lys Ser Cys Asp Lys Thr His
        210              215              220

Thr Cys Pro Pro Cys Pro Ala Pro Glu Leu Leu Gly Gly Pro Ser Val
225              230              235              240

Phe Leu Phe Pro Pro Lys Pro Lys Asp Thr Leu Met Ile Ser Arg Thr
                245              250              255

Pro Glu Val Thr Cys Val Val Val Asp Val Ser His Glu Asp Pro Glu
            260              265              270

Val Lys Phe Asn Trp Tyr Val Asp Gly Val Glu Val His Asn Ala Lys
        275              280              285

Thr Lys Pro Arg Glu Glu Gln Tyr Asn Ser Thr Tyr Arg Val Val Ser
        290              295              300

Val Leu Thr Val Leu His Gln Asp Trp Leu Asn Gly Lys Glu Tyr Lys
305              310              315              320

Cys Lys Val Ser Asn Lys Ala Leu Pro Ala Pro Ile Glu Lys Thr Ile
                325              330              335

Ser Lys Ala Lys Gly Gln Pro Arg Glu Pro Gln Val Tyr Thr Leu Pro
                340              345              350

Pro Ser Arg Glu Glu Met Thr Lys Asn Gln Val Ser Leu Thr Cys Leu
                355              360              365

Val Lys Gly Phe Tyr Pro Ser Asp Ile Ala Val Glu Trp Glu Ser Asn
        370              375              380

Gly Gln Pro Glu Asn Asn Tyr Lys Thr Thr Pro Pro Val Leu Asp Ser
385              390              395              400

Asp Gly Ser Phe Phe Leu Tyr Ser Lys Leu Thr Val Asp Lys Ser Arg
                405              410              415

Trp Gln Gln Gly Asn Val Phe Ser Cys Ser Val Met His Glu Ala Leu
            420              425              430

His Asn His Tyr Thr Gln Lys Ser Leu Ser Leu Ser Pro Gly Lys
            435              440              445
```

```
<210> SEQ ID NO 2
<211> LENGTH: 214
<212> TYPE: PRT
<213> ORGANISM: artificial sequence
<220> FEATURE:
<223> OTHER INFORMATION: Enfortumab, LC

<400> SEQUENCE: 2

Asp Ile Gln Met Thr Gln Ser Pro Ser Ser Val Ser Ala Ser Val Gly
1               5               10              15

Asp Arg Val Thr Ile Thr Cys Arg Ala Ser Gln Gly Ile Ser Gly Trp
            20              25              30

Leu Ala Trp Tyr Gln Gln Lys Pro Gly Lys Ala Pro Lys Phe Leu Ile
        35              40              45

Tyr Ala Ala Ser Thr Leu Gln Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Ala Asn Ser Phe Pro Pro
                85              90              95

Thr Phe Gly Gly Gly Thr Lys Val Glu Ile Lys Arg Thr Val Ala Ala
```

-continued

```
               100                 105                 110

Pro Ser Val Phe Ile Phe Pro Pro Ser Asp Glu Gln Leu Lys Ser Gly
           115                 120                 125

Thr Ala Ser Val Val Cys Leu Leu Asn Asn Phe Tyr Pro Arg Glu Ala
       130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
               165                 170                 175

Ser Thr Leu Thr Leu Ser Lys Ala Asp Tyr Glu Lys His Lys Val Tyr
           180                 185                 190

Ala Cys Glu Val Thr His Gln Gly Leu Ser Ser Pro Val Thr Lys Ser
       195                 200                 205

Phe Asn Arg Gly Glu Cys
       210

<210> SEQ ID NO 3
<211> LENGTH: 318
<212> TYPE: PRT
<213> ORGANISM: Homo sapiens

<400> SEQUENCE: 3

Gly Glu Leu Glu Thr Ser Asp Val Val Thr Val Val Leu Gly Gln Asp
1                 5                 10                 15

Ala Lys Leu Pro Cys Phe Tyr Arg Gly Asp Ser Gly Glu Gln Val Gly
           20                 25                 30

Gln Val Ala Trp Ala Arg Val Asp Ala Gly Glu Gly Ala Gln Glu Leu
       35                 40                 45

Ala Leu Leu His Ser Lys Tyr Gly Leu His Val Ser Pro Ala Tyr Glu
   50                 55                 60

Gly Arg Val Glu Gln Pro Pro Pro Arg Asn Pro Leu Asp Gly Ser
65                 70                 75                 80

Val Leu Leu Arg Asn Ala Val Gln Ala Asp Glu Gly Glu Tyr Glu Cys
               85                 90                 95

Arg Val Ser Thr Phe Pro Ala Gly Ser Phe Gln Ala Arg Leu Arg Leu
           100                 105                 110

Arg Val Leu Val Pro Pro Leu Pro Ser Leu Asn Pro Gly Pro Ala Leu
           115                 120                 125

Glu Glu Gly Gln Gly Leu Thr Leu Ala Ala Ser Cys Thr Ala Glu Gly
       130                 135                 140

Ser Pro Ala Pro Ser Val Thr Trp Asp Thr Glu Val Lys Gly Thr Thr
145                 150                 155                 160

Ser Ser Arg Ser Phe Lys His Ser Arg Ser Ala Ala Val Thr Ser Glu
               165                 170                 175

Phe His Leu Val Pro Ser Arg Ser Met Asn Gly Gln Pro Leu Thr Cys
           180                 185                 190

Val Val Ser His Pro Gly Leu Leu Gln Asp Gln Arg Ile Thr His Ile
           195                 200                 205

Leu His Val Ser Phe Leu Ala Glu Ala Ser Val Arg Gly Leu Glu Asp
       210                 215                 220

Gln Asn Leu Trp His Ile Gly Arg Glu Gly Ala Met Leu Lys Cys Leu
225                 230                 235                 240

Ser Glu Gly Gln Pro Pro Pro Ser Tyr Asn Trp Thr Arg Leu Asp Gly
               245                 250                 255
```

-continued

```
Pro Leu Pro Ser Gly Val Arg Val Asp Gly Asp Thr Leu Gly Phe Pro
            260             265             270

Pro Leu Thr Thr Glu His Ser Gly Ile Tyr Val Cys His Val Ser Asn
            275             280             285

Glu Phe Ser Ser Arg Asp Ser Gln Val Thr Val Asp Val Leu Asp Pro
            290             295             300

Gln Glu Asp Ser Gly Lys Gln Val Asp Leu Val Ser Ala Ser
305             310             315

<210> SEQ ID NO 4
<211> LENGTH: 330
<212> TYPE: PRT
<213> ORGANISM: Homo sapiens

<400> SEQUENCE: 4

Ala Ser Thr Lys Gly Pro Ser Val Phe Pro Leu Ala Pro Ser Ser Lys
1               5               10              15

Ser Thr Ser Gly Gly Thr Ala Ala Leu Gly Cys Leu Val Leu Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Gln Thr
65              70              75              80

Tyr Ile Cys Asn Val Asn His Lys Pro Ser Asn Thr Lys Val Asp Lys
                85              90              95

Arg Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
            130             135             140

Val Val Val Asp Val Ser His Glu Asp Pro Glu Val Leu Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Glu Glu
225             230             235             240

Met Thr Lys Asn Gln Val Ser Leu Thr Cys Leu Val Leu Gly Phe Tyr
                245             250             255

Pro Ser Asp Ile Ala Val Glu Trp Glu Ser Asn Gly Gln Pro Glu Asn
                260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
            290             295             300

Val Phe Ser Cys Ser Val Met His Glu Ala Leu His Asn His Tyr Thr
305             310             315             320
```

```
Gln Lys Ser Leu Ser Leu Ser Pro Gly Lys
                325                 330

<210> SEQ ID NO 5
<211> LENGTH: 107
<212> TYPE: PRT
<213> ORGANISM: Homo sapiens

<400> SEQUENCE: 5

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 6
<211> LENGTH: 510
<212> TYPE: PRT
<213> ORGANISM: Cyno

<400> SEQUENCE: 6

Met Pro Leu Ser Leu Gly Ala Glu Met Trp Gly Pro Glu Ala Trp Leu
1               5                   10                  15

Leu Leu Leu Leu Leu Leu Ala Ser Phe Thr Gly Arg Cys Pro Ala Gly
                20                  25                  30

Glu Leu Glu Thr Ser Asp Val Val Thr Val Val Leu Gly Gln Asp Ala
            35                  40                  45

Lys Leu Pro Cys Phe Tyr Arg Gly Asp Ser Gly Glu Gln Val Gly Gln
        50                  55                  60

Val Ala Trp Ala Arg Ala Asp Ala Gly Glu Gly Ala Gln Glu Leu Ala
65                  70                  75                  80

Leu Leu His Ser Lys Tyr Gly Leu His Val Ser Pro Ala Tyr Glu Gly
                85                  90                  95

Arg Val Glu Gln Pro Pro Pro Arg Asn Pro Leu Asp Gly Ser Val
                100                 105                 110

Leu Leu Arg Asn Ala Val Gln Ala Asp Glu Gly Glu Tyr Glu Cys Arg
            115                 120                 125

Val Ser Thr Phe Pro Ala Gly Ser Phe Gln Ala Arg Leu Arg Leu Arg
        130                 135                 140

Val Leu Val Pro Pro Leu Pro Ser Leu Asn Pro Gly Pro Ala Leu Glu
145                 150                 155                 160

Glu Gly Gln Gly Leu Thr Leu Ala Ala Ser Cys Thr Ala Glu Gly Ser
                165                 170                 175

Pro Ala Pro Ser Val Thr Trp Asp Thr Glu Val Lys Gly Thr Thr Ser
                180                 185                 190

Ser Arg Ser Phe Lys His Ser Arg Ser Ala Ala Val Thr Ser Glu Phe
            195                 200                 205
```

-continued

```
His Leu Val Pro Ser Arg Ser Met Asn Gly Gln Pro Leu Thr Cys Val
    210                 215                 220

Val Ser His Pro Gly Leu Leu Gln Asp Gln Arg Ile Thr His Ile Leu
225                 230                 235                 240

His Val Ser Phe Leu Ala Glu Ala Ser Val Arg Gly Leu Glu Asp Gln
                245                 250                 255

Asn Leu Trp His Val Gly Arg Glu Gly Ala Met Leu Lys Cys Leu Ser
                260                 265                 270

Glu Gly Gln Pro Pro Pro Ser Tyr Asn Trp Thr Arg Leu Asp Gly Pro
                275                 280                 285

Leu Pro Ser Gly Val Arg Val Asp Gly Asp Thr Leu Gly Phe Pro Pro
    290                 295                 300

Leu Thr Thr Glu His Ser Gly Ile Tyr Val Cys His Val Ser Asn Glu
305                 310                 315                 320

Phe Ser Ser Arg Asp Ser Gln Val Thr Val Asp Val Leu Asp Pro Gln
                325                 330                 335

Glu Asp Ser Gly Lys Gln Val Asp Leu Val Ser Ala Ser Val Val Val
                340                 345                 350

Val Gly Val Ile Ala Ala Leu Leu Phe Cys Leu Leu Val Val Val Val
                355                 360                 365

Val Leu Met Ser Arg Tyr His Arg Arg Lys Ala Gln Gln Met Thr Gln
    370                 375                 380

Lys Tyr Glu Glu Glu Leu Thr Leu Thr Arg Glu Asn Ser Ile Arg Arg
385                 390                 395                 400

Leu His Ser His His Thr Asp Pro Arg Ser Gln Pro Glu Glu Ser Val
                405                 410                 415

Gly Leu Arg Ala Glu Gly His Pro Asp Ser Leu Lys Asp Asn Ser Ser
                420                 425                 430

Cys Ser Val Met Ser Glu Glu Pro Glu Gly Arg Ser Tyr Ser Thr Leu
                435                 440                 445

Thr Thr Val Arg Glu Ile Glu Thr Gln Thr Glu Leu Leu Ser Pro Gly
    450                 455                 460

Ser Gly Arg Thr Glu Glu Glu Glu Asp Gln Asp Glu Gly Ile Lys Gln
465                 470                 475                 480

Ala Met Asn His Phe Val Gln Glu Asn Gly Thr Leu Arg Ala Lys Pro
                485                 490                 495

Thr Gly Asn Gly Ile Tyr Ile Asn Gly Arg Gly His Leu Val
                500                 505                 510

<210> SEQ ID NO 7
<211> LENGTH: 116
<212> TYPE: PRT
<213> ORGANISM: artificial sequence
<220> FEATURE:
<223> OTHER INFORMATION: VH

<400> SEQUENCE: 7

Gln Val Gln Leu Gln Gln Ser Gly Pro Glu Leu Val Lys Pro Gly Ala
1                   5                   10                  15

Ser Val Arg Ile Thr Cys Lys Ala Ser Gly Tyr Thr Phe Thr Thr Tyr
                20                  25                  30

Tyr Ile His Trp Val Lys Gln Arg Pro Gly Gln Gly Leu Glu Trp Ile
        35                  40                  45

Gly Trp Ile Tyr Pro Gly Asn Val Asn Thr Lys Tyr Asn Glu Lys Phe
    50                  55                  60
```

Lys Gly Lys Ala Thr Leu Thr Ala Asp Lys Ser Ser Ser Thr Ala Tyr
65              70              75              80

Met Gln Leu Ser Ser Leu Thr Ser Glu Asp Ser Ala Val Tyr Phe Cys
                85              90              95

Ala Arg Gly Leu Tyr Tyr Phe Asp Tyr Trp Gly Gln Gly Thr Thr Leu
            100             105             110

Thr Val Ser Ser
        115

<210> SEQ ID NO 8
<211> LENGTH: 107
<212> TYPE: PRT
<213> ORGANISM: artificial sequence
<220> FEATURE:
<223> OTHER INFORMATION: VL

<400> SEQUENCE: 8

Ser Ile Val Met Thr Gln Thr Pro Lys Phe Leu Leu Val Ser Ala Gly
1               5               10              15

Asp Arg Leu Thr Ile Thr Cys Lys Ala Ser Gln Ser Val Ser Asn Asp
            20              25              30

Val Ala Trp Tyr Gln Gln Lys Pro Gly Gln Ser Pro Lys Leu Leu Ile
        35              40              45

Tyr Tyr Ala Ser Asn Arg Tyr Thr Gly Val Pro Asp Arg Phe Thr Gly
    50              55              60

Ser Gly Tyr Gly Thr Asp Phe Thr Phe Thr Ile Ser Thr Val Gln Ala
65              70              75              80

Glu Asp Leu Ala Val Tyr Phe Cys Gln Gln Asp Tyr Ser Ser Pro Tyr
                85              90              95

Thr Phe Gly Gly Gly Thr Lys Leu Glu Ile Lys
            100             105

<210> SEQ ID NO 9
<211> LENGTH: 116
<212> TYPE: PRT
<213> ORGANISM: artificial sequence
<220> FEATURE:
<223> OTHER INFORMATION: VH

<400> SEQUENCE: 9

Gln Val Gln Leu Val Gln Ser Gly Ala Glu Val Lys Lys Pro Gly Ala
1               5               10              15

Ser Val Lys Val Ser Cys Lys Ala Ser Gly Tyr Thr Phe Thr Thr Tyr
            20              25              30

Tyr Ile His Trp Val Arg Gln Ala Pro Gly Gln Arg Leu Glu Trp Met
        35              40              45

Gly Trp Ile Tyr Pro Gly Asn Val Asn Thr Lys Tyr Asn Glu Lys Phe
    50              55              60

Lys Gly Arg Val Thr Ile Thr Arg Asp Thr Ser Ala Ser Thr Ala Tyr
65              70              75              80

Met Glu Leu Ser Ser Leu Arg Ser Glu Asp Thr Ala Val Tyr Tyr Cys
                85              90              95

Ala Arg Gly Leu Tyr Tyr Phe Asp Tyr Trp Gly Gln Gly Thr Leu Val
            100             105             110

Thr Val Ser Ser
        115

-continued

<210> SEQ ID NO 10
<211> LENGTH: 116
<212> TYPE: PRT
<213> ORGANISM: artificial sequence
<220> FEATURE:
<223> OTHER INFORMATION: VH

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Tyr Ile His Trp Val Arg Gln Ala Pro Gly Gln Arg Leu Glu Trp Met
        35                  40                  45

Gly Trp Ile Tyr Pro Gly Asn Val Asn Thr Lys Tyr Asn Glu Lys Phe
    50                  55                  60

Lys Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Leu Tyr Tyr Phe Asp Tyr Trp Gly Gln Gly Thr Leu Val
            100                 105                 110

Thr Val Ser Ser
        115

<210> SEQ ID NO 11
<211> LENGTH: 107
<212> TYPE: PRT
<213> ORGANISM: artificial sequence
<220> FEATURE:
<223> OTHER INFORMATION: VL

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Val Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Asp Tyr Ser Ser Pro Tyr
                85                  90                  95

Thr Phe Gly Gly Gly Thr Lys Val Glu Ile Lys
            100                 105

<210> SEQ ID NO 12
<211> LENGTH: 107
<212> TYPE: PRT
<213> ORGANISM: artificial sequence
<220> FEATURE:
<223> OTHER INFORMATION: VL

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

```
Val Ala Trp Tyr Gln Gln Lys Pro Gly Lys Val Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Leu Ala Thr Tyr Phe Cys Gln Gln Asp Tyr Ser Ser Pro Tyr
                85                  90                  95

Thr Phe Gly Gly Gly Thr Lys Val Glu Ile Lys
                100                 105
```

```
<210> SEQ ID NO 13
<211> LENGTH: 119
<212> TYPE: PRT
<213> ORGANISM: artificial sequence
<220> FEATURE:
<223> OTHER INFORMATION: VH

<400> SEQUENCE: 13

Gln Val Gln Leu Lys Glu Ser Gly Pro Gly Leu Val Ala Pro Ser Gln
1               5                   10                  15

Ser Leu Ser Ile Ser Cys Thr Val Ser Gly Phe Ser Leu Ile Asp Tyr
                20                  25                  30

Gly Val Ser Trp Ile Arg Gln Pro Pro Gly Lys Gly Leu Glu Trp Leu
            35                  40                  45

Gly Val Ile Trp Gly Asp Gly Lys Ile Tyr Tyr Asn Ser Val Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Lys Gln Gly Gly Leu Leu Phe Tyr Ala Met Asp Tyr Trp Gly Gln Gly
                100                 105                 110

Thr Ser Val Thr Val Ser Ser
        115
```

```
<210> SEQ ID NO 14
<211> LENGTH: 113
<212> TYPE: PRT
<213> ORGANISM: artificial sequence
<220> FEATURE:
<223> OTHER INFORMATION: VL

<400> SEQUENCE: 14

Asp Ile Val Met Thr Gln Ser Pro Ser Ser Leu Ala Met Ser Val Gly
1               5                   10                  15

Gln Arg Val Thr Met Asn Cys Lys Ser Ser Gln Ser Leu Leu Asn Ser
                20                  25                  30

Tyr Ser Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ile Gly Ser Gly Ser Glu Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Asn Thr Pro Phe Thr Phe Gly Ser Gly Thr Lys Leu Glu Ile
```

-continued

```
               100              105              110

Lys

<210> SEQ ID NO 15
<211> LENGTH: 119
<212> TYPE: PRT
<213> ORGANISM: artificial sequence
<220> FEATURE:
<223> OTHER INFORMATION: VH

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45

Gly Val Ile Trp Gly Asp Gly Lys Ile Tyr Tyr Asn Ser Val Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gln Gly Gly Leu Leu Phe Tyr Ala Met Asp Tyr Trp Gly Gln Gly
            100                 105                 110

Thr Leu Val Thr Val Ser Ser
        115

<210> SEQ ID NO 16
<211> LENGTH: 119
<212> TYPE: PRT
<213> ORGANISM: artificial sequence
<220> FEATURE:
<223> OTHER INFORMATION: VH

<400> SEQUENCE: 16

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45

Gly Val Ile Trp Gly Asp Gly Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Gly Gly Leu Leu Phe Tyr Ala Met Asp Tyr Trp Gly Gln Gly
            100                 105                 110

Thr Leu Val Thr Val Ser Ser
        115

<210> SEQ ID NO 17
<211> LENGTH: 119
<212> TYPE: PRT
<213> ORGANISM: artificial sequence
<220> FEATURE:
<223> OTHER INFORMATION: VH
```

<400> SEQUENCE: 17

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45

Gly Val Ile Trp Gly Glu Gly Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
            85                  90                  95

Lys Gln Gly Gly Leu Leu Phe Tyr Ala Met Asp Tyr Trp Gly Gln Gly
            100                 105                 110

Thr Leu Val Thr Val Ser Ser
        115
```

<210> SEQ ID NO 18
<211> LENGTH: 119
<212> TYPE: PRT
<213> ORGANISM: artificial sequence
<220> FEATURE:
<223> OTHER INFORMATION: VH

<400> SEQUENCE: 18

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45

Gly Val Ile Trp Gly Asp Gly Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
            85                  90                  95

Arg Gln Gly Gly Leu Leu Phe Tyr Ala Met Asp Tyr Trp Gly Gln Gly
            100                 105                 110

Thr Leu Val Thr Val Ser Ser
        115
```

<210> SEQ ID NO 19
<211> LENGTH: 119
<212> TYPE: PRT
<213> ORGANISM: artificial sequence
<220> FEATURE:
<223> OTHER INFORMATION: VH

<400> SEQUENCE: 19

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
            20                  25                  30

Gly Val Ser Trp Ile Arg Gln Pro Pro Gly Lys Gly Leu Glu Trp Ile
        35                  40                  45
```

```
Gly Val Ile Trp Gly Asp Ala Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Gly Gly Leu Leu Phe Tyr Ala Met Asp Tyr Trp Gly Gln Gly
            100                 105                 110

Thr Leu Val Thr Val Ser Ser
        115

<210> SEQ ID NO 20
<211> LENGTH: 119
<212> TYPE: PRT
<213> ORGANISM: artificial sequence
<220> FEATURE:
<223> OTHER INFORMATION: VH

<400> SEQUENCE: 20

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
                20                  25                  30

Gly Val Ser Trp Ile Arg Gln Pro Pro Gly Lys Gly Leu Glu Trp Ile
            35                  40                  45

Gly Val Ile Trp Gly Gly Asp Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Gly Gly Leu Leu Phe Tyr Ala Met Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: artificial sequence
<220> FEATURE:
<223> OTHER INFORMATION: VH

<400> SEQUENCE: 21

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ile Asp Tyr
                20                  25                  30

Gly Val Ser Trp Ile Arg Gln Pro Pro Gly Lys Gly Leu Glu Trp Ile
            35                  40                  45

Gly Val Ile Trp Gly Gly Gly Lys Ile Tyr Tyr Asn Ser Val Leu Lys
    50                  55                  60

Ser Arg Val Thr Ile Ser Lys Asp Asn Ser Lys Ser Gln Val Ser Leu
65                  70                  75                  80

Lys Leu Ser Ser Val Thr Ala Ala Asp Thr Ala Val Tyr Tyr Cys Ala
                85                  90                  95

Lys Gln Gly Gly Leu Leu Phe Tyr Ala Met Asp Tyr Trp Gly Gln Gly
```

-continued

```
                100              105              110

Thr Leu Val Thr Val Ser Ser
        115

<210> SEQ ID NO 22
<211> LENGTH: 114
<212> TYPE: PRT
<213> ORGANISM: artificial sequence
<220> FEATURE:
<223> OTHER INFORMATION: VL

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Tyr Ser Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

His Tyr Asn Thr Pro Phe Thr Phe Gly Ala Gly Thr Lys Leu Glu Leu
            100                 105                 110

Lys Arg

<210> SEQ ID NO 23
<211> LENGTH: 114
<212> TYPE: PRT
<213> ORGANISM: artificial sequence
<220> FEATURE:
<223> OTHER INFORMATION: VL

<400> SEQUENCE: 23

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Tyr Ser Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Gln Ala Glu Asp Leu Ala Val Tyr Phe Cys Gln Gln
                85                  90                  95

His Tyr Asn Thr Pro Phe Thr Phe Gly Ala Gly Thr Lys Leu Glu Leu
            100                 105                 110

Lys Arg

<210> SEQ ID NO 24
<211> LENGTH: 114
<212> TYPE: PRT
<213> ORGANISM: artificial sequence
<220> FEATURE:
<223> OTHER INFORMATION: VL
```

<400> SEQUENCE: 24

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Tyr Ser Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Gln Ala Glu Asp Leu Ala Val Tyr Phe Cys Gln Gln
            85                  90                  95

His Tyr Asn Thr Pro Phe Thr Phe Gly Ala Gly Thr Lys Leu Glu Leu
            100                 105                 110

Lys Arg
```

<210> SEQ ID NO 25
<211> LENGTH: 114
<212> TYPE: PRT
<213> ORGANISM: artificial sequence
<220> FEATURE:
<223> OTHER INFORMATION: VL

<400> SEQUENCE: 25

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Thr
            20                  25                  30

Tyr Ser Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Glu Ser Gly Val
    50                  55                  60

Pro Asp Arg Phe Ser Gly Ser Gly Ser Glu Thr Asp Phe Thr Leu Thr
65                  70                  75                  80

Ile Ser Ser Leu Gln Ala Glu Asp Leu Ala Val Tyr Phe Cys Gln Gln
            85                  90                  95

His Tyr Asn Thr Pro Phe Thr Phe Gly Ala Gly Thr Lys Leu Glu Leu
            100                 105                 110

Lys Arg
```

<210> SEQ ID NO 26
<211> LENGTH: 114
<212> TYPE: PRT
<213> ORGANISM: artificial sequence
<220> FEATURE:
<223> OTHER INFORMATION: VL

<400> SEQUENCE: 26

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Lys
            20                  25                  30

Tyr Ser Gln Lys Asn Tyr Leu Ala Trp Tyr Gln Gln Lys Pro Gly Gln
        35                  40                  45

Pro Pro Lys Leu Leu Ile Tyr Phe Ala Ser Thr Arg Glu Ser Gly Val
    50                  55                  60
```

-continued

```
Pro Asp Arg Phe Ser Gly Ser Gly Ser Gly Thr Asp Phe Thr Leu Thr
65              70              75              80

Ile Ser Ser Leu Gln Ala Glu Asp Val Ala Val Tyr Tyr Cys Gln Gln
                85              90              95

His Tyr Asn Thr Pro Phe Thr Phe Gly Ala Gly Thr Lys Leu Glu Leu
            100             105             110

Lys Arg

<210> SEQ ID NO 27
<211> LENGTH: 116
<212> TYPE: PRT
<213> ORGANISM: artificial sequence
<220> FEATURE:
<223> OTHER INFORMATION: VH

<400> SEQUENCE: 27

Gln Val Gln Leu Gln Gln Ser Gly Pro Glu Leu Val Lys Pro Gly Ala
1               5               10              15

Ser Val Arg Ile Ser Cys Lys Ala Ser Gly Tyr Thr Phe Thr Ser Tyr
                20              25              30

Tyr Ile His Trp Val Lys Gln Arg Pro Gly Gln Gly Leu Glu Trp Ile
            35              40              45

Gly Trp Ile Tyr Pro Gly Asn Ala Asn Asn Lys Tyr Asn Glu Asn Phe
        50              55              60

Lys Gly Lys Ala Thr Leu Thr Ala Asp Lys Ser Ser Ser Thr Ala Tyr
65              70              75              80

Met Gln Leu Ser Ser Leu Thr Ser Glu Asp Ser Ala Val Tyr Phe Cys
                85              90              95

Ala Arg Ser Val Tyr Tyr Phe Asp Tyr Trp Gly Gln Gly Thr Thr Leu
            100             105             110

Thr Val Ser Ser
        115

<210> SEQ ID NO 28
<211> LENGTH: 107
<212> TYPE: PRT
<213> ORGANISM: artificial sequence
<220> FEATURE:
<223> OTHER INFORMATION: VL

<400> SEQUENCE: 28

Ser Val Val Met Thr Gln Thr Pro Lys Phe Leu Leu Val Ser Ala Gly
1               5               10              15

Asp Arg Val Thr Ile Thr Cys Lys Ala Ser Gln Ser Val Ser Asn Asp
                20              25              30

Val Ala Trp Tyr Gln Gln Lys Pro Gly Gln Ser Pro Lys Leu Leu Ile
            35              40              45

Tyr Tyr Ala Ser Asn Arg Asn Thr Gly Val Pro Asp Arg Phe Thr Gly
        50              55              60

Ser Gly Tyr Gly Thr Asp Phe Thr Phe Asn Ile Ser Thr Val Gln Ala
65              70              75              80

Glu Asp Leu Ala Val Tyr Phe Cys Gln Gln Asp Tyr Ser Ser Pro Tyr
                85              90              95

Thr Phe Gly Gly Gly Thr Lys Leu Glu Ile Lys
            100             105

<210> SEQ ID NO 29
```

```
<211> LENGTH: 116
<212> TYPE: PRT
<213> ORGANISM: artificial sequence
<220> FEATURE:
<223> OTHER INFORMATION: VH

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
        35                  40                  45

Gly Trp Ile Tyr Pro Gly Asn Ala Asn Asn Lys Tyr Asn Glu Asn Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Tyr Tyr Phe Asp Tyr Trp Gly Gln Gly Thr Leu Val
            100                 105                 110

Thr Val Ser Ser
        115

<210> SEQ ID NO 30
<211> LENGTH: 116
<212> TYPE: PRT
<213> ORGANISM: artificial sequence
<220> FEATURE:
<223> OTHER INFORMATION: VH

<400> SEQUENCE: 30

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Arg Leu Glu Trp Met
        35                  40                  45

Gly Trp Ile Tyr Pro Gly Asn Ala Asn Asn Lys Tyr Asn Glu Asn Phe
    50                  55                  60

Lys Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Tyr Tyr Phe Asp Tyr Trp Gly Gln Gly Thr Leu Val
            100                 105                 110

Thr Val Ser Ser
        115

<210> SEQ ID NO 31
<211> LENGTH: 107
<212> TYPE: PRT
<213> ORGANISM: artificial sequence
<220> FEATURE:
<223> OTHER INFORMATION: VL

<400> SEQUENCE: 31

Glu Ile Val Met Thr Gln Ser Pro Ala Thr Leu Ser Val Ser Pro Gly
1               5                   10                  15
```

-continued

```
Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Asn Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Ser Ser Pro Tyr
                85                  90                  95

Thr Phe Gly Gly Gly Thr Lys Val Glu Ile Lys
            100                 105

<210> SEQ ID NO 32
<211> LENGTH: 107
<212> TYPE: PRT
<213> ORGANISM: artificial sequence
<220> FEATURE:
<223> OTHER INFORMATION: VL

<400> SEQUENCE: 32

Glu Val Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Ala Trp Tyr Gln Gln Lys Pro Gly Gln Ala Pro Arg Leu Leu Ile
        35                  40                  45

Tyr Tyr Ala Ser Asn Arg Asn Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Val Glu Ile Lys
            100                 105

<210> SEQ ID NO 33
<211> LENGTH: 117
<212> TYPE: PRT
<213> ORGANISM: artificial sequence
<220> FEATURE:
<223> OTHER INFORMATION: VH

<400> SEQUENCE: 33

Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Asp Tyr
            20                  25                  30

Tyr Met His Trp Val Lys Gln Ser Arg Gly Lys Gly Leu Glu Trp Ile
        35                  40                  45

Gly Arg Val Asn Pro Asn Asn Gly Asn Thr Leu Tyr Asn Gln Lys Phe
    50                  55                  60

Arg Gly Lys Ala Ile Leu Thr Val Asp Lys Ser Ser Ser Thr Ala Tyr
65                  70                  75                  80

Met Glu Leu Arg Ser Leu Thr Ser Asp Asp Ser Ala Val Tyr Tyr Cys
                85                  90                  95

Ala Arg Glu Asp Arg Tyr Ala Phe Ala Tyr Trp Gly Gln Gly Thr Leu
            100                 105                 110
```

-continued

```
Val Thr Val Ser Ala
        115

<210> SEQ ID NO 34
<211> LENGTH: 111
<212> TYPE: PRT
<213> ORGANISM: artificial sequence
<220> FEATURE:
<223> OTHER INFORMATION: VL

<400> SEQUENCE: 34

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Thr Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ile Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Thr Trp
                85                  90                  95

Glu Ile Pro Tyr Thr Phe Gly Gly Gly Thr Lys Leu Glu Ile Lys
            100                 105                 110

<210> SEQ ID NO 35
<211> LENGTH: 7
<212> TYPE: PRT
<213> ORGANISM: artificial sequence
<220> FEATURE:
<223> OTHER INFORMATION: CDR-H1

<400> SEQUENCE: 35

Gly Tyr Thr Phe Thr Thr Tyr
1               5

<210> SEQ ID NO 36
<211> LENGTH: 10
<212> TYPE: PRT
<213> ORGANISM: artificial sequence
<220> FEATURE:
<223> OTHER INFORMATION: CDR-H1

<400> SEQUENCE: 36

Gly Tyr Thr Phe Thr Thr Tyr Tyr Ile His
1               5                   10

<210> SEQ ID NO 37
<211> LENGTH: 5
<212> TYPE: PRT
<213> ORGANISM: artificial sequence
<220> FEATURE:
<223> OTHER INFORMATION: CDR-H1

<400> SEQUENCE: 37

Thr Tyr Tyr Ile His
1               5

<210> SEQ ID NO 38
<211> LENGTH: 6
<212> TYPE: PRT
<213> ORGANISM: artificial sequence
```

-continued

```
<220> FEATURE:
<223> OTHER INFORMATION: CDR-H1

<400> SEQUENCE: 38

Thr Thr Tyr Tyr Ile His
1               5

<210> SEQ ID NO 39
<211> LENGTH: 6
<212> TYPE: PRT
<213> ORGANISM: artificial sequence
<220> FEATURE:
<223> OTHER INFORMATION: CDR-H2

<400> SEQUENCE: 39

Tyr Pro Gly Asn Val Asn
1               5

<210> SEQ ID NO 40
<211> LENGTH: 10
<212> TYPE: PRT
<213> ORGANISM: artificial sequence
<220> FEATURE:
<223> OTHER INFORMATION: CDR-H2

<400> SEQUENCE: 40

Trp Ile Tyr Pro Gly Asn Val Asn Thr Lys
1               5                   10

<210> SEQ ID NO 41
<211> LENGTH: 17
<212> TYPE: PRT
<213> ORGANISM: artificial sequence
<220> FEATURE:
<223> OTHER INFORMATION: CDR-H2

<400> SEQUENCE: 41

Trp Ile Tyr Pro Gly Asn Val Asn Thr Lys Tyr Asn Glu Lys Phe Lys
1               5                   10                  15

Gly

<210> SEQ ID NO 42
<211> LENGTH: 13
<212> TYPE: PRT
<213> ORGANISM: artificial sequence
<220> FEATURE:
<223> OTHER INFORMATION: CDR-H2

<400> SEQUENCE: 42

Trp Ile Gly Trp Ile Tyr Pro Gly Asn Val Asn Thr Lys
1               5                   10

<210> SEQ ID NO 43
<211> LENGTH: 7
<212> TYPE: PRT
<213> ORGANISM: artificial sequence
<220> FEATURE:
<223> OTHER INFORMATION: CDR-H3

<400> SEQUENCE: 43

Gly Leu Tyr Tyr Phe Asp Tyr
1               5

<210> SEQ ID NO 44
<211> LENGTH: 8
<212> TYPE: PRT
```

-continued

```
<213> ORGANISM: artificial sequence
<220> FEATURE:
<223> OTHER INFORMATION: CDR-H3

<400> SEQUENCE: 44

Ala Arg Gly Leu Tyr Tyr Phe Asp
1               5

<210> SEQ ID NO 45
<211> LENGTH: 11
<212> TYPE: PRT
<213> ORGANISM: artificial sequence
<220> FEATURE:
<223> OTHER INFORMATION: CDR-L1

<400> SEQUENCE: 45

Lys Ala Ser Gln Ser Val Ser Asn Asp Val Ala
1               5                   10

<210> SEQ ID NO 46
<211> LENGTH: 7
<212> TYPE: PRT
<213> ORGANISM: artificial sequence
<220> FEATURE:
<223> OTHER INFORMATION: CDR-L1

<400> SEQUENCE: 46

Ser Asn Asp Val Ala Trp Tyr
1               5

<210> SEQ ID NO 47
<211> LENGTH: 7
<212> TYPE: PRT
<213> ORGANISM: artificial sequence
<220> FEATURE:
<223> OTHER INFORMATION: CDR-L2

<400> SEQUENCE: 47

Tyr Ala Ser Asn Arg Tyr Thr
1               5

<210> SEQ ID NO 48
<211> LENGTH: 10
<212> TYPE: PRT
<213> ORGANISM: artificial sequence
<220> FEATURE:
<223> OTHER INFORMATION: CDR-L2

<400> SEQUENCE: 48

Leu Leu Ile Tyr Tyr Ala Ser Asn Arg Tyr
1               5                   10

<210> SEQ ID NO 49
<211> LENGTH: 9
<212> TYPE: PRT
<213> ORGANISM: artificial sequence
<220> FEATURE:
<223> OTHER INFORMATION: CDR-L3

<400> SEQUENCE: 49

Gln Gln Asp Tyr Ser Ser Pro Tyr Thr
1               5

<210> SEQ ID NO 50
<211> LENGTH: 8
<212> TYPE: PRT
<213> ORGANISM: artificial sequence
```

```
<220> FEATURE:
<223> OTHER INFORMATION: CDR-L3

<400> SEQUENCE: 50

Gln Gln Asp Tyr Ser Ser Pro Tyr
1               5

<210> SEQ ID NO 51
<211> LENGTH: 7
<212> TYPE: PRT
<213> ORGANISM: artificial sequence
<220> FEATURE:
<223> OTHER INFORMATION: CDR-H1

<400> SEQUENCE: 51

Gly Phe Ser Leu Ile Asp Tyr
1               5

<210> SEQ ID NO 52
<211> LENGTH: 10
<212> TYPE: PRT
<213> ORGANISM: artificial sequence
<220> FEATURE:
<223> OTHER INFORMATION: CDR-H1

<400> SEQUENCE: 52

Gly Phe Ser Leu Ile Asp Tyr Gly Val Ser
1               5                   10

<210> SEQ ID NO 53
<211> LENGTH: 5
<212> TYPE: PRT
<213> ORGANISM: artificial sequence
<220> FEATURE:
<223> OTHER INFORMATION: CDR-H1

<400> SEQUENCE: 53

Asp Tyr Gly Val Ser
1               5

<210> SEQ ID NO 54
<211> LENGTH: 6
<212> TYPE: PRT
<213> ORGANISM: artificial sequence
<220> FEATURE:
<223> OTHER INFORMATION: CDR-H1

<400> SEQUENCE: 54

Ile Asp Tyr Gly Val Ser
1               5

<210> SEQ ID NO 55
<211> LENGTH: 5
<212> TYPE: PRT
<213> ORGANISM: artificial sequence
<220> FEATURE:
<223> OTHER INFORMATION: CDR-H2

<400> SEQUENCE: 55

Trp Gly Asp Gly Lys
1               5

<210> SEQ ID NO 56
<211> LENGTH: 9
<212> TYPE: PRT
<213> ORGANISM: artificial sequence
<220> FEATURE:
```

<223> OTHER INFORMATION: CDR-H2

<400> SEQUENCE: 56

Val Ile Trp Gly Asp Gly Lys Ile Tyr
1               5

<210> SEQ ID NO 57
<211> LENGTH: 16
<212> TYPE: PRT
<213> ORGANISM: artificial sequence
<220> FEATURE:
<223> OTHER INFORMATION: CDR-H2

<400> SEQUENCE: 57

Val Ile Trp Gly Asp Gly Lys Ile Tyr Tyr Asn Ser Val Leu Lys Ser
1               5                   10                  15

<210> SEQ ID NO 58
<211> LENGTH: 12
<212> TYPE: PRT
<213> ORGANISM: artificial sequence
<220> FEATURE:
<223> OTHER INFORMATION: CDR-H2

<400> SEQUENCE: 58

Trp Leu Gly Val Ile Trp Gly Asp Gly Lys Ile Tyr
1               5                   10

<210> SEQ ID NO 59
<211> LENGTH: 11
<212> TYPE: PRT
<213> ORGANISM: artificial sequence
<220> FEATURE:
<223> OTHER INFORMATION: CDR-H3

<400> SEQUENCE: 59

Gln Gly Gly Leu Leu Phe Tyr Ala Met Asp Tyr
1               5                   10

<210> SEQ ID NO 60
<211> LENGTH: 12
<212> TYPE: PRT
<213> ORGANISM: artificial sequence
<220> FEATURE:
<223> OTHER INFORMATION: CDR-H3

<400> SEQUENCE: 60

Ala Lys Gln Gly Gly Leu Leu Phe Tyr Ala Met Asp
1               5                   10

<210> SEQ ID NO 61
<211> LENGTH: 17
<212> TYPE: PRT
<213> ORGANISM: artificial sequence
<220> FEATURE:
<223> OTHER INFORMATION: CDR-L1

<400> SEQUENCE: 61

Lys Ser Ser Gln Ser Leu Leu Asn Ser Tyr Ser Gln Lys Asn Tyr Leu
1               5                   10                  15

Ala

<210> SEQ ID NO 62
<211> LENGTH: 13
<212> TYPE: PRT
<213> ORGANISM: artificial sequence

```
<220> FEATURE:
<223> OTHER INFORMATION: CDR-L1

<400> SEQUENCE: 62

Leu Asn Ser Tyr Ser Gln Lys Asn Tyr Leu Ala Trp Tyr
1               5                   10

<210> SEQ ID NO 63
<211> LENGTH: 7
<212> TYPE: PRT
<213> ORGANISM: artificial sequence
<220> FEATURE:
<223> OTHER INFORMATION: CDR-L2

<400> SEQUENCE: 63

Phe Ala Ser Thr Arg Glu Ser
1               5

<210> SEQ ID NO 64
<211> LENGTH: 10
<212> TYPE: PRT
<213> ORGANISM: artificial sequence
<220> FEATURE:
<223> OTHER INFORMATION: CDR-L2

<400> SEQUENCE: 64

Leu Leu Ile Tyr Phe Ala Ser Thr Arg Glu
1               5                   10

<210> SEQ ID NO 65
<211> LENGTH: 9
<212> TYPE: PRT
<213> ORGANISM: artificial sequence
<220> FEATURE:
<223> OTHER INFORMATION: CDR-L3

<400> SEQUENCE: 65

Gln Gln His Tyr Asn Thr Pro Phe Thr
1               5

<210> SEQ ID NO 66
<211> LENGTH: 8
<212> TYPE: PRT
<213> ORGANISM: artificial sequence
<220> FEATURE:
<223> OTHER INFORMATION: CDR-L3

<400> SEQUENCE: 66

Gln Gln His Tyr Asn Thr Pro Phe
1               5

<210> SEQ ID NO 67
<211> LENGTH: 17
<212> TYPE: PRT
<213> ORGANISM: artificial sequence
<220> FEATURE:
<223> OTHER INFORMATION: CDR-L1

<400> SEQUENCE: 67

Lys Ser Ser Gln Ser Leu Leu Asn Thr Tyr Ser Gln Lys Asn Tyr Leu
1               5                   10                  15

Ala

<210> SEQ ID NO 68
<211> LENGTH: 5
<212> TYPE: PRT
```

```
<213> ORGANISM: artificial sequence
<220> FEATURE:
<223> OTHER INFORMATION: CDR-H2

<400> SEQUENCE: 68

Trp Gly Asp Ala Lys
1               5

<210> SEQ ID NO 69
<211> LENGTH: 5
<212> TYPE: PRT
<213> ORGANISM: artificial sequence
<220> FEATURE:
<223> OTHER INFORMATION: CDR-H2

<400> SEQUENCE: 69

Trp Gly Gly Gly Lys
1               5

<210> SEQ ID NO 70
<211> LENGTH: 7
<212> TYPE: PRT
<213> ORGANISM: artificial sequence
<220> FEATURE:
<223> OTHER INFORMATION: CDR-H1

<400> SEQUENCE: 70

Gly Tyr Thr Phe Thr Ser Tyr
1               5

<210> SEQ ID NO 71
<211> LENGTH: 10
<212> TYPE: PRT
<213> ORGANISM: artificial sequence
<220> FEATURE:
<223> OTHER INFORMATION: CDR-H1

<400> SEQUENCE: 71

Gly Tyr Thr Phe Thr Ser Tyr Tyr Ile His
1               5                   10

<210> SEQ ID NO 72
<211> LENGTH: 5
<212> TYPE: PRT
<213> ORGANISM: artificial sequence
<220> FEATURE:
<223> OTHER INFORMATION: CDR-H1

<400> SEQUENCE: 72

Ser Tyr Tyr Ile His
1               5

<210> SEQ ID NO 73
<211> LENGTH: 6
<212> TYPE: PRT
<213> ORGANISM: artificial sequence
<220> FEATURE:
<223> OTHER INFORMATION: CDR-H1

<400> SEQUENCE: 73

Thr Ser Tyr Tyr Ile His
1               5

<210> SEQ ID NO 74
<211> LENGTH: 6
<212> TYPE: PRT
<213> ORGANISM: artificial sequence
```

```
<220> FEATURE:
<223> OTHER INFORMATION: CDR-H2

<400> SEQUENCE: 74

Tyr Pro Gly Asn Ala Asn
1               5

<210> SEQ ID NO 75
<211> LENGTH: 10
<212> TYPE: PRT
<213> ORGANISM: artificial sequence
<220> FEATURE:
<223> OTHER INFORMATION: CDR-H2

<400> SEQUENCE: 75

Trp Ile Tyr Pro Gly Asn Ala Asn Asn Lys
1               5               10

<210> SEQ ID NO 76
<211> LENGTH: 17
<212> TYPE: PRT
<213> ORGANISM: artificial sequence
<220> FEATURE:
<223> OTHER INFORMATION: CDR-H2

<400> SEQUENCE: 76

Trp Ile Tyr Pro Gly Asn Ala Asn Asn Lys Tyr Asn Glu Asn Phe Lys
1               5               10              15

Gly

<210> SEQ ID NO 77
<211> LENGTH: 13
<212> TYPE: PRT
<213> ORGANISM: artificial sequence
<220> FEATURE:
<223> OTHER INFORMATION: CDR-H2

<400> SEQUENCE: 77

Trp Ile Gly Trp Ile Tyr Pro Gly Asn Ala Asn Asn Lys
1               5               10

<210> SEQ ID NO 78
<211> LENGTH: 7
<212> TYPE: PRT
<213> ORGANISM: artificial sequence
<220> FEATURE:
<223> OTHER INFORMATION: CDR-H3

<400> SEQUENCE: 78

Ser Val Tyr Tyr Phe Asp Tyr
1               5

<210> SEQ ID NO 79
<211> LENGTH: 8
<212> TYPE: PRT
<213> ORGANISM: artificial sequence
<220> FEATURE:
<223> OTHER INFORMATION: CDR-H3

<400> SEQUENCE: 79

Ala Arg Ser Val Tyr Tyr Phe Asp
1               5

<210> SEQ ID NO 80
<211> LENGTH: 7
<212> TYPE: PRT
```

```
<213> ORGANISM: artificial sequence
<220> FEATURE:
<223> OTHER INFORMATION: CDR-L2

<400> SEQUENCE: 80

Tyr Ala Ser Asn Arg Asn Thr
1               5

<210> SEQ ID NO 81
<211> LENGTH: 10
<212> TYPE: PRT
<213> ORGANISM: artificial sequence
<220> FEATURE:
<223> OTHER INFORMATION: CDR-L2

<400> SEQUENCE: 81

Leu Leu Ile Tyr Tyr Ala Ser Asn Arg Asn
1               5                   10

<210> SEQ ID NO 82
<211> LENGTH: 7
<212> TYPE: PRT
<213> ORGANISM: artificial sequence
<220> FEATURE:
<223> OTHER INFORMATION: CDR-H1

<400> SEQUENCE: 82

Gly Tyr Ser Phe Thr Asp Tyr
1               5

<210> SEQ ID NO 83
<211> LENGTH: 10
<212> TYPE: PRT
<213> ORGANISM: artificial sequence
<220> FEATURE:
<223> OTHER INFORMATION: CDR-H1

<400> SEQUENCE: 83

Gly Tyr Ser Phe Thr Asp Tyr Tyr Met His
1               5                   10

<210> SEQ ID NO 84
<211> LENGTH: 5
<212> TYPE: PRT
<213> ORGANISM: artificial sequence
<220> FEATURE:
<223> OTHER INFORMATION: CDR-H1

<400> SEQUENCE: 84

Asp Tyr Tyr Met His
1               5

<210> SEQ ID NO 85
<211> LENGTH: 6
<212> TYPE: PRT
<213> ORGANISM: artificial sequence
<220> FEATURE:
<223> OTHER INFORMATION: CDR-H1

<400> SEQUENCE: 85

Thr Asp Tyr Tyr Met His
1               5

<210> SEQ ID NO 86
<211> LENGTH: 6
<212> TYPE: PRT
<213> ORGANISM: artificial sequence
```

-continued

```
<220> FEATURE:
<223> OTHER INFORMATION: CDR-H2

<400> SEQUENCE: 86

Asn Pro Asn Asn Gly Asn
1               5

<210> SEQ ID NO 87
<211> LENGTH: 10
<212> TYPE: PRT
<213> ORGANISM: artificial sequence
<220> FEATURE:
<223> OTHER INFORMATION: CDR-H2

<400> SEQUENCE: 87

Arg Val Asn Pro Asn Asn Gly Asn Thr Leu
1               5               10

<210> SEQ ID NO 88
<211> LENGTH: 17
<212> TYPE: PRT
<213> ORGANISM: artificial sequence
<220> FEATURE:
<223> OTHER INFORMATION: CDR-H2

<400> SEQUENCE: 88

Arg Val Asn Pro Asn Asn Gly Asn Thr Leu Tyr Asn Gln Lys Phe Arg
1               5               10              15

Gly

<210> SEQ ID NO 89
<211> LENGTH: 13
<212> TYPE: PRT
<213> ORGANISM: artificial sequence
<220> FEATURE:
<223> OTHER INFORMATION: CDR-H2

<400> SEQUENCE: 89

Trp Ile Gly Arg Val Asn Pro Asn Asn Gly Asn Thr Leu
1               5               10

<210> SEQ ID NO 90
<211> LENGTH: 8
<212> TYPE: PRT
<213> ORGANISM: artificial sequence
<220> FEATURE:
<223> OTHER INFORMATION: CDR-H3

<400> SEQUENCE: 90

Glu Asp Arg Tyr Ala Phe Ala Tyr
1               5

<210> SEQ ID NO 91
<211> LENGTH: 9
<212> TYPE: PRT
<213> ORGANISM: artificial sequence
<220> FEATURE:
<223> OTHER INFORMATION: CDR-H3

<400> SEQUENCE: 91

Ala Arg Glu Asp Arg Tyr Ala Phe Ala
1               5

<210> SEQ ID NO 92
<211> LENGTH: 15
<212> TYPE: PRT
```

<213> ORGANISM: artificial sequence
<220> FEATURE:
<223> OTHER INFORMATION: CDR-L1

<400> SEQUENCE: 92

Arg Ala Ser Gln Ser Val Ser Thr Ser Ser Tyr Thr Tyr Met His
1               5                   10                  15

<210> SEQ ID NO 93
<211> LENGTH: 11
<212> TYPE: PRT
<213> ORGANISM: artificial sequence
<220> FEATURE:
<223> OTHER INFORMATION: CDR-L1

<400> SEQUENCE: 93

Ser Thr Ser Ser Tyr Thr Tyr Met His Trp Tyr
1               5                   10

<210> SEQ ID NO 94
<211> LENGTH: 7
<212> TYPE: PRT
<213> ORGANISM: artificial sequence
<220> FEATURE:
<223> OTHER INFORMATION: CDR-L2

<400> SEQUENCE: 94

Tyr Ala Ser Asn Leu Glu Ser
1               5

<210> SEQ ID NO 95
<211> LENGTH: 10
<212> TYPE: PRT
<213> ORGANISM: artificial sequence
<220> FEATURE:
<223> OTHER INFORMATION: CDR-L2

<400> SEQUENCE: 95

Leu Leu Ile Lys Tyr Ala Ser Asn Leu Glu
1               5                   10

<210> SEQ ID NO 96
<211> LENGTH: 9
<212> TYPE: PRT
<213> ORGANISM: artificial sequence
<220> FEATURE:
<223> OTHER INFORMATION: CDR-L3

<400> SEQUENCE: 96

Gln His Thr Trp Glu Ile Pro Tyr Thr
1               5

<210> SEQ ID NO 97
<211> LENGTH: 8
<212> TYPE: PRT
<213> ORGANISM: artificial sequence
<220> FEATURE:
<223> OTHER INFORMATION: CDR-L3

<400> SEQUENCE: 97

Gln His Thr Trp Glu Ile Pro Tyr
1               5

ANTIBODY AGAINST NECTIN-4 AND APPLICATION THEREOF

CROSS-REFERENCE TO RELATED APPLICATION(S)

The present application is a U.S. National Phase Patent Application of International Application Number PCT/CN2021/088661, filed on Apr. 21, 2021, which claims the priority benefit of Chinese Patent Application Number 202010320420.3 filed on Apr. 21, 2020, the entire content of each of which is incorporated herein by reference.

SEQUENCE LISTING

The instant application contains a Sequence Listing previously submitted to WIPO in ASCII format and the entire content of the electronic submission of the sequence listing is incorporated by reference in its entirety for all purposes. The ASCII file is named "LC21210004P-seqI.txt." was last modified on Oct. 28, 2021, and is 58.2 kb in size.

TECHNICAL FIELD

The present disclosure belongs to the field of antibody medicine, and particularly relates to an antibody against human Nectin-4 and use of the antibody in preparing medicaments.

BACKGROUND OF THE INVENTION

Nectin-4 (also known as PVRL4, poliovirus receptor-like molecule 4) is a type I transmembrane glycoprotein having a molecular mass of 66 kD, and belongs to the Nectin family of Ig superfamily proteins. Nectin-4 has an extracellular region with three immunoglobulin-like (Ig-like) domains (VCC); and, serves a role in the formation and maintenance of adhesion connection together with cadherin.

Nectin-4 is closely associated with the generation and development of various tumor cells. Nectin-4 has been found to be expressed in a number of solid tumors, especially bladder cancer; as a tumor-associated antigen, Nectin-4 has detection rates of tissue expression in breast, ovarian and lung cancers accounting for 50% of breast cancer, 49% of ovarian cancer, and 86% of lung cancer respectively, and plays a key role in the development, invasion, and metastasis of these epithelial malignancies. Therefore, Nectin-4 has become an important target for the diagnosis and treatment of a plurality of solid tumors.

Currently a major drug aimed at Nectin-4 is Enfortumab vedotin, which is an antibody-drug conjugate formed by conjugating an anti-Nectin-4 monoclonal antibody and a cell killing agent monomethylenyl auristatin E (MMAE). Enfortumab vedotin is mainly used for the treatment of bladder cancer, especially urothelial cancer, and has received FDA Breakthrough Therapy Designation in March 2018. In addition, other researches show that the adhesion factor Nectin-4 not only can be used as an effective prognostic factor in breast cancer, but also can be used as an effective treatment target for patients with Triple Negative Breast Cancer (TNBC); and, in vitro and in vivo studies prove that anti-Nectin-4 antibody-drug conjugates (ADCs) have better curative effects on local and metastatic TNBCs.

SUMMARY OF THE INVENTION

The technical problem to be solved by the present disclosure is to obtain high-affinity antibodies specifically binding to Nectin-4 through hybridoma screening and humanization, wherein fully human antibody sequences are to be obtained by humanization engineering.

For the technical problem as described above, an object of the present disclosure to provide an antibody molecule or fragment thereof specifically binding to Nectin-4, in particular human Nectin-4, and also to provide uses thereof. "Fragment" of an antibody as described herein encompasses, among other things, various functional fragments of the antibody, e.g., an antigen-binding portion thereof, such as Fab, F(ab')$_2$, or scFv fragments.

The present disclosure provides the following technical solutions.

In one aspect, the present disclosure provides an antibody molecule or fragment thereof which comprises a heavy chain variable region (VH) and a light chain variable region (VL) comprising a combination of heavy and light chain CDRs selected from:

(1) CDR-H1 (GYTFTTY), CDR-H2 (YPGNVN), and CDR-H3 (GLYYFDY) as shown in SEQ ID NOs: 35, 39, and 43; and, CDR-L1 (KASQSVSNDVA), CDR-L2 (YASNRYT), and CDR-L3 (QQDYSSPYT) as shown in SEQ ID NOs: 45, 47, and 49;

(2) CDR-H1 (GYTFTTYYIH), CDR-H2 (WIYPGNVNTK), and CDR-H3 (GLYYFDY) as shown in SEQ ID NOs: 36, 40, and 43; and, CDR-L1 (KASQSVSNDVA), CDR-L2 (YASNRYT), and CDR-L3 (QQDYSSPYT) as shown in SEQ ID NOs: 45, 47, and 49;

(3) CDR-H1 (TYYIH), CDR-H2 (WIYPGNVNT-KYNEKFKG), and CDR-H3 (GLYYFDY) as shown in SEQ ID NOs: 37, 41, and 43; and, CDR-L1 (KASQSVSNDVA), CDR-L2 (YASNRYT), and CDR-L3 (QQDYSSPYT) as shown in SEQ ID NOs: 45, 47, and 49;

(4) CDR-H1 (TTYYIH), CDR-H2 (WIGWIYPGNVNTK), and CDR-H3 (ARGLYYFD) as shown in SEQ ID NOs: 38, 42, and 44; and, CDR-L1 (SNDVAWY), CDR-L2 (LLIYYASNRY), and CDR-L3 (QQDYSSPY) as shown in SEQ ID NOs: 46, 48, and 50;

(5) CDR-H1 (GFSLIDY), CDR-H2 (WGDGK), and CDR-H3 (QGGLLFYAMDY) as shown in SEQ ID NOs: 51, 55, and 59; and, CDR-L1 (KSSQSLLNSYS-QKNYLA), CDR-L2 (FASTRES), and CDR-L3 (QQHYNTPFT) as shown in SEQ ID NOs: 61, 63, and 65;

(6) CDR-H1 (GFSLIDYGVS), CDR-H2 (VIWGDG-KIY), and CDR-H3 (QGGLLFYAMDY) as shown in SEQ ID NOs: 52, 56, and 59; and, CDR-L1 (KSSQSLLNSYSQKNYLA), CDR-L2 (FASTRES), and CDR-L3 (QQHYNTPFT) as shown in SEQ ID NOs: 61, 63, and 65;

(7) CDR-H1 (DYGVS), CDR-H2 (VIWGDGKIYYNS-VLKS), and CDR-H3 (QGGLLFYAMDY) as shown in SEQ ID NOs: 53, 57, and 59; and, CDR-L1 (KSSQSLLNSYSQKNYLA), CDR-L2 (FASTRES), and CDR-L3 (QQHYNTPFT) as shown in SEQ ID NOs: 61, 63, and 65;

(8) CDR-H1 (IDYGVS), CDR-H2 (WLGVIWGDG-KIY), and CDR-H3 (AKQGGLLFYAMD) as shown in SEQ ID NOs: 54, 58, and 60; and, CDR-L1 (LNSYS-QKNYLAWY), CDR-L2 (LLIYFASTRE), and CDR-L3 (QQHYNTPF) as shown in SEQ ID NOs: 62, 64, and 66;

(9) CDR-H1 (GFSLIDY), CDR-H2 (WGDGK), and CDR-H3 (QGGLLFYAMDY) as shown in SEQ ID NOs: 51, 55, and 59; and, CDR-L1 (KSSQSLLN-TYSQKNYLA), CDR-L2 (FASTRES), and CDR-L3 (QQHYNTPFT) as shown in SEQ ID NOs: 67, 63, and 65;

(10) CDR-H1 (GFSLIDY), CDR-H2 (WGDAK), and CDR-H3 (QGGLLFYAMDY) as shown in SEQ ID NOs: 51, 68, and 59; and, CDR-L1 (KSSQSLLN-TYSQKNYLA), CDR-L2 (FASTRES), and CDR-L3 (QQHYNTPFT) as shown in SEQ ID NOs: 67, 63, and 65;

(11) CDR-H1 (GFSLIDY), CDR-H2 (WGGGK), and CDR-H3 (QGGLLFYAMDY) as shown in SEQ ID NOs: 51, 69, and 59; and, CDR-L1 (KSSQSLLN-TYSQKNYLA), CDR-L2 (FASTRES), and CDR-L3 (QQHYNTPFT) as shown in SEQ ID NOs: 67, 63, 65;

(12) CDR-H1 (GYTFTSY), CDR-H2 (YPGNAN), and CDR-H3 (SVYYFDY) as shown in SEQ ID NOs: 70, 74, and 78; and, CDR-L1 (KASQSVSNDVA), CDR-L2 (YASNRNT), and CDR-L3 (QQDYSSPYT) as shown in SEQ ID NOs: 45, 80, and 49;

(13) CDR-H1 (GYTFTSYYIH), CDR-H2 (WIYPG-NANNK), and CDR-H3 (SVYYFDY) as shown in SEQ ID NOs: 71, 75, and 78; and, CDR-L1 (KASQSVSNDVA), CDR-L2 (YASNRNT), and CDR-L3 (QQDYSSPYT) as shown in SEQ ID NOs: 45, 80, and 49;

(14) CDR-H1 (SYYIH), CDR-H2 (WIYPG-NANNKYNENFKG), and CDR-H3 (SVYYFDY) as shown in SEQ ID NOs: 72, 76, and 78; and, CDR-L1 (KASQSVSNDVA), CDR-L2 (YASNRNT), and CDR-L3 (QQDYSSPYT) as shown in SEQ ID NOs: 45, 80, and 49;

(15) CDR-H1 (TSYYIH), CDR-H2 (WIGWIYPG-NANNK), and CDR-H3 (ARSVYYFD) as shown in SEQ ID NOs: 73, 77, and 79; and, CDR-L1 (SNDVAWY), CDR-L2 (LLIYYASNRN), and CDR-L3 (QQDYSSPY) as shown in SEQ ID NOs: 46, 81, and 50;

(16) CDR-H1 (GYSFTDY), CDR-H2 (NPNNGN), and CDR-H3 (EDRYAFAY) as shown in SEQ ID NOs: 82, 86, and 90; and, CDR-L1 (RASQSVSTSSYTYMH), CDR-L2 (YASNLES), and CDR-L3 (QHTWEIPYT) as shown in SEQ ID NOs: 92, 94, and 96;

(17) CDR-H1 (GYSFTDYYMH), CDR-H2 (RVNPNNG-NTL), and CDR-H3 (EDRYAFAY) as shown in SEQ ID NOs: 83, 87, and 90; and, CDR-L1 (RASQSVST-SSYTYMH), CDR-L2 (YASNLES), and CDR-L3 (QHTWEIPYT) as shown in SEQ ID NOs: 92, 94, and 96;

(18) CDR-H1 (DYYMH), CDR-H2 (RVNPNNGNT-LYNQKFRG), and CDR-H3 (EDRYAFAY) as shown in SEQ ID NOs: 84, 88, and 90; and, CDR-L1 (RASQSVSTSSYTYMH), CDR-L2 (YASNLES), and CDR-L3 (QHTWEIPYT) as shown in SEQ ID NOs: 92, 94, and 96; and

(19) CDR-H1 (TDYYMH), CDR-H2 (WIGRVNPNNG-NTL), and CDR-H3 (AREDRYAFA) as shown in SEQ ID NOs: 85, 89, and 91; and, CDR-L1 (STS-SYTYMHWY), CDR-L2 (LLIKYASNLE), and CDR-L3 (QHTWEIPY) as shown in SEQ ID NOs: 93, 95, and 97.

The heavy chain variable region or light chain variable region in the antibody molecule or fragment thereof of the present disclosure comprises the above domain components in an arrangement as FR1-CDR1-FR2-CDR2-FR3-CDR3-FR4, in which FR is the framework region, according to the domain composition of heavy chain variable region or light chain variable region in an antibody commonly known in the art.

Preferably, in the antibody molecule or fragment thereof provided by the present disclosure, the heavy chain variable region comprises an amino acid sequence as shown in SEQ ID NO: 7, 9, or 10, or an amino acid sequence having at least 75% identity to the amino acid sequence as shown; and, the light chain variable region comprises an amino acid sequence as shown in SEQ ID NO: 8, 11, or 12, or an amino acid sequence having at least 75% identity to the amino acid sequence as shown; or, the heavy chain variable region comprises an amino acid sequence as shown in SEQ ID NO: 13, 15, 16, 18, 19, 20, or 21, or an amino acid sequence having at least 75% identity to the amino acid sequence as shown; and, the light chain variable region comprises an amino acid sequence as shown in SEQ ID NO: 14, 22, 23, or 25, or an amino acid sequence having at least 75% identity to the amino acid sequence as shown; or the heavy chain variable region comprises an amino acid sequence as shown in SEQ ID NO: 27, 29, or 30, or an amino acid sequence having at least 75% identity to the amino acid sequence as shown; and, the light chain variable region comprises an amino acid sequence as shown in SEQ ID NO: 28, 31, or 32, or an amino acid sequence having at least 75% identity to the amino acid sequence as shown; or the heavy chain variable region comprises an amino acid sequence as shown in SEQ ID NO: 33, or an amino acid sequence having at least 75% identity to the amino acid sequence as shown; and, the light chain variable region comprises an amino acid sequence as shown in SEQ ID NO: 34, or an amino acid sequence having at least 75% identity to the amino acid sequence as shown.

According to particular embodiments of the present disclosure, the heavy chain variable region and the light chain variable region in the antibody molecule or fragment thereof are selected from combinations of amino acid sequences as follows:

(1) an amino acid sequence as shown in SEQ ID NO: 7 or an amino acid sequence having at least 75% identity to the amino acid sequence as shown in SEQ ID NO: 7; and, an amino acid sequence as shown in SEQ ID NO: 8 or an amino acid sequence having at least 75% identity to the amino acid sequence as shown in SEQ ID NO: 8;

(2) an amino acid sequence as shown in SEQ ID NO: 9 or an amino acid sequence having at least 75% identity to the amino acid sequence as shown in SEQ ID NO: 9; and, an amino acid sequence as shown in SEQ ID NO: 11 or an amino acid sequence having at least 75% identity to the amino acid sequence as shown in SEQ ID NO: 11;

(3) an amino acid sequence as shown in SEQ ID NO: 9 or an amino acid sequence having at least 75% identity to the amino acid sequence as shown in SEQ ID NO: 9; and, an amino acid sequence as shown in SEQ ID NO: 12 or an amino acid sequence having at least 75% identity to the amino acid sequence as shown in SEQ ID NO: 12;

(4) an amino acid sequence as shown in SEQ ID NO: 10 or an amino acid sequence having at least 75% identity to the amino acid sequence as shown in SEQ ID NO: 10; and, an amino acid sequence as shown in SEQ ID NO: 11 or an amino acid sequence having at least 75% identity to the amino acid sequence as shown in SEQ ID NO: 11;

(5) an amino acid sequence as shown in SEQ ID NO: 10 or an amino acid sequence having at least 75% identity to the amino acid sequence as shown in SEQ ID NO: 10; and, an amino acid sequence as shown in SEQ ID NO: 12 or an amino acid sequence having at least 75% identity to the amino acid sequence as shown in SEQ ID NO: 12;

(6) an amino acid sequence as shown in SEQ ID NO: 13 or an amino acid sequence having at least 75% identity to the amino acid sequence as shown in SEQ ID NO: 13; and, an amino acid sequence as shown in SEQ ID NO: 14 or an amino acid sequence having at least 75% identity to the amino acid sequence as shown in SEQ ID NO: 14;

(7) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 22 or an amino acid sequence having at least 75% identity to the amino acid sequence as shown in SEQ ID NO: 22;

(8) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 23 or an amino acid sequence having at least 75% identity to the amino acid sequence as shown in SEQ ID NO: 23;

(9) an amino acid sequence as shown in SEQ ID NO: 16 or an amino acid sequence having at least 75% identity to the amino acid sequence as shown in SEQ ID NO: 16; and, an amino acid sequence as shown in SEQ ID NO: 25 or an amino acid sequence having at least 75% identity to the amino acid sequence as shown in SEQ ID NO: 25;

(10) an amino acid sequence as shown in SEQ ID NO: 19 or an amino acid sequence having at least 75% identity to the amino acid sequence as shown in SEQ ID NO: 19; and, an amino acid sequence as shown in SEQ ID NO: 25 or an amino acid sequence having at least 75% identity to the amino acid sequence as shown in SEQ ID NO: 25;

(11) an amino acid sequence as shown in SEQ ID NO: 21 or an amino acid sequence having at least 75% identity to the amino acid sequence as shown in SEQ ID NO: 21; and, an amino acid sequence as shown in SEQ ID NO: 25 or an amino acid sequence having at least 75% identity to the amino acid sequence as shown in SEQ ID NO: 25;

(12) an amino acid sequence as shown in SEQ ID NO: 27 or an amino acid sequence having at least 75% identity to the amino acid sequence as shown in SEQ ID NO: 27; and, an amino acid sequence as shown in SEQ ID NO: 28 or an amino acid sequence having at least 75% identity to the amino acid sequence as shown in SEQ ID NO: 28;

(13) an amino acid sequence as shown in SEQ ID NO: 29 or an amino acid sequence having at least 75% identity to the amino acid sequence as shown in SEQ ID NO: 29; and, an amino acid sequence as shown in SEQ ID NO: 32 or an amino acid sequence having at least 75% identity to the amino acid sequence as shown in SEQ ID NO: 32;

(14) an amino acid sequence as shown in SEQ ID NO: 30 or an amino acid sequence having at least 75% identity to the amino acid sequence as shown in SEQ ID NO: 30; and, an amino acid sequence as shown in SEQ ID NO: 32 or an amino acid sequence having at least 75% identity to the amino acid sequence as shown in SEQ ID NO: 32; or,

(15) an amino acid sequence as shown in SEQ ID NO: 33 or an amino acid sequence having at least 75% identity to the amino acid sequence as shown in SEQ ID NO: 33; and, an amino acid sequence as shown in SEQ ID NO: 34 or an amino acid sequence having at least 75% identity to the amino acid sequence as shown in SEQ ID NO: 34.

According to the above specific amino acid sequences of the heavy chain variable region or the light chain variable region provided by the present disclosure, the amino acid sequences of heavy chain CDRs and light chain CDRs contained therein can be determined conventionally by those skilled in the art, and the obtained heavy chain CDRs and light chain CDRs determined by other methods known in the art and their combinations are also covered by the scope of the present disclosure.

The antibody molecule or fragment thereof provided by the present disclosure binds to a poliovirus receptor-like molecule 4 (Nectin-4), preferably mammalian Nectin-4, more preferably primate Nectin-4, further preferably human or cyno Nectin-4, in particular human Nectin-4.

Preferably, the antibody molecule is a murine antibody, a chimeric antibody or a fully or partially humanized antibody; and, the fragment is any fragment of the antibody molecule capable of specifically binding to Nectin-4, e.g., single-chain variable fragment (scFv), disulfide-stabilized Fv fragment (dsFv), (disulfide-stabilized Fv fragment)$_2$ (dsFv)$_2$, Fab fragment, Fab' fragment, F(ab')$_2$ fragment, or variable fragment (Fv).

Preferably, the antibody molecule is a monoclonal antibody or a single chain antibody.

Preferably, the antibody molecule or fragment thereof further comprises a human or murine constant region, preferably a murine or human heavy chain constant region (CH) and/or a light chain constant region (CL); preferably, the antibody molecule or fragment thereof comprises a heavy chain and a light chain, e.g., two heavy and light chains. More preferably, the antibody molecule or fragment thereof comprises a heavy chain constant region of an IgG, IgA, IgM, IgD, or IgE type and/or a light chain constant region of a kappa or lambda type.

According to particular embodiments of the present disclosure, the antibody molecule provided by the present disclosure is a monoclonal antibody, preferably a humanized monoclonal antibody; preferably, the heavy chain constant region of the monoclonal antibody is of an IgG1 type and the light chain constant region is of a kappa type. For example, the heavy chain constant region of the monoclonal antibody comprises an amino acid sequence as shown in SEQ ID NO: 4 or an amino acid sequence having at least 75% identity to the amino acid sequence as shown; and, the light chain constant region of the monoclonal antibody comprises an amino acid sequence as shown in SEQ ID NO. 5 or an amino acid sequence having at least 75% identity to the amino acid sequence as shown.

The "at least 75% identity" in the context of the present disclosure is any percent identity between 75% and 100%, such as 75%, 80%, 85%, 90%, even 91%, 92%, 93%, 94%, 95%, 96%, 97%, 98%, or 99% identity.

In another aspect, the present disclosure provides a nucleic acid molecule comprising a nucleotide sequence encoding a heavy chain variable region, a light chain variable region, a heavy chain or a light chain comprised in the antibody molecule or fragment thereof according to the present disclosure.

The nucleic acid molecule according to the present disclosure may be cloned into a vector which in turn transfects or transforms a host cell. Therefore, in yet another aspect, the present disclosure provides a vector comprising the nucleic acid molecule according to the present disclosure. The vector may be a eukaryotic expression vector, a prokaryotic expression vector, an artificial chromosome, a phage vector and the like.

The vector or nucleic acid molecule of the present disclosure may be used to transform or transfect a host cell or in any way enter a host cell for antibody preservation or expression, etc. Thus, in a further aspect, the present disclosure provides a host cell comprising the nucleic acid molecule and/or vector according to the present disclosure, or transformed or transfected with the nucleic acid molecule and/or vector according to the present disclosure. The host cell may be any prokaryotic or eukaryotic cell, such as a bacterial or insect, fungus, plant or animal cell.

The antibody molecule according to the present disclosure may be obtained using any conventional techniques known in the art. For example, the heavy chain variable region and/or the light chain variable region of the antibody molecule or the heavy chain and/or the light chain of the antibody molecule may be obtained from the nucleic acid molecule provided by the present disclosure, and then the antibody molecule is obtained by assembling them with optional other domains of the antibody molecule; alternatively, the host cell provided by the present disclosure is cultured under conditions that allow the host cell to express the heavy chain variable region and/or the light chain variable region of the antibody molecule or the heavy chain and/or the light chain of the antibody molecule and assemble them into an antibody. Optionally, the method may further include a step of recovering the produced antibody molecule.

The antibody molecule or fragment thereof, the nucleic acid molecule, the vector, the host cell, or the fusion protein provided by the present disclosure may be contained in a composition, more particularly, a pharmaceutical preparation, to be used for various purposes as actually needed. Thus, in a further aspect, the present disclosure also provides a composition comprising an antibody molecule or fragment thereof, a nucleic acid molecule, a vector, and/or a host cell according to the present disclosure. Preferably, the composition is a pharmaceutical composition, optionally comprising a pharmaceutically acceptable carrier, adjuvant, or excipient.

In yet another aspect, the present disclosure also provides use of the antibody molecule or fragment thereof, the nucleic acid molecule, the vector, the host cell, and/or the composition in the manufacture of an agent for the detection or diagnosis of a disease or disorder.

Accordingly, the present disclosure further provides a method for detecting or diagnosing a disease or disorder, comprising contacting the antibody molecule or fragment thereof, the nucleic acid molecule, the vector, the host cell, and/or the composition with a sample from a subject. The subject is a mammal, preferably a primate, more preferably a human.

In a further aspect, the present disclosure also provides use of the antibody molecule or fragment thereof in the preparation of an antibody-drug conjugate.

Accordingly, the present disclosure provides an antibody-drug conjugate formed by conjugating an antibody molecule or fragment thereof according to the present disclosure to a cytotoxic moiety.

Preferably, the cytotoxic moiety is a tubulin inhibitor, a topoisomerase inhibitor, or a DNA binding agent. Preferably, the tubulin inhibitor is selected from the group consisting of Maytansinoids, Monomethyl auristatin E (MMAE), Monomethyl auristatin F (MMAF), Monomethyl Dolastatin 10, Tubulysin and its derivatives, Cryptophycin and its derivatives, and Taltobulin. Preferably, the topoisomerase inhibitor is selected from the group consisting of PNU-159682, the metabolite of doxorubicin and its derivatives, and SN38, the metabolite of irinotecan (CPT-11) and its derivatives. Preferably, the DNA binding agent is selected from the group consisting of PBD and its derivatives, and Duocarmycine and its derivatives.

In yet a further aspect, the present disclosure also provides use of the antibody molecule or fragment thereof, the nucleic acid molecule, the vector, the host cell, the composition and/or the antibody-drug conjugate in the manufacture of a medicament for the prevention or treatment of a disease or disorder.

In another aspect, the present disclosure also provides a method for preventing or treating a disease or disorder, comprising administering to a subject in need thereof an antibody molecule or fragment thereof, a nucleic acid molecule, a vector, a host cell, a composition and/or an antibody-drug conjugate according to the present disclosure. The subject is a mammal, more preferably a human.

Accordingly, in a further aspect, the present disclosure provides a kit comprising an antibody molecule or fragment thereof, a nucleic acid molecule, a vector, a host cell, a composition and/or an antibody-drug conjugate according to the present disclosure. The kit may be used for therapeutic, detection or diagnostic purposes, such as treating, detecting or diagnosing a disease or disorder.

According to various embodiments provided by the present disclosure, the antibody molecule or fragment thereof, the nucleic acid molecule, the vector, the host cell, the composition and/or the antibody-drug conjugate may be used for preventing, treating, detecting or diagnosing a disease or disorder related to high expression of Nectin-4. Preferably, the disease or disorder is a tumor or cancer in which Nectin-4 is highly expressed, in particular a solid tumor. For example, the disease or disorder is bladder cancer, pancreatic cancer, breast cancer (including triple negative and basal subtypes), non-small cell lung cancer, gastric cancer, esophageal cancer, ovarian cancer, etc.; in particular bladder, breast, ovarian or lung cancer.

Compared with prior arts, high-affinity antibodies specifically binding to Nectin-4 are obtained through hybridoma screening and humanization in the present disclosure, wherein fully human antibody sequences are obtained by humanization engineering. Moreover, researches on physicochemical properties and cytological activities of the molecules provided confirm that sequences of clinically effective lead drug molecules are obtained.

BRIEF DESCRIPTION OF THE DRAWINGS

Embodiments of the present disclosure are described in detail below with reference to the attached figures, in which.

DETAILED DESCRIPTION OF PREFERRED EMBODIMENTS

The present disclosure is illustrated below with reference to specific examples. It will be understood by those skilled in the art that these examples are merely illustrative of the present disclosure and do not limit the scope of the present disclosure in any way.

The experimental procedures in the following examples are all conventional, unless otherwise specified. The raw materials and reagents used in the following examples are all commercially available products, unless otherwise specified.

The heavy chain amino acid sequence and light chain amino acid sequence of control antibody Enfortumab are as shown in SEQ ID NO: 1 and SEQ ID NO: 2.

Sequences of antibodies provided by the present disclo-sure are shown in Annex Tables I to IV.

Antigen i.e. recombinant NECTIN4 protein (Accession No.: NP_002178.2, 32 aa-349 aa) is as shown in SEQ ID NO: 3.

Example 1 Synthesis and Expression of Control Antibody

Fully synthesized genes coding for the heavy chain and light chain variable regions of Enfortumab were cloned into upstream of genes coding for human-kappa light chain constant region and human IgG1 heavy chain constant region in eukaryotic expression vector pCDNA3.1 respec-tively, to obtain a light chain expression vector and a heavy chain expression vector of Enfortumab. The two vectors were transferred into *Escherichia coli* for expansion, and a large amount of vectors containing antibody light chain (SEQ ID NO: 2) gene and heavy chain (SEQ ID NO: 1) gene of Enfortumab were obtained through separation. HEK293 cells were co-transfected with the two vectors mixed with Polyethyleneimine (PEI), and culture supernatant was col-lected 5-6 days after cell transfection. Antibody Enfortumab was obtained by purifying the expression supernatant with a Mabselect affinity chromatography column.

Example 2 Preparation of Antigen Nectin-4 Expressing Cell Line

The reading frame of Nectin-4 gene was cloned from a vector containing Nectin-4 cDNA (Sino Biological, Inc., Cat.: HG19771-UT) by PCR, and cloned into a stable expression vector containing Glutamine Synthetase (GS) gene for screening by enzyme digestion. Suspension cul-tured CHO-K1 cells were electrotransfected (Nucleofector IIb, Lonza) and the transfected cells were transferred into CD CHO AGT™ medium (Gibco, Cat.: 12490-025) con-taining 50 μM MSX (Sigma, Cat.: M5379), and inoculated in a 96-well cell culture plate. After being placed at 37° C., 5% $CO_2$ for 2-3 weeks, 9 wells containing cells were obtained through prescreening with MSX pressure screen-ing, and the cells were expanded in 24-well cell culture plates, and finally clone S8 having a high expression of the antigen was selected via flow cytometry (FACS) analysis. Scale-up culture of the clone was performed and the cells were cryopreserved.

Figure 1:
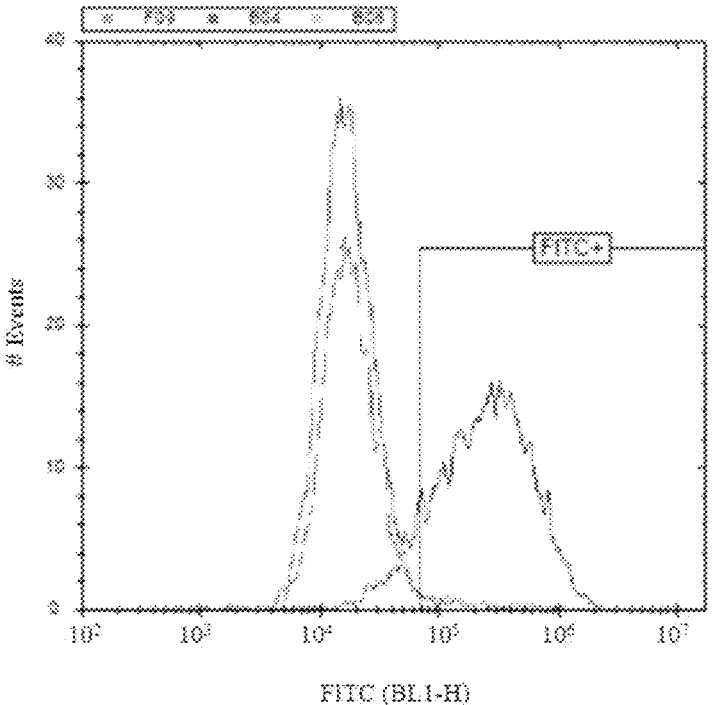
FIG. 1 shows the identification results of antigen express-ing cell lines by flow cytometry, in which panel 1A: HT-1376 bladder cancer cells; panel 1B: CHO-huNectin4 S8 cells.
Figure 1:
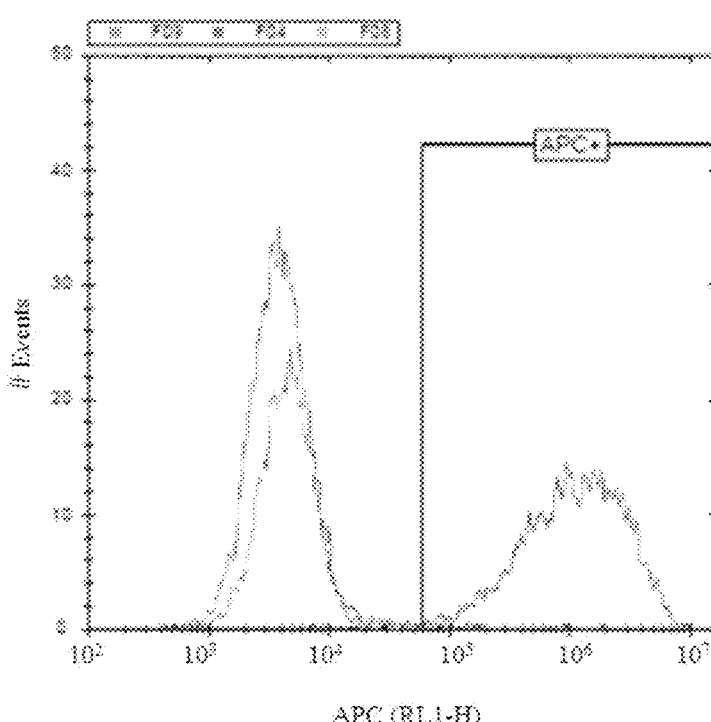

The high expression clone S8 was named as CHO-huNectin4 S8. Identification results of the cells compared with HT-1376 bladder cancer cells endogenously expressing Nectin-4 are shown in FIG. 1.

Example 3 Screening and Identification of Hybridoma Cells

1. Immunization of Mice

10 Balb/c mice aged 8 weeks were grouped into two groups, and immunized respectively with a traditional immunization procedure which utilized the engineered CHO-huNectin4 S8 cell line as an immunizing agent, and a rapid immunization procedure which utilized recombinant human Nectin4 protein (purchased from Novoprotein Sci-entific. Inc, Cat: CJ19) as an immunizing agent.

Blood sampled from the mice before immunization were used as negative control. The two immunizing agents were intraperitoneally injected, and the second and third immu-nizations were performed at an interval of 2 weeks. Blood was collected one week after the third immunization, and serum was tested for titers. Mice with high titers were selected to receive final boost 3 days before the fusion.

2. Fusion and Screening

SP20 myeloma cells were recovered and expanded to a certain order of magnitude. The cells were provided with fresh medium one day before fusion to ensure a good growth state of cells for the fusion. Myeloma cells were collected on the day of the fusion, centrifuged, suspended in a basal medium, and counted for use.

Respectively, spleens and lymph nodes of the mice were taken aseptically, and ground to prepare cell suspensions, which were then filtered through cell filters. Red blood cell lysing was performed and the obtained suspensions were pooled and cells therein were counted. B cells and SP20 myeloma cells were mixed at a ratio of 1:2, and the mixed cells were centrifuged, washed twice with electrofusion buffer, and re-suspended to obtain a cell density adjusted to about $1\text{-}2\times10^7/\text{ml}$. The cell suspension was added into an electric shock cup for fusion, and added into a complete culture medium, and placed into an incubator at 37° C., 8% $CO_2$ for recovery for 30-240 minutes. Afterwards, the cells were added into HAT culture medium, and plated into 384-well plates for culture. The cells were replenished with the HAT culture medium on the 5th day, and the HAT culture medium was replaced with HT culture medium on the 7th day. On the 8th-10th day, screening for positive hybridomas were performed as follows.

Culture supernatants of the hybridoma cells were taken and analyzed by FACS assay, and positive wells in which the cells were able to bind to CHO-huNectin4 S8 cells which stably expressed human Nectin4 antigen on the cell surface and unable to bind to blank CHOK1 cells were screened. Single cells in the screened positive wells were obtained by limiting dilution; and, when the cells obtained after two successive subclonings were detected 100% positive, sub-cloning operation was ended. Each of the hybridoma cell clones obtained secreted only one antibody.

Figure 2B:
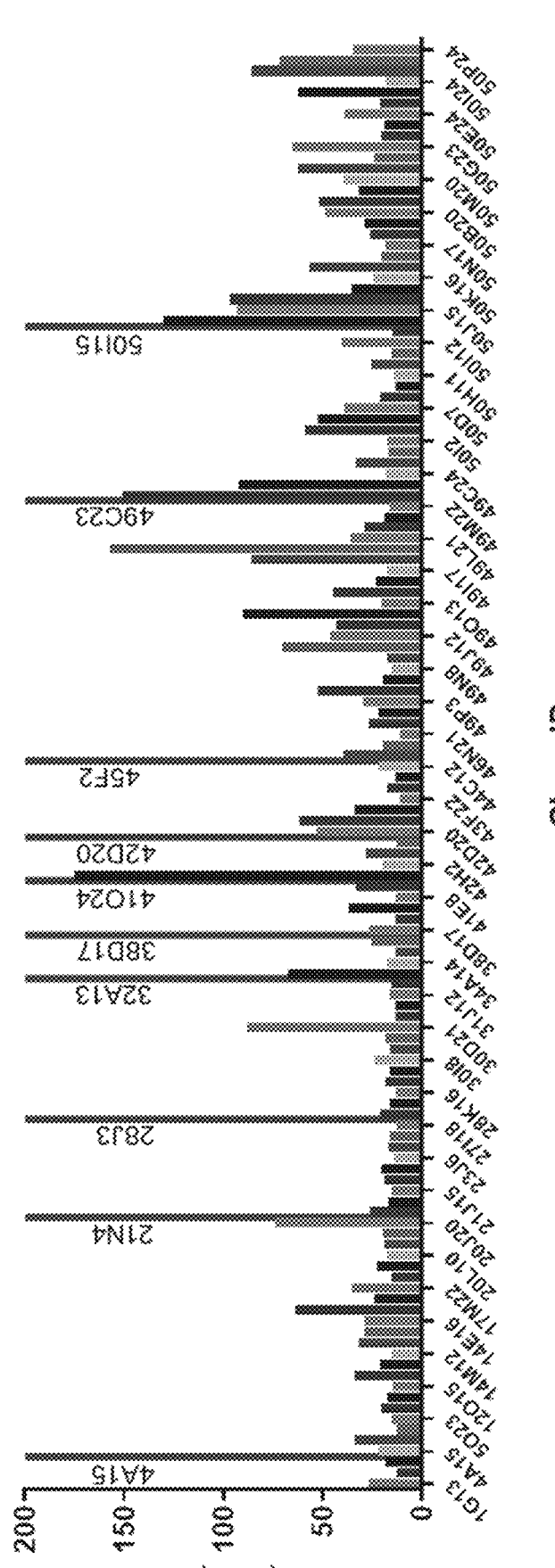
FIG. 2 shows the detection results of the binding activity of hybridoma cell culture supernatants by FACS assay, in which panel 2A: the first round of screening; panel 2B: the second round screening.
Figure 2C:
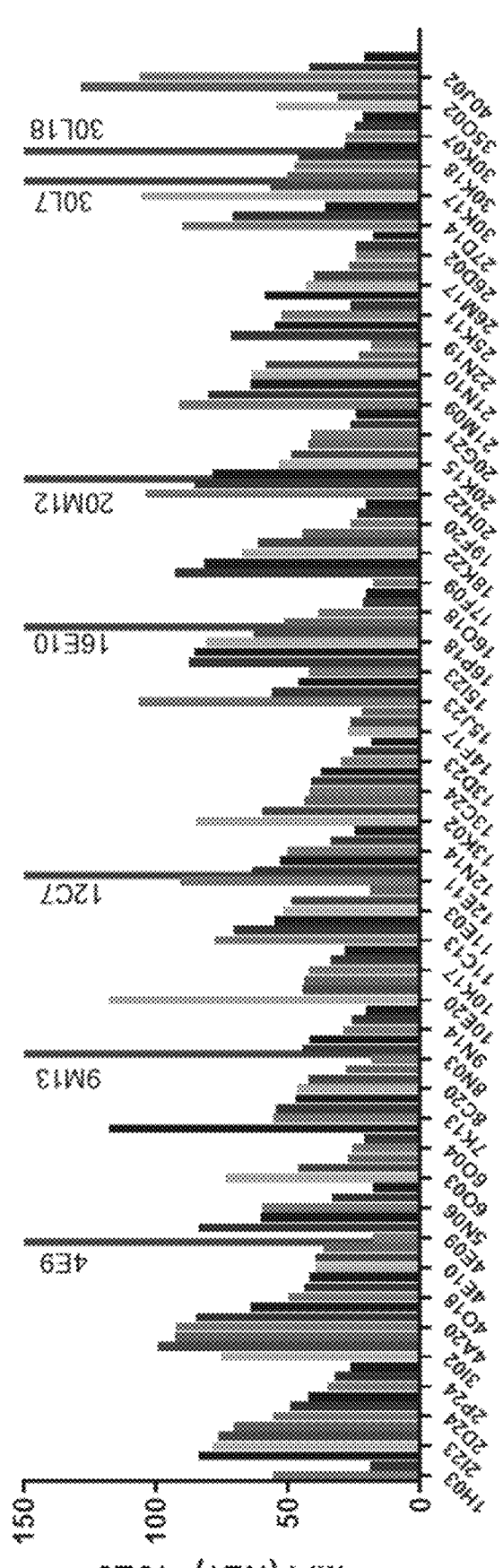

The detection results of the binding activity of hybridoma cell culture supernatants by FACS assay were shown in FIG. 2 and Table 1 to Table 3.

TABLE 1

| Clones selected after the first round of screening | | |
|---|---|---|
| ID | FACS | FACS ($\times 10^5$) |
| 5M21 | 1731598.512 | 173.1599 |
| 7I18 | 900458.7143 | 90.04587 |
| 26G13 | 493254.2857 | 49.32543 |
| 29B12 | 685057.4296 | 68.50574 |
| 30J3 | 440992.4 | 44.09924 |

TABLE 2

| Clones selected after the second round of screening | | |
|---|---|---|
| ID | FACS | FACS ($\times 10^5$) |
| 4A15 | 221093.1035 | 22.1 |
| 21N4 | 264347.4081 | 26.4 |
| 28J3 | 208131.2025 | 20.8 |
| 32A13 | 677419.4598 | 67.7 |
| 38D17 | 266536.8786 | 26.7 |
| 41O24 | 1749182.695 | 174.9 |
| 42D20 | 533378.824 | 53.3 |
| 45F2 | 393898.7755 | 39.4 |
| 49C23 | 1510386.33 | 151.0 |
| 50I15 | 1299424.85 | 129.9 |

TABLE 3

| Clones selected after the third round of screening | | |
|---|---|---|
| ID | FACS | FACS ($\times 10^5$) |
| 4E9 | 180199.602 | 180.199 |
| 9M13 | 448161.147 | 44.816 |
| 12C7 | 639255.386 | 63.926 |
| 16E10 | 515026.703 | 51.503 |
| 20M12 | 783128.784 | 78.313 |
| 30L7 | 505457.216 | 50.546 |
| 30L18 | 284554.941 | 28.455 |

The obtained murine monoclonal antibodies were named after IDs of the hybridoma cell lines.

Example 4 Identification of Variable Region Sequences of Murine Monoclonal Antibodies The monoclonal hybridoma cells secreting anti-human Nectin-4 antibodies were subject to expansion culture, and total RNA of the cells was extracted using RNAfast200 Kit (Shanghai Flytech Biotechnology Co., Ltd.) according to the steps described in the instructions provided in the kit; the total RNA of the hybridoma cells obtained was reverse transcribed to cDNA using 5×PrimeScript RT Master Mix (Takara); and sequences of antibody light chain variable region IgVL (κ) and heavy chain variable region VH were amplified using degenerate primers (Anke Krebber, 1997) and Extaq PCR reagents (Takara). PCR amplification products were purified using PCR clean-up Gel Extraction Kit (Macherey-Nagel GmbH & Co.); and linked to T-vector using pClone007 Simple Vector Kit (Tsingke Biotechnology Co., Ltd.) according to the instructions provided in the kit, and transformed into competent *Escherichia coli* cells. Variable region sequences of the monoclonal antibodies were obtained by DNA sequencing after strain amplification and plasmid extraction.

Example 5 Preparation of Chimeric Antibodies

The heavy chain variable region sequence of each murine anti-human Nectin-4 monoclonal antibody and the heavy chain constant region sequence of published human mono-clonal antibody IgG1 subclass (SEQ ID NO: 4) were spliced together and constructed into a mammalian cell expression vector; and the light chain variable region sequence of each murine anti-human Nectin-4 monoclonal antibody and the light chain constant region sequence of published human monoclonal antibody kappa subclass (SEQ ID NO: 5) were spliced together and constructed into a mammalian cell expression vector. The constructed heavy chain and light chain vectors of anti-human Nectin-4 chimeric antibodies were mixed in pairs, and HEK293 cells were transfected with the vectors using Polyethyleneimine (PEI). Cell super-natants were collected about 7 days later, and anti-human Nectin-4 chimeric antibody proteins were obtained through MabSelect.

The chimeric antibodies obtained were named following a format "murine antibody abbreviation-xiIgG".

Example 6 Humanization of Murine Antibodies and Preparation of Humanized Antibodies Based on a comprehensive analysis of antibody coding schemes, amino acid sequence regions of 6 complementar-ity-determining regions (CDRs) and framework regions supporting the conserved three-dimensional conformation in the heavy and light chains of each murine antibody were determined. Subsequently, the heavy chain variable region sequence of the human antibody which mostly resembles a murine antibody was searched for in known human antibody sequences, such as IGHVI|IGHJ4*01, and then the frame-work region sequences in the sequence were selected as a template, and the heavy chain CDRs of the murine antibody were combined with the framework regions of the human antibody, and a humanized heavy chain variable region sequence was ultimately produced. In the same manner, a humanized light chain variable region sequence was pro-duced.

An Antibody with murine CDRs grafted directly to its human framework regions often exhibits a dramatic decrease in binding activity, thus requiring the conversion of individual amino acids in the framework regions from being human back to murine. In order to determine which posi-tions need to be reverted to original murine residues, the designed humanized antibody sequence and the original murine antibody sequence should be compared to check for differences in the amino acids, and to check whether those different amino acids are important for supporting the anti-body structure or for binding to the antigen. The sequences obtained by humanization design need to be checked for potential post-Translational Modification Sites, such as an N (asparagine) glycosylation site, an N-deamidation site, a D (aspartic acid) isomerization site, etc.

The humanized antibodies were obtained by combining the humanized heavy and light chain variable regions, and referring to the procedure as described in Example 5 for the preparation of chimeric antibodies. The humanized antibodies were named following a format "murine antibody abbreviation-hzmn", in which m and n were the numbers of engineered humanized sequences of VH and VL of murine antibodies (VH_hz and VL_hz), respectively.

Example 7 Preparation of Antibody-Drug Conjugates (ADCs)

An antibody was reduced in PBS, pH 7.4 with 2.0-2.6 equivalent amounts of TECP for 2 hours, and a solution of DMA containing vcMMAE was added into the solution of TECP-reduced antibody (at a molar ratio of 6:1 of vcMMAE to the antibody). After stirring for 1 hour at 2-8° C., DMA and small molecule residues were removed by ultrafiltration. Absorbance at 248-280 nm of the conjugate was measured using an ultraviolet spectrophotometer, and concentration of the conjugate was calculated. Conjugates obtained were subpackaged into freezing tubes for preservation at –80° C.; and DAR values of the conjugates (4.0±1) were determined by HPLC-HIC.

An ADC was named as the name of the corresponding antibody added with a suffix "E".

Example 8 In Vitro Cell Binding Assay

Anti-human Nectin-4 control antibody Enfortumab, and antibodies or ADCs of the present disclosure were diluted 2-fold in gradient from an initial concentration of 100 nM and solutions of each antibody or ADC of 16 concentrations were obtained totally. The solutions of different concentrations were added to 384-well plates, 10 μl per well.

BT474 cells (breast cancer cells) expressing Nectin-4 on the cell surface were collected by centrifugation at 100 g at room temperature for 5 minutes, and then the cells were washed with PBS containing 0.5% BSA once and were centrifuged at 100 g at room temperature for 5 minutes. The cells were resuspended at a density of about 2×10⁶ cells/ml, and 10 μl were added to each well of the 384-well plates which the antibodies or ADCs had been added into. After incubation at 4° C. for 1 hour, fluorescently labeled goat anti-human IgG secondary antibody was added. After continued incubation at 4° C. for 1 hour, mean fluorescence readings of the cell populations were analyzed by a flow cytometer.

Figure 3:
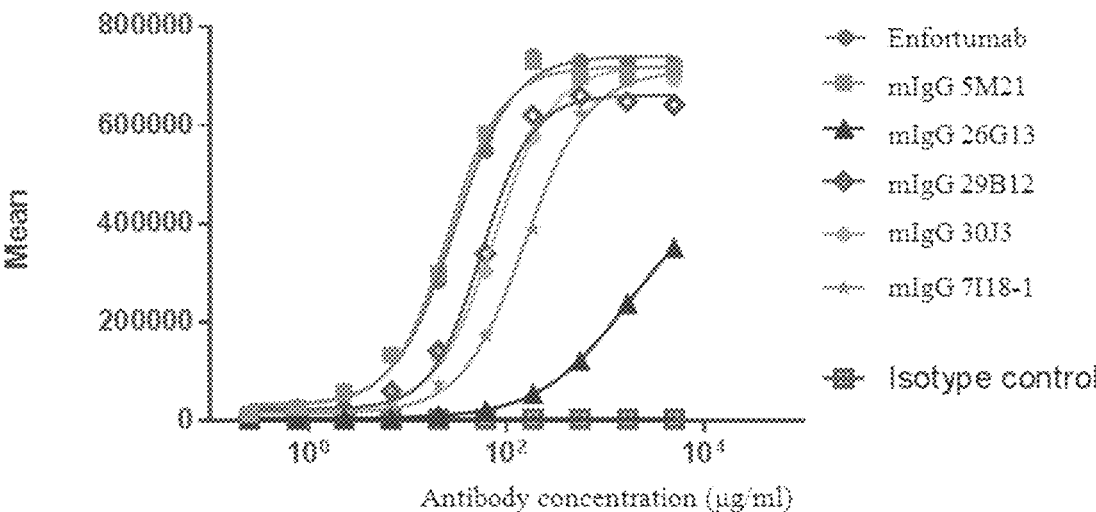
FIG. 3 shows the experiment results of the binding of antibodies to BT474 cells by FACS assay.
Figure 3:
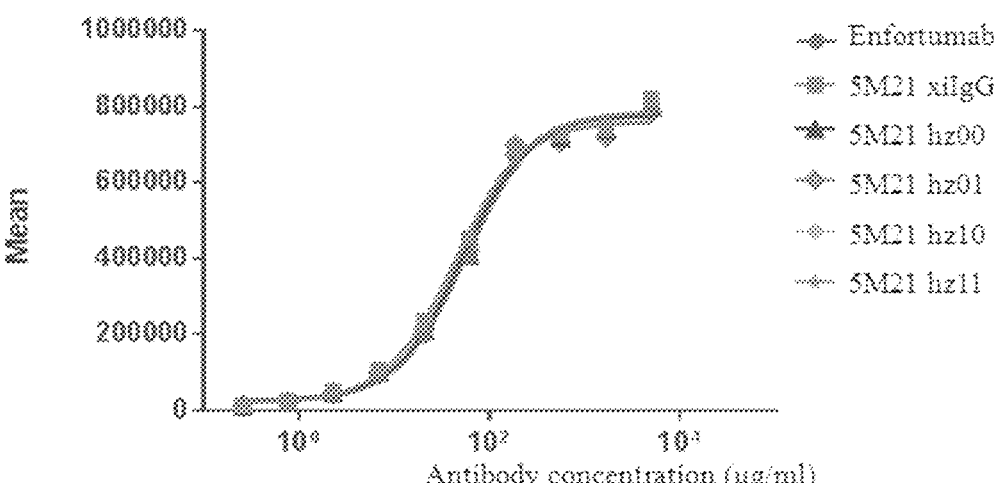
Figure 3C:
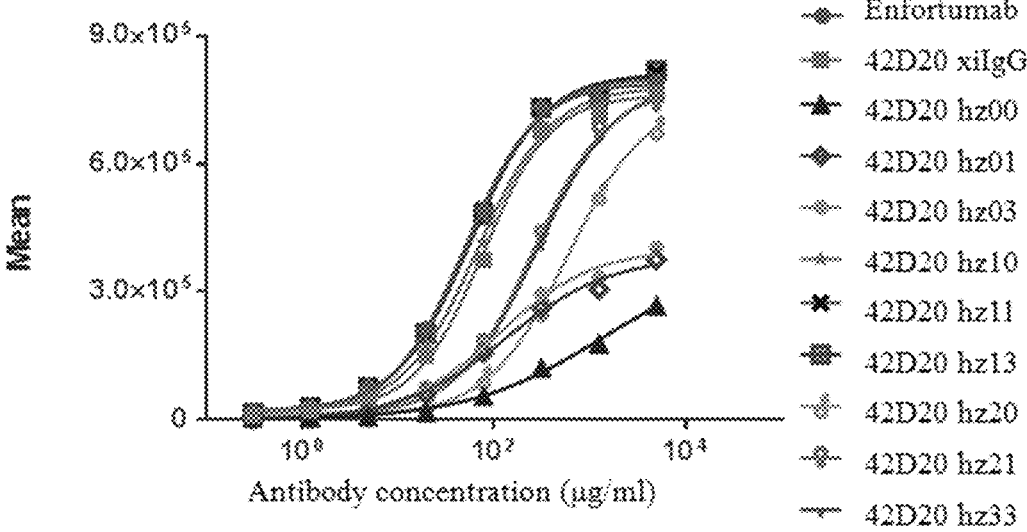
Figure 3D:
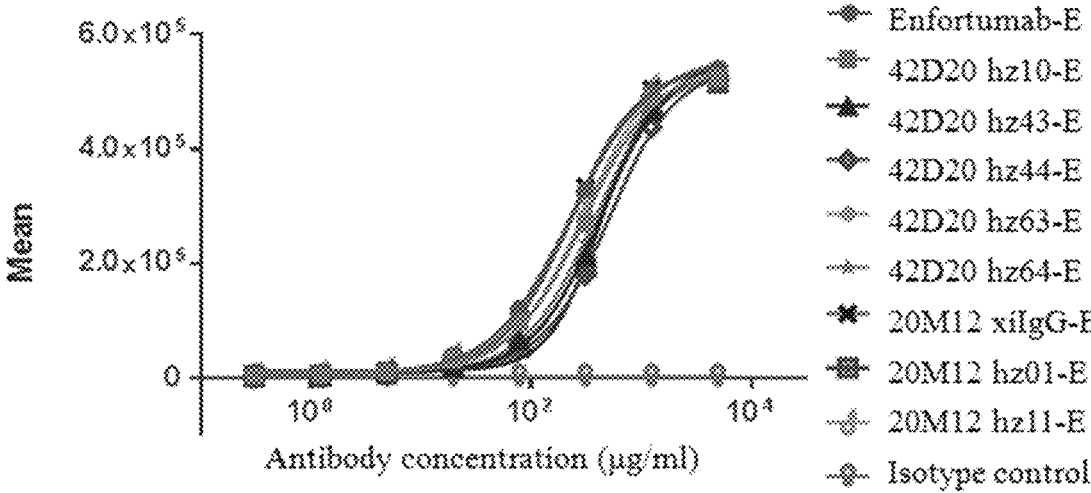

The experiment results of the binding of murine antibody molecules of the present disclosure to BT474 cells by FACS assay are shown in panel 3A in FIG. 3 and Tables 4 and 5.

TABLE 4

Binding of murine monoclonal antibodies to BT474 cells

|  | EC50 (μg/ml) |
| --- | --- |
| Enfortumab | 29.60 |
| mIgG 5M21 | 25.44 |
| mIgG 26G13 | 1657 |
| mIgG 29B12 | 56.45 |
| mIgG 30J3 | 75.00 |

14

TABLE 4-continued

Binding of murine monoclonal antibodies to BT474 cells

|  | EC50 (μg/ml) |
| --- | --- |
| mIgG 7I18 | 154.8 |
| Isotype control | — |

TABLE 5

Binding of murine monoclonal antibodies to BT474 cells

|  | EC50 (μg/ml) |
| --- | --- |
| Enfortumab | 98.79 |
| mIgG 4E9 | 480.3 |
| mIgG 30L18 | 422.6 |
| mIgG 20M12 | 83.79 |
| mIgG 9M13 | 178.5 |
| Isotype control | — |

The experiment results of the binding of engineered humanized molecules of the present disclosure to BT474 cells by FACS assay are shown in panels 3B and 3C in FIG. 3 and Tables 6 and 7.

TABLE 6

Binding of humanized antibodies to BT474 cells

|  | EC50 (μg/ml) |
| --- | --- |
| Enfortumab | 57.21 |
| 5M21 xiIgG | 46.07 |
| 5M21 hz00 | 52.18 |
| 5M21 hz01 | 48.12 |
| 5M21 hz10 | 44.31 |
| 5M21 hz11 | 44.48 |

TABLE 7

Binding of humanized antibodies to BT474 cells

|  | EC50 (μg/ml) |
| --- | --- |
| Enfortumab | 50.33 |
| 42D20 xiIgG | 77.01 |
| 42D20 hz00 | 1344 |
| 42D20 hz01 | 131.9 |
| 42D20 hz02 | 111.6 |
| 42D20 hz03 | 67.59 |
| 42D20 hz10 | 52.75 |
| 42D20 hz11 | 56.06 |
| 42D20 hz13 | — |
| 42D20 hz20 | — |
| 42D20 hz21 | 284.90 |
| 42D20 hz23 | 50.33 |

The experiment results of the binding of ADCs of the present disclosure to BT474 cells by FACS assay are shown in panel 3D in FIG. 3 and Table 8.

TABLE 8

Binding of antibody-drug conjugates to BT474 cells

|  | EC50 (μg/ml) |
| --- | --- |
| Enfortumab-E | 229.8 |
| 42D20 hz10-E | 306.7 |
| 42D20 hz43-E | 430.1 |
| 42D20 hz44-E | 504.5 |
| 42D20 hz63-E | 298.7 |

TABLE 8-continued

| Binding of antibody-drug conjugates to BT474 cells | |
|---|---|
| | EC50 (μg/ml) |
| 42D20 hz64-E | 373.4 |
| 20M12 xiIgG-E | 226.7 |
| 20M12 hz01-E | 419.9 |
| 20M12 hz11-E | 231.7 |
| Isotype control | — |

Example 2 In Vitro Cytology Assays of Antibodies

9.1 Endocytosis Assay in BT474 Cells

1. BT474 cells were collected by centrifuged at 1200 rpm for 8 minutes, and washed twice with DPBS (Gibco, Cat.: 14190-136).

2. 1E5 cells per well were seeded; and each antibody or ADC was diluted 2-fold in gradient from an initial concentration of 10 μg/ml and solutions of each antibody or ADC of 7 concentrations were obtained totally, in which the last one concentration was indeed used for a blank well. Solutions of the antibodies and ADCs were added into the cells and mixtures obtained were incubated on ice for 1 hour.

3. The cells were washed twice with ice-cold PBS, and centrifuged at 1200 rpm for 8 minutes. Next, the cells were resuspended in RPMI 1640 medium supplemented with L-glutamine and HEPES and divided into 3 portions in equal volumes, one of which was incubated at 37° C. for different time periods, one of which was kept on ice always to be used as a 0 time point control without endocytosis, while one of which without antibody or ADC added in was used as an NC control.

4. The cells were washed with citric acid (pH 2.7) for 3.5 minutes, neutralized with 1 M Tris-HCl solution (pH 9.5), wash twice with PBS, and resuspended in appropriate amounts of 1% BSA-PBS; and then detected on Instrument IQplus.

5. Data was analyzed and processed using software GraphPad Prism.

Figure 4:
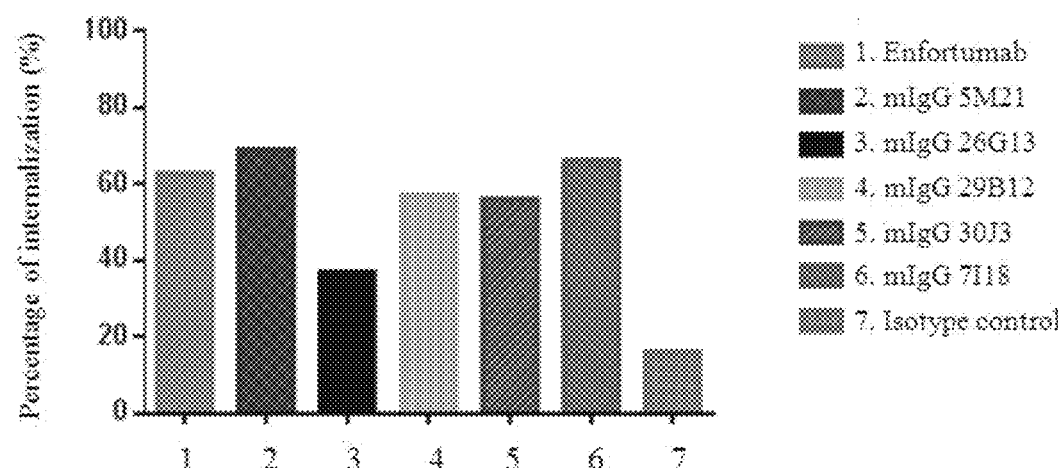
FIG. 4 shows the experiment results of endocytic activity of antibodies in BT474 cells.
Figure 4:
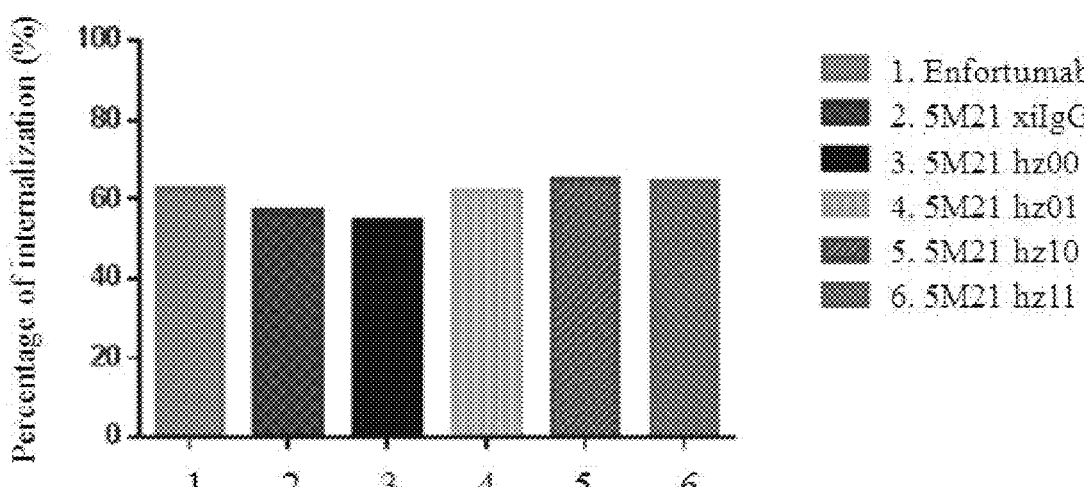
Figure 4C:
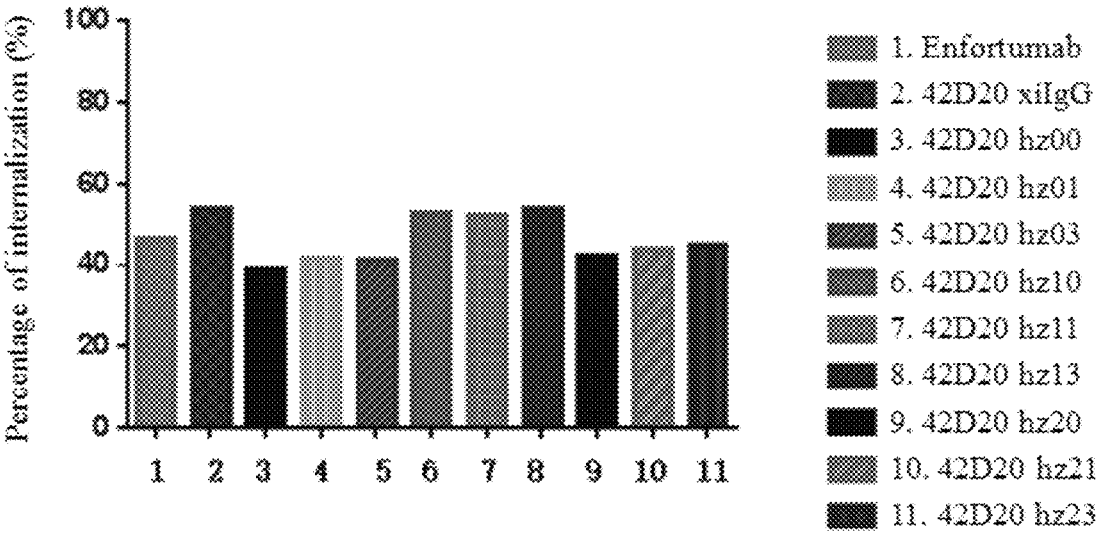
Figure 4D:
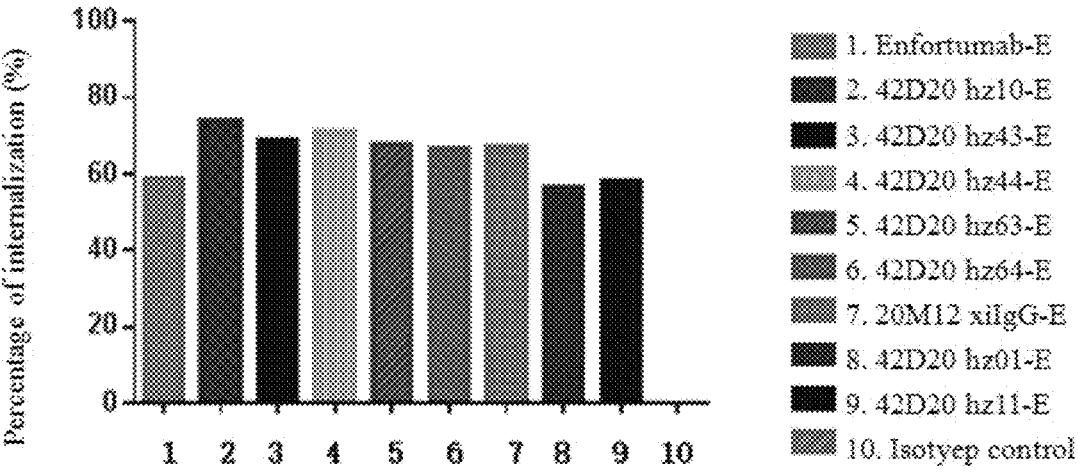

The experiment results of the endocytic activity of murine antibody molecules of the present disclosure in BT474 cells are shown in panel 4A in FIG. 4 and Table 9.

TABLE 9

| Endocytic activity of murine monoclonal antibodies in BT474 cells | |
|---|---|
| | Endocytosis efficiency (%) |
| Enfortumab | 63 |
| mIgG 5M21 | 69 |
| mIgG 26G13 | 37 |
| mIgG 29B12 | 57 |
| mIgG 30J3 | 56 |
| mIgG 7I18 | 66 |
| Isotype control | 16 |

The experiment results of the endocytic activity of engineered humanized molecules of the present disclosure in BT474 cells are shown in panels 4B and 4C in FIG. 4 and Tables 10 and 11.

TABLE 10

| Endocytic activity of humanized antibodies in BT474 cells | |
|---|---|
| | Endocytosis efficiency (%) |
| Enfortumab | 62.4 |
| 5M21 xiIgG | 56.9 |
| 5M21 hz00 | 54.8 |
| 5M21 hz01 | 62.2 |
| 5M21 hz10 | 64.8 |
| 5M21 hz11 | 64.4 |

TABLE 11

| Endocytic activity of humanized antibodies in BT474 cells | |
|---|---|
| | Endocytosis efficiency (%) |
| Enfortumab | 46.6 |
| 42D20 xiIgG | 54 |
| 42D20 hz00 | 39.1 |
| 42D20 hz01 | 41.5 |
| 42D20 hz03 | 41.1 |
| 42D20 hz10 | 52.7 |
| 42D20 hz11 | 52.5 |
| 42D20 hz13 | 53.8 |
| 42D20 hz20 | 42 |
| 42D20 hz21 | 43.9 |
| 42D20 hz23 | 45 |

The experiment results of the endocytic activity of ADCs of the present disclosure in BT474 cells are shown in panels 4D in FIG. 4 and Table 12.

TABLE 12

| Endocytic activity of antibody-drug conjugates in BT474 cells | |
|---|---|
| | Endocytosis efficiency (%) |
| Enfortumab-E | 58.9 |
| 42D20 hz10-E | 74 |
| 42D20 hz43-E | 68.9 |
| 42D20 hz44-E | 71.1 |
| 42D20 hz63-E | 67.9 |
| 42D20 hz64-E | 66.6 |
| 20M12 xiIgG-E | 67 |
| 20M12 hz01-E | 56.6 |
| 20M12 hz11-E | 58.4 |
| Isotype control | — |

9.2 Proliferation Inhibition Assay in BT474 Cells

Breast cancer BT474 cells expressing Nectin4 were cultured, harvested by trypsinization, centrifuged at 400 g for 5 minutes, and supernatant was discarded. Then the cells were plated at a density of 4000 cells per well, and cultured at 37° C., 5% $CO_2$ for 24 hours. Antibodies or ADCs to be tested were dissolved in a medium containing 1% BSA, and diluted 3-fold in gradient from an initial concentration of 200 μg/ml respectively and solutions of each antibody or ADC of 9 concentrations were obtained totally, including zero concentration. The diluted solutions of antibodies or ADCs were added into 96-well plates, 100 μl per well, and then 100 μl of the cell culture were added to each well containing the solutions of antibodies or ADCs, and mixed, incubated at 37° C., 5% $CO_2$ for 120 hours. CCK-8 at a concentration of 5 μM was prepared using the medium containing 1% BSA, and 20 μl of the CCK-8 solution were added to each well of the 96-well plates which then were incubated at 37° C., 5% $CO_2$ for 4 hours. Finally, the plates were placed at room temperature for 15 minutes and then mixed well. The plates were read with 450 nm as detection wavelength. Fourparameter fitting was performed using SoftMax Pro with working concentrations (ng/ml) of naked antibodies or ADCs plotted on X axis and measured absorbance values plotted on Y axis, and EC50 values of the naked antibodies and the ADCs were obtained.

The results are shown in Tables 13, 14 and 15.

TABLE 13

Inhibition activity of murine antibodies on the proliferation of BT474 cells

|  | EC50 (ng/ml) | Percentage of cell killing at the highest concentration |
|---|---|---|
| Enfortumab | 3.367 | 43.3% |
| mIgG 5M21 | 42.34 | 33.5% |
| mIgG 29B12 | 387.0 | 33.2% |
| mIgG 30J3 | 16.88 | 52.8% |
| Isotype control | N/A | N/A |

TABLE 14

Inhibition activity of ADCs on the proliferation of BT474 cells

| Plate no. | Sample | EC50 (ng/ml) | Percentage of cell killing at the highest concentration |
|---|---|---|---|
| Plate 1 | Enfortumab-E | 5.366 | 46.7% |
|  | mIgG 5M21-E | 3.208 | 36.0% |
|  | Isotype control | N/A | N/A |
| Plate2 | Enfortumab-E | 3.946 | 36.4% |
|  | 5M21 hz10-E | 21.07 | 29.4% |
|  | 5M21 hz11-E | 4.45e+26 | 38.5% |
| Plate3 | Enfortumab-E | 5.111 | 41.5% |
|  | mIgG 42D20-E | 4.644 | 33.5% |
|  | 42D20 hz10-E | 2.606 | 33.7% |
| Plate4 | Enfortumab-E | 5.299 | 37.8% |
|  | 42D20 hz11-E | 4.411 | 31.8% |
|  | 42D20 hz13-E | 4.373 | 32.1% |

TABLE 15

Inhibition activity of ADCs on the proliferation of BT474 cells

| Plate no. | Sample | EC50 (ng/ml) | Percentage of cell killing at the highest concentration |
|---|---|---|---|
| Plate1 | Enfortumab-E | 2.257 | 45.2% |
|  | 20M12 hz01-E | 24.21 | 32.2% |
|  | 20M12 hz11-E | 31.60 | 38.3% |
| Plate2 | Enfortumab-E | 3.858 | 46.1% |
|  | 20M12 xiIgG-E | 14.78 | 41.4% |
|  | 42D20 hz43-E | 6.310 | 42.5% |
| Plate3 | Enfortumab-E | 2.908 | 47.2% |
|  | 42D20 hz44-E | 3.611 | 42.7% |
|  | 42D20 hz63-E | 2.419 | 47.0% |
| Plate4 | Enfortumab-E | 3.166 | 44.9% |
|  | 42D20 hz64-E | 4.581 | 40.9% |
|  | 42D20 hz10-E | 9.406 | 40.8% |

Figure 5:
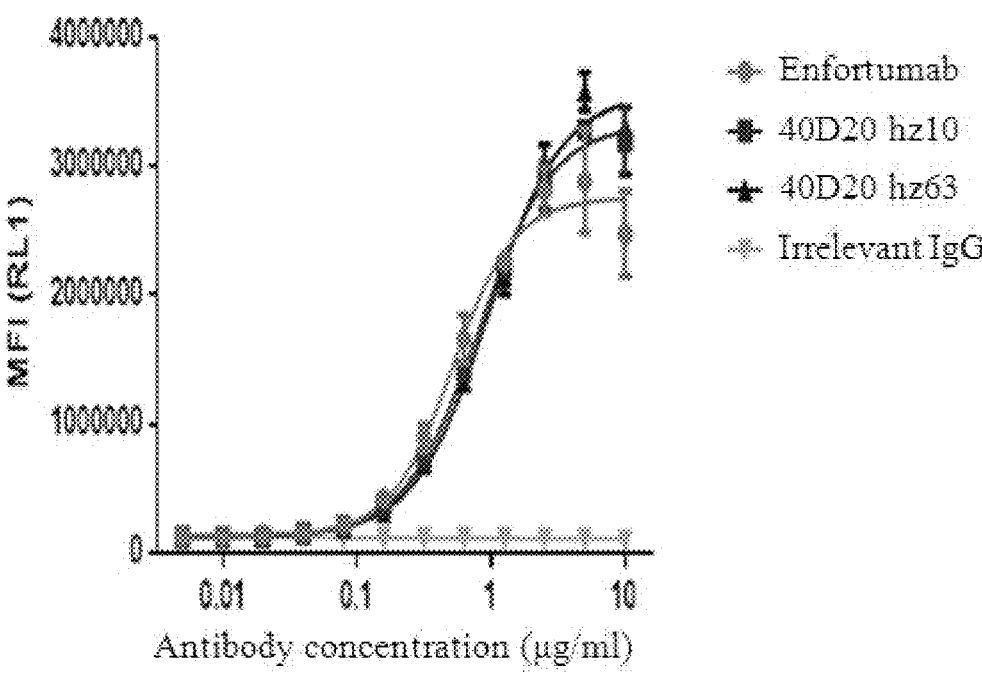
FIG. 5 shows the experiment results of the binding of antibodies to huNectin4, muNectin4, and cynoNectin4 expressing cells by FACS assay.
Figure 5:
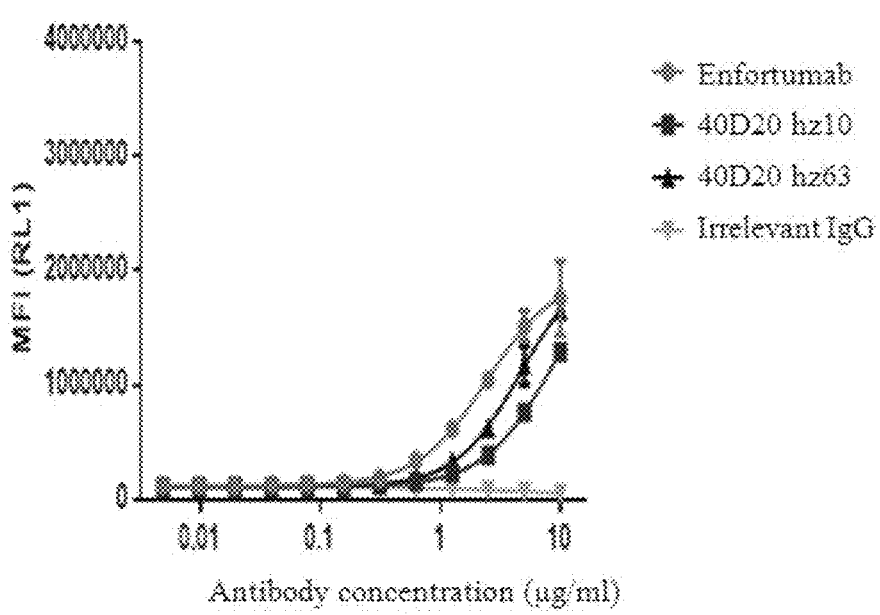
Figure 5C:
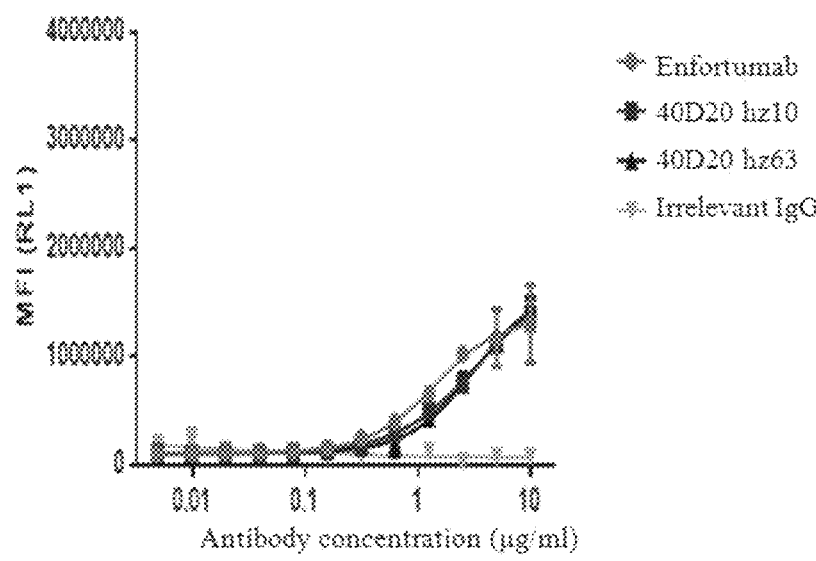

Example 10 Analysis of Cross-Binding Activity of Antibodies to Antigens—Facs Cells CHO-huNectin4 S8;
HEK293 cells expressing murine Nectin4 (NP_082169): HEK-muNectin4; and
HEK293 cells expressing Cyno Nectin4 (SEQ ID NO: 6): HEK-cynoNectin4.
This experiment was performed by referring to the procedure as described in Example 8. The results are shown in panels 5A, 5B, and 5C in FIG. 5 and Tables 16, 17, and 18.

TABLE 16

Binding of humanized antibodies to CHO-huNectin4 S8 cells

|  | EC50 (μg/ml) |
|---|---|
| Enfortumab | 0.5134 |
| 42D20 hz10 | 0.8013 |
| 42D20 hz63 | 0.9462 |
| Irrelevant IgG | — |

TABLE 17

Binding of humanized antibodies to HEK-muNectin4 cells

|  | EC50 (μg/ml) |
|---|---|
| Enfortumab | 2.432 |
| 42D20 hz10 | 8.745 |
| 42D20 hz63 | 4.704 |
| Irrelevant IgG | — |

TABLE 18

Binding of humanized antibodies to HEK-cynoNectin4 cells

|  | EC50 (μg/ml) |
|---|---|
| Enfortumab | 0.9480-2.073 |
| 42D20 hz10 | 2.423-4.967 |
| 42D20 hz63 | 2.448-4.058 |
| Irrelevant IgG | — |

Example 11 Assay of In Vitro Binding Affinity and Kinetics of Antibodies

Interactions between the antibodies and the antigen were measured using a BIAcore instrument S200 from GE. Referring to the instructions provided in Biotin Capture Kit from GE Healthcare, the analytical channel and the control sample channel on CAP sensor chip were first coupled with antigen i.e. His-tagged human NECTIN4, then samples containing antibodies (diluted 3-fold from an initial concentration of 20 nM respectively and solutions of each antibody of 8 concentrations were obtained totally, and the concentration 0.741 nM was set to be repeated) were allowed to flow through both the analytical channel and the sample channel, and the photoreactions upon antibody-antigen binding were measured. Association constant Kon and dissociation constant Koff and affinity constant KD of each antibody were finally obtained by instrument software fitting (1:1 binding mode) analysis.

The results are shown in Table 19.

TABLE 19

Results of binding affinity and kinetics of antibodies

|  | ka (1/Ms) | kd (1/s) | KD (M) |
|---|---|---|---|
| Enfortumab | 1.12E+06 | 5.52E−03 | 4.94E−09 |
| 42D20 xiIgG | 7.90E+05 | 7.98E−04 | 1.01E−09 |
| 42D20 hz10 | 8.31E+05 | 9.46E−04 | 1.14E−09 |
| 42D20 hz11 | 1.19E+06 | 1.15E−03 | 9.60E−10 |
| 42D20 hz13 | 1.19E+06 | 1.08E−03 | 9.04E−10 |
| 42D20 hz63 | 8.73E+05 | 1.57E−03 | 1.80E−09 |

Example 12 Validation of Cross-Binding Activity of Antibodies to Antigen Proteins Belong to the Same Family Antigens:
human Nectin-1 (C-6His), Novoprotein Cat #C492;
human Nectin-2 (C-6His), Novoprotein Cat #C440;
human Nectin-3 (C-6His), Novoprotein Cat #C630;
human Nectin-4 (C-6His), Novoprotein Cat #CJ19.
Antibodies (Primary Antibody): Antibodies of the Present Disclosure.
Control Antibodies:
CD111/Nectin-1/PVRL1 Antibody, Rabbit Fab, 80244-RP01-100, Sino biologics;
Anti-Nectin 2 antibody (ab233085), Rabbit antibody, Abcam;
Anti-Nectin 3 antibody (ab137961), Rabbit antibody, Abcam.
Secondary Antibody:
Goat anti-Rabbit IgG-Fc Secondary antibody (HRP) Cat #SSA003, Jackson Immuno.

Figure 6:
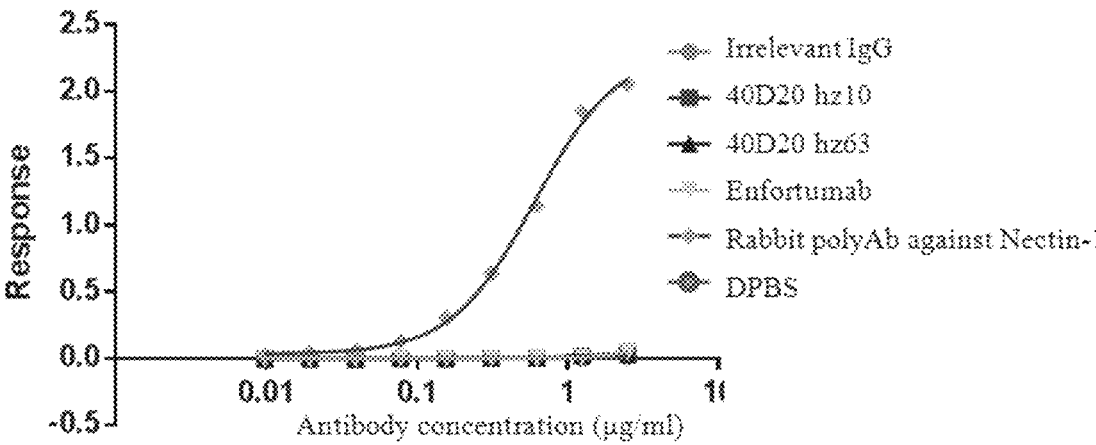
FIG. 6 shows the experiment results of the binding of antibodies to members of Nectin family, in which panel 6A: Nectin-1; panel 6B: Nectin-2; panel 6C: Nectin-3; panel 6D: Nectin-4.
Figure 6B:
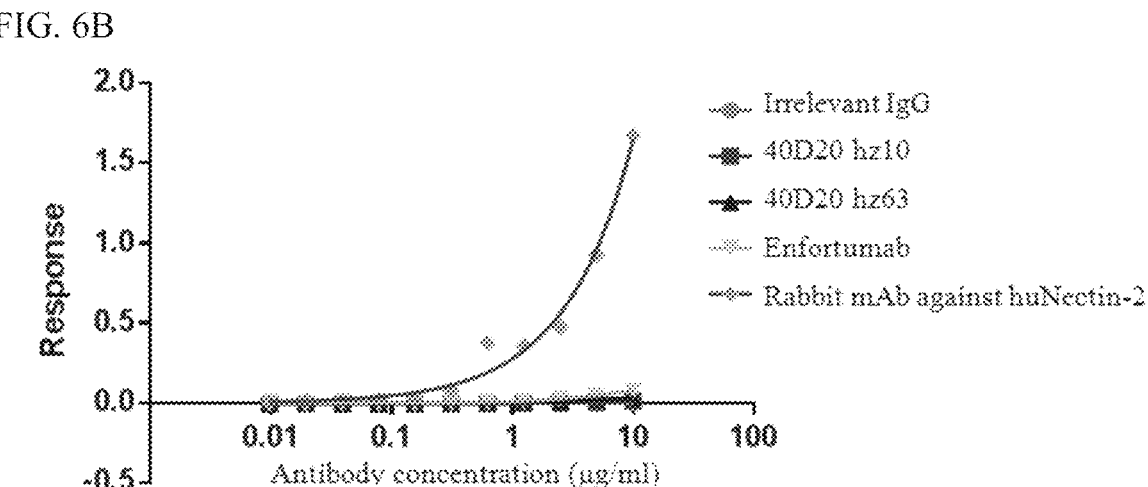
Figure 6C:
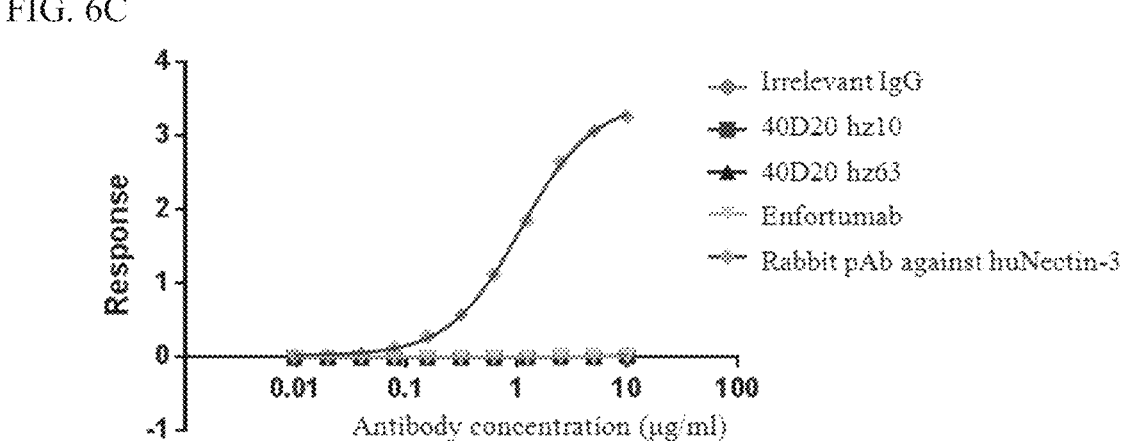
Figure 6D:
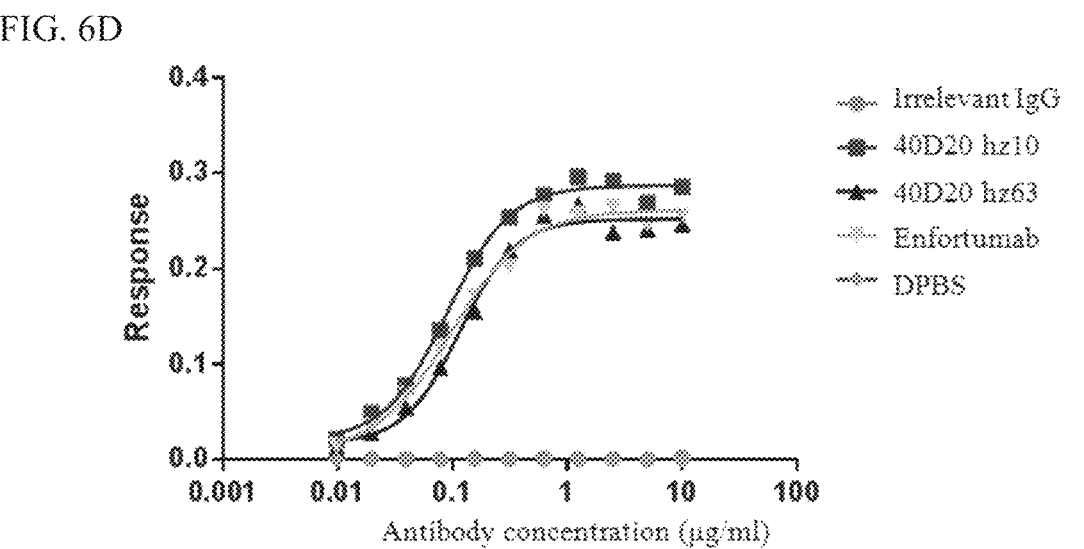

Plates were coated with 1 µg/ml of the antigens and incubated at 4° C. overnight; next, antibodies serially diluted were added into the plates. Finally, the HRP-labeled secondary antibody was added, and absorbance at 450 nm was detected. The results are shown in panels 6A, 6B, 6C and 6D in FIG. 6.

It can be seen from the results that the antibodies of the present disclosure exhibited properties consistent to those of the control antibodies: they all specifically recognized antigen Nectin-4, exhibited dose-dependent binding effects, and did not have cross-binding activity to other proteins belonging to the same family as Nectin-4.

Example 13 In Vitro Stability Study of Antibodies in Cyno Serum

Figure 7:
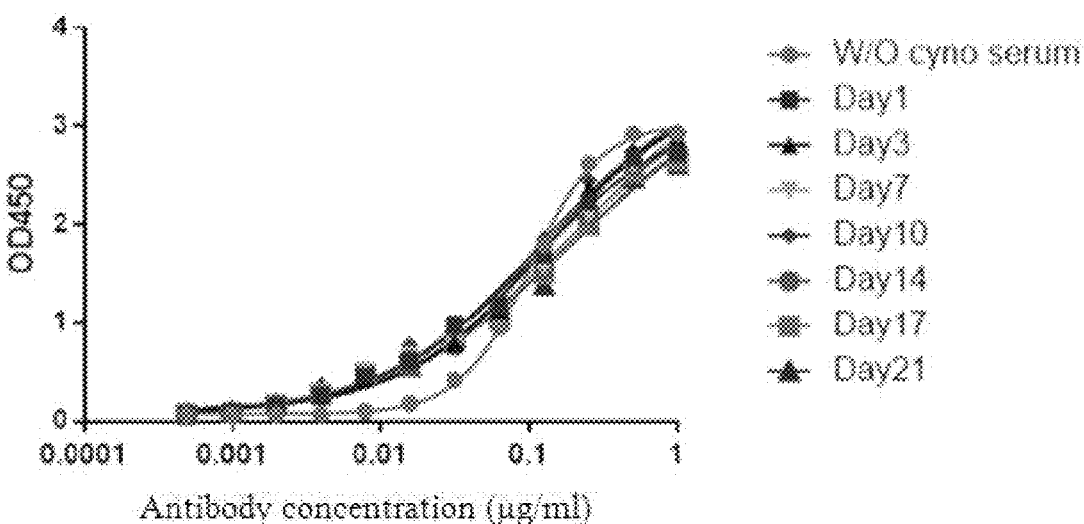
FIG. 7 shows the experiment results of stability of anti-bodies in cyno serum, in which panel 7A: control antibody, Enfortumab; panel 7B: 42D20 hz10.
Figure 7:
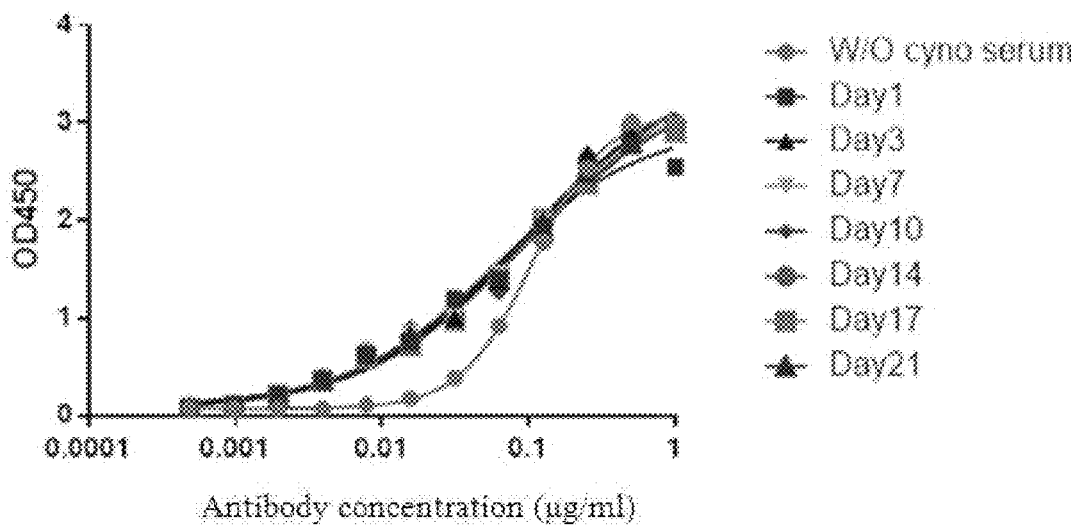

Experimental materials: antibodies to be tested, FBS, antigen to be bound by the antibodies, anti-huIgG Fab monoclonal antibody (Sigma, 15260-1ML), and HRP-labeled goat anti-human IgG secondary antibody (Jackson, code: 109-035-098).
Experimental Instrument: An Incubator at 37° C., and a Microplate Reader.
Experimental Procedure:
Sample Preparation:
1) Solution of an antibody to be tested was adjusted to a concentration of 20 µg/ml, filtered for sterilization, and subpackaged into 250 µl/tube for use;
2) Cyno serum of the same volume was added into the subpackaged antibody solution, to obtain a sample containing serum at a final concentration of 50% and an antibody at a final concentration of 10 µg/ml;
3) 7 such samples in total were prepared, sealed with sealing film, and placed at 37° C.; and during the whole process, the samples were kept sterile;
4) The samples were taken on day 0, 3, 7, 10, 14, and 21 respectively and placed at 4° C. for testing, in which the sample taken on day 21 was placed at 4° C. for at least one day.
Testing Method:
1) Two 96-well ELISA plates were coated with 0.2 µg/ml antigen in PBS and anti-IgG Fab monoclonal antibody in PBS respectively, 100 µl per well, at 4° C. overnight;
2) Reagents needed were prepared:
blocking buffer 5% BSA+PBS
antibody diluting buffer 5% BSA+PBS+50% FBS
ELISA plate washing buffer 0.1% Tween+PBS 3) The two coated ELISA plates were washed with 300 µl/well of PBS for 3 times, to wash uncoated antigen away;
4) the blocking buffer were added, 200 µl per well, to block the plates at 37° C. for 1 hour;
5) The antibody to be tested in each sample was diluted with the antibody diluting buffer to 2 µg/ml, and further diluted 3-fold in gradient and solutions of each antibody of 8 concentrations were obtained totally;
6) the blocking buffer in the two coated ELISA plates was poured off, and the diluted antibody solutions were added into the plates, 100 µl per well, which were then incubated at 37° C. for 1 hour;
7) The plates were washed with PBST for 3 times;
8) 1:5000 diluted secondary antibody were added into the washed ELISA plates, 100 µl per well, which were then incubated at RT for 40 minutes;
9) The plates were washed with PBST for 3 times;
10) TMB substrate were added, 100 µl per well, for color development in dark for 10 minutes;
11) 50 µl of 2 M HCl were added to stop reaction, and absorbance at 450 nm was read.
Data Processing:
Binding curves were plotted using ELISA values, to observe changes in the binding curves of the antibodies placed for different time periods and to evaluate the stability of the binding activity of the antibodies. The results are shown in panels 7A and 7B in FIG. 7.

The results prove that effective antibody contents did not change after the antibodies of the present disclosure had been incubated at 37° C. for 21 days, namely the antibodies can be stably stored at 37° C. for more than 21 days.

Example 14 Analysis of Pharmacokinetics of Antibodies in Mice

Experimental materials: antibodies to be tested, serum collected from mice at different time points, human Nectin-4 antigen to be bound by the antibodies, anti-huIgG Fab monoclonal antibody (Sigma, I5260-1ML), and HRP-labeled goat anti-human IgG secondary antibody (Jackson, code: 109-035-098).
Experimental Procedure:
Serum Collection:
1) Female Balb/C mice were grouped, 3 mice in group, and administered with 200 µg of the antibodies respectively via tail vein or intraperitoneally;
2) Blood from the tail vein was collected at different time points according to experiment design, and the blood samples collected were placed at room temperature for no less than 30 minutes; and then serum was separated by centrifugation at 4000 rpm for 15 minutes, and stored at –20° C. Given the last serum sample might evaporate during cryopreservation, the volume of the last serum sample of more than 20 µl should be collected;
3) the last serum sample collected should be cryopreserved at –20° C. for at least 24 hours.
Testing Method:
1) Two 96-well ELISA plates were coated with 0.2 µg/ml antigen in PBS and anti-IgG Fab monoclonal antibody in PBS respectively, 100 µl per well, at 4° C. overnight;
2) Reagents needed were prepared:
blocking buffer 5% BSA+PBS
antibody diluting buffer 5% BSA+PBS+50% blank mouse serum ELISA plate washing buffer 0.1% Tween+PBS 3) The two coated ELISA plates were washed with 300 μl/well of PBS for 3 times;

4) the blocking buffer were added, 200 μl per well, to block the plates at 37° C. for 1 hour;

5) Initially each of the serum samples was diluted with the blocking buffer into an appropriate concentration, and then diluted with the antibody diluting buffer to obtain serial dilutions over a suitable concentration range. Particular dilution fold used to achieve the concentrations was determined through adjustments in pre-experiments, provided that the dilution fold enabled finally measured values about color development of the serum samples to fall within the range of measured values of the standards;

6) Antibody standards were diluted with the antibody diluting buffer. How to dilute the standards was determined through adjustments in pre-experiments as well, so that a linear curve could be fitted out by using the standards (or an S-shaped curve could be fitted out if an appropriate software was available);

7) the blocking buffer in the two coated ELISA plates was poured off, and the diluted antibody standards and serum samples to be tested were added into the plates, 100 μl per well, which were then incubated at 37° C. for 1 hour;

8) The plates were washed with PBST for 3 times;

9) 1:5000 diluted secondary antibody were added into the washed ELISA plates, 100 μl per well, which were then incubated at 37° C. for 40 minutes;

10) The plates were washed with PBST for 3 times;

11) TMB substrate were added, 100 μl per well, for color development in dark for 10 minutes;

12) 50 μl of 2 M HCl were added to stop reaction, and absorbance at 450 nm was read.

Figure 8:
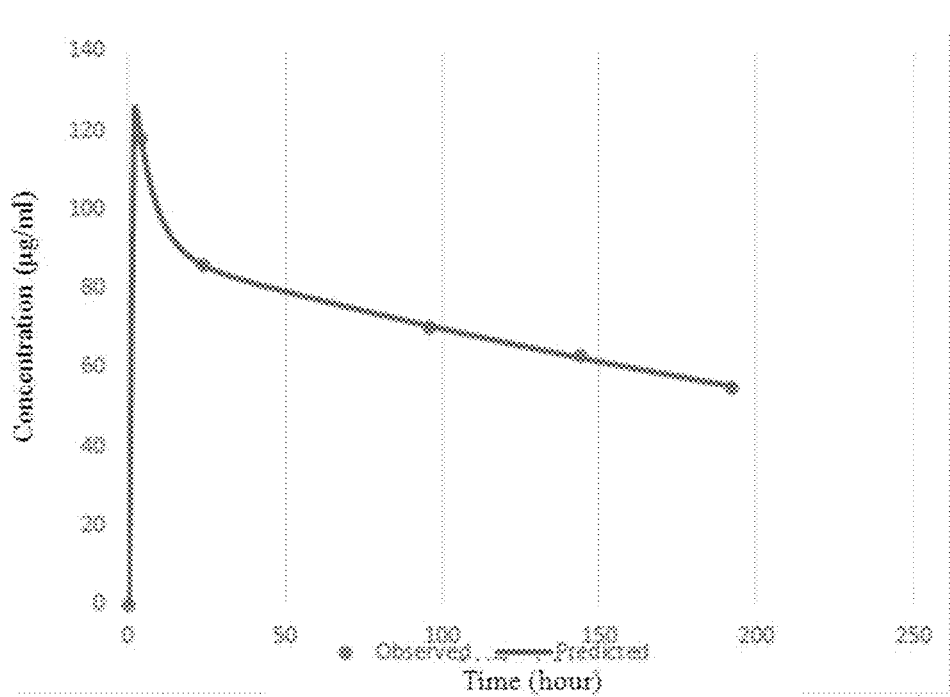
FIG. 8 shows in vivo pharmacokinetics of antibodies in mice, in which panel 8A: control antibody Enfortumab; panel 8B: 42D20 hz10.
Figure 8:
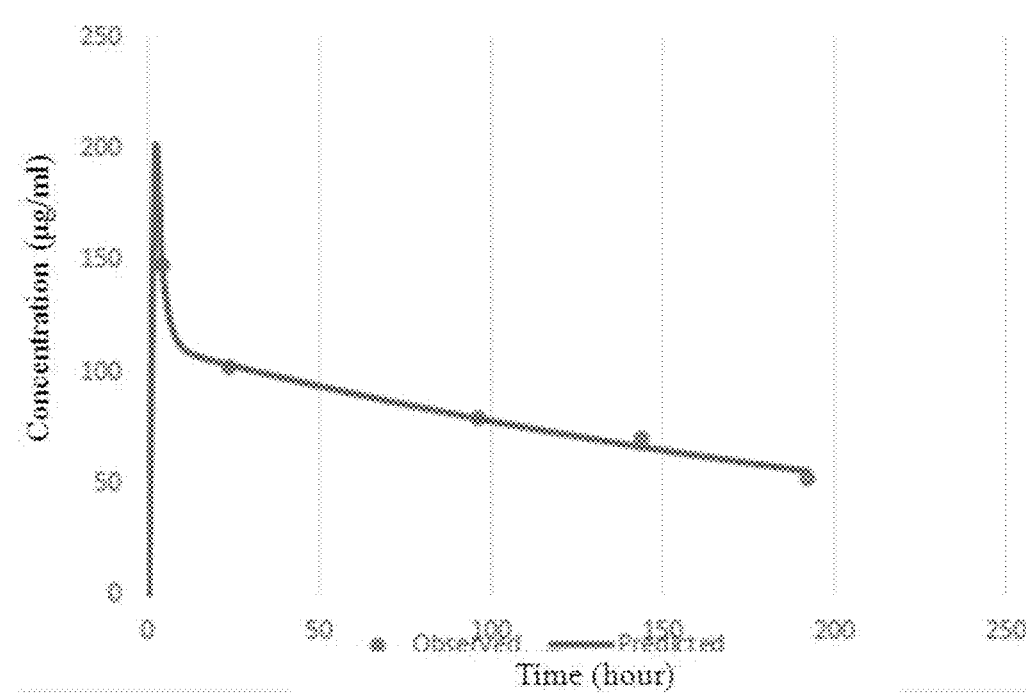

The results are shown in panels 8A and 8B in FIG. 8 and Table 20.

TABLE 20

| | In vivo pharmacokinetics of antibodies in mice | | | | | | | |
|---|---|---|---|---|---|---|---|---|
| | ref Ab (ENFORTUMAB) | | | | B07 (40D20 hz10) | | | |
| | 200 μg/mouse, IV | | 200 μg/mouse, IP | | 200 μg/mouse, IV | | 200 μg/mouse, IP | |
| Time point (h) | 21 | 22 | 23 | 24 | 17 | 18 | 19 | 20 |
| 0 | NA | NA | NA | NA | NA | NA | NA | NA |
| 4 | 117.76 | 140.80 | 102.96 | 117.30 | 147.42 | 152.18 | 113.02 | 95.18 |
| 24 | 85.84 | 94.06 | 87.58 | 101.18 | 102.24 | 96.92 | 96.58 | 86.68 |
| 96 | 70.35 | 85.30 | 78.25 | 88.61 | 79.97 | 87.77 | 85.11 | 80.49 |
| 144 | 63.01 | 69.44 | 68.95 | 81.00 | 69.63 | 78.54 | 72.41 | 70.44 |
| 192 | 55.11 | 61.29 | 62.74 | 72.32 | 52.81 | 53.34 | 56.65 | 59.55 |
| Calculated t1/2 (h) | 274.65 | 273.67 | 348.04 | 354.04 | 189.92 | 241.13 | 261.30 | 315.86 |

Concentration: μg/ml

NA: less than a lower limit of detection which was 9.77 ng/ml.

The above description of the embodiments of the present disclosure is not intended to limit the present disclosure, and those skilled in the art may make various changes and modifications to the present disclosure without departing from the spirit of the present disclosure, which should fall within the scope of the appended claims.

ANNEX TABLE I-1

Murine antibody 5M21 and chimeric antibody 5M21 xiIgG
Murine antibody 5M21 and chimeric antibody 5M21 xiIgG

| Heavy chain variable region (SEQ ID NO: 7) | QVQLQQSGPELVKPGASVRITCKASGYTFTTYYIHWVKQR PGQGLEWIGWIYPGNVNTKYNEKFKGKATLTADKSSSTA YMQLSSLTSEDSAVYFCARGLYYFDYWGQGTTLTVSS | | | Light chain variable region (SEQ ID NO: 8) | SIVMTQTPKFLLVSAGDRLTITCKASQSVSNDVAWY QQKPGQSPKLLIYYASNRYTGVPDRFTGSGYGTDFT FTISTVQAEDLAVYFCQQDYSSPYTFGGGTKLEIK | | |
|---|---|---|---|---|---|---|---|
| ID NO: 7) | CDR-H1 | CDR-H2 | CDR-H3 | ID NO: 8) | CDR-L1 | CDR-L2 | CDR-L3 |
| CHOTHIA | GYTFTTY--- (SEQ ID NO: 35) | -----YPGNVN--------- (SEQ ID NO: 39) | --GLYYFDY (SEQ ID NO: 43) | CHOTHIA | KASQSVSNDV A-- (SEQ ID NO: 45) | ----YASNRYT (SEQ ID NO: 47) | QQDYSSPYT (SEQ ID NO: 49) |
| ABM | GYTFTTYYIH (SEQ ID NO: 36) | ---WIYPGNVNTK------- (SEQ ID NO: 40) | --GLYYFDY (SEQ ID NO: 43) | ABM | KASQSVSNDV A-- (SEQ ID NO: 45) | ----YASNRYT (SEQ ID NO: 47) | QQDYSSPYT (SEQ ID NO: 49) |
| KABAT | -----TYYIH (SEQ ID NO: 37) | --- WIYPGNVNTKYNEKF KG (SEQ ID NO: 41) | --GLYYFDY (SEQ ID NO: 43) | KABAT | KASQSVSNDV A-- (SEQ ID NO: 45) | ----YASNRYT (SEQ ID NO: 47) | QQDYSSPYT (SEQ ID NO: 49) |

ANNEX TABLE I-1-continued

| Murine antibody 5M21 and chimeric antibody 5M21 xiIgG | | | |
|---|---|---|---|
| Murine antibody 5M21 and chimeric antibody 5M21 xiIgG | | | |

| Heavy chain variable region (SEQ ID NO: 7) | QVQLQQSGPELVKPGASVRITCKASGYTFTTYYIHWVKQR PGQGLEWIGWIYPGNVNTKYNEKFKGKATLTADKSSSTA YMQLSSLTSEDSAVYFCARGLYYFDYWGQGTTLTVSS | | | Light chain variable region (SEQ ID NO: 8) | SIVMTQTPKFLLVSAGDRLTITCKASQSVSNDVAWY QQKPGQSPKLLIYYASNRYTGVPDRFTGSGYGTDFT FTISTVQAEDLAVYFCQQDYSSPYTFGGGTKLEIK | | |
|---|---|---|---|---|---|---|---|
| | CDR-H1 | CDR-H2 | CDR-H3 | | CDR-L1 | CDR-L2 | CDR-L3 |
| CONTACT | ----TTYYIH (SEQ ID NO: 38) | WIGWIYPGNVNTK----- -- (SEQ ID NO: 42) | ARGLYYFD- (SEQ ID NO: 44) | CONTACT | ------ SNDVAWY (SEQ ID NO: 46) | LLIYYASNRY- (SEQ ID NO: 48) | QQDYSSPY- (SEQ ID NO: 50) |

ANNEX TABLE I-2

| Humanized sequences based on murine antibody 5M21 | | |
|---|---|---|
| Heavy chain variable region | 5M21_VH_hz0 (SEQ ID NO: 9) | QVQLVQSGAEVKKPGASVKVSCKASGYTFTTYYIHWVRQAPGQRLEWMGWIYPGNVN TKYNEKFKGRVTITRDTSASTAYMELSSLRSEDTAVYYCARGLYYFDYWGQGTLVTVSS |
| | 5M21_VH_hz1 (SEQ ID NO: 10) | QVQLVQSGAEVKKPGASVKVSCKASGYTFTTYYIHWVRQAPGQRLEWMGWIYPGNVN TKYNEKFKGRVTITRDKSASTAYMELSSLRSEDTAVYYCARGLYYFDYWGQGTLVTVSS |
| Light chain variable region | 5M21_VL_hz0 (SEQ ID NO: 11) | DIQMTQSPSSLSASVGDRVTITCKASQSVSNDVAWYQQKPGKVPKLLIYYASNRYTGVPS RFSGSGSGTDFTLTISSLQPEDVATYYCQQDYSSPYTFGGGTKVEIK |
| | 5M21_VL_hz1 (SEQ ID NO: 12) | DIQMTQSPSSLSASVGDRVTITCKASQSVSNDVAWYQQKPGKVPKLLIYYASNRYTGVPS RFSGSGSGTDFTLTISSLQPEDLATYYFCQQDYSSPYTFGGGTKVEIK |

ANNEX TABLE I-3

| Humanized antibodies comprising humanized sequences based on murine antibody 5M21 | | | | | | | |
|---|---|---|---|---|---|---|---|
| 5M21_hz00 | | | | | | | |
| Heavy chain variable region | 5M21_VH_hz0 (SEQ ID NO: 9) | | | Light chain variable region | 5M21_VL_hz0 (SEQ ID NO: 11) | | |
| | CDR-H1 | CDR-H2 | CDR-H3 | | CDR-L1 | CDR-L2 | CDR-L3 |
| CHOTHIA | GYTFTTY (SEQ ID NO: 35) | YPGNVN (SEQ ID NO: 39) | GLYYFDY (SEQ ID NO: 43) | CHOTHIA | KASQSVSNDVA (SEQ ID NO: 45) | YASNRYT (SEQ ID NO: 47) | QQDYSSPYT (SEQ ID NO: 49) |
| 5M21 hz01 | | | | | | | |
| Heavy chain variable region | 5M21_VH_hz0 (SEQ ID NO: 9) | | | Light chain variable region | 5M21_VL_hz1 (SEQ ID NO: 12) | | |
| | CDR-H1 | CDR-H2 | CDR-H3 | | CDR-L1 | CDR-L2 | CDR-L3 |
| CHOTHIA | GYTFTTY (SEQ ID NO: 35) | YPGNVN (SEQ ID NO: 39) | GLYYFDY (SEQ ID NO: 43) | CHOTHIA | KASQSVSNDVA (SEQ ID NO: 45) | YASNRYT (SEQ ID NO: 47) | QQDYSSPYT (SEQ ID NO: 49) |
| 5M21 hz10 | | | | | | | |
| Heavy chain variable region | 5M21_VH_hz1 (SEQ ID NO: 10) | | | Light chain variable region | 5M21_VL_hz0 (SEQ ID NO: 11) | | |
| | CDR-H1 | CDR-H2 | CDR-H3 | | CDR-L1 | CDR-L2 | CDR-L3 |
| CHOTHIA | GYTFTTY (SEQ ID NO: 35) | YPGNVN (SEQ ID NO: 39) | GLYYFDY (SEQ ID NO: 43) | CHOTHIA | KASQSVSNDVA (SEQ ID NO: 45) | YASNRYT (SEQ ID NO: 47) | QQDYSSPYT (SEQ ID NO: 49) |

ANNEX TABLE I-3 -continued

Humanized antibodies comprising humanized sequences based on murine antibody 5M21

5M21 hz11

| Heavy chain variable region | 5M21_VH_hz1 (SEQ ID NO: 10) | | | Light chain variable region | 5M21_VL_hz1 (SEQ ID NO: 12) | | |
|---|---|---|---|---|---|---|---|
| | CDR-H1 | CDR-H2 | CDR-H3 | | CDR-L1 | CDR-L2 | CDR-L3 |
| CHOTHIA | GYTFTTY (SEQ ID NO: 35) | YPGNVN (SEQ ID NO: 39) | GLYYFDY (SEQ ID NO: 43) | CHOTHIA | KASQSVSNDVA (SEQ ID NO: 45) | YASNRYT (SEQ ID NO: 47) | QQDYSSPYT (SEQ ID NO: 49) |

ANNEX TABLE II-1

Murine antibody 42D20 and chimeric antibody 42D20 xiIgG
Murine antibody 42D20 and chimeric antibody 42D20 xiIgG

| Heavy chain variable region (SEQ ID NO: 13) | QVQLKESGPGLVAPSQSLSISCTVSGFSLIDYGVSWIR QPPGKGLEWLGVIWGDGKIYYNSVLKSRLSISKDNSKQ VFLKMNSLQTDDTAMYYCAKQGGLLFYAMDYWGQGTSV TVSS | | | Light chain variable region (SEQ ID NO: 14) | DIVMTQSPSSLAMSVGQRVTMNCKSSQSLLNSYSQK NYLAWYQQKPGQSPKLLIYFASTRESGVPDRFIGSG SETDFTLTISSVQAEDLADYFCQQHYNTPFTFGSGT KLEIK | | |
|---|---|---|---|---|---|---|---|
| | CDR-H1 | CDR-H2 | CDR-H3 | | CDR-L1 | CDR-L2 | CDR-L3 |
| CHOTHIA | GFSLIDY--- (SEQ ID NO: 51) | -----WGDGK----- ---- (SEQ ID NO: 55) | --QGGLLFYAMDY (SEQ ID NO: 59) | CHOTIA | KSSQSLLNSYSQKNY LA-- (SEQ ID NO: 61) | ----FASTRES (SEQ ID NO: 63) | QQHYNTPFT (SEQ ID NO: 65) |
| ABM | GFSLIDYGVS (SEQ ID NO: 52) | ---VIWGDGKIY--- ---- (SEQ ID NO: 56) | --QGGLLFYAMDY (SEQ ID NO: 59) | ABM | KSSQSLLNSYSQKNY LA-- (SEQ ID NO: 63) | ----FASTRES (SEQ ID NO: 63) | QQHYNTPFT (SEQ ID NO: 65) |
| KABAT | -----DYGVS (SEQ ID NO: 53) | ---VIMGDGKIYYNS VLKS (SEQ ID NO: 57) | --QGGLLFYAMDY (SEQ ID NO: 59) | KABAT | KSSQSLLNSYSQKNY LA-- (SEQ ID NO: 63) | ----FASTRES (SEQ ID NO: 63) | QQHYNTPFT (SEQ ID NO: 65) |
| CONTACT | ----IDYGVS (SEQ ID NO: 54) | WLGVIWGDGKIY--- ---- (SEQ ID NO: 58) | AKQGGLLFYAMD- (SEQ ID NO: 60) | CONTACT | ------LNSYSQKNY LAWY (SEQ ID NO: 63) | LLIYFASTRE- (SEQ ID NO: 64) | QQHYNTPF- (SEQ ID NO: 66) |

ANNEX TABLE II-2

Humanized sequences based on murine antibody 42D20

| Heavy chain variable region | 42D20_VH_hz0 (SEQ ID NO: 15) | QVQLQESGPGLVKPSETLSLTCTVSGFSLIDYGVSWIRQPPGKGLEWIGVIWGDGKIYYNS VLKSRVTISVDTSKNQFSLKLSSVTAADTAVYYCARQGGLLFYAMDYWGQGTLVTVSS |
|---|---|---|
| | 42D20_VH_hz1 (SEQ ID NO: 16) | QVQLQESGPGLVKPSETLSLTCTVSGFSLIDYGVSWIRQPPGKGLEWIGVIWGDGKIYYNS VLKSRVTISKDNSKSQVSLKLSSVTAADTAVYYCAKQGGLLFYAMDYWGQGTLVTVSS |
| | 42D20_VH_hz2 (SEQ ID NO: 17) | QVQLQESGPGLVKPSETLSLTCTVSGFSLIDYGVSWIRQPPGKGLEWIGVIWGEGKIYYNS VLKSRVTISKDNSKSQVSLKLSSVTAADTAVYYCAKQGGLLFYAMDYWGQGTLVTVSS |
| | 42D20_VH_hz3 (SEQ ID NO: 18) | QVQLQESGPGLVKPSETLSLTCTVSGFSLIDYGVSWIRQPPGKGLEWIGVIWGDGKIYYNS VLKSRVTISKDNSKSQVSLKLSSVTAADTAVYYCARQGGLLFYAMDYWGQGTLVTVSS |
| | 42D20_VH_hz4 (SEQ ID NO: 19) | QVQLQESGPGLVKPSETLSLTCTVSGFSLIDYGVSWIRQPPGKGLEWIGVIWGDAKIYYNS VLKSRVTISKDNSKSQVSLKLSSVTAADTAVYYCAKQGGLLFYAMDYWGQGTLVTVSS |
| | 42D20_VH_hz5 (SEQ ID NO: 20) | QVQLQESGPGLVKPSETLSLTCTVSGFSLIDYGVSWIRQPPGKGLEWIGVIWGGDKIYYNS VLKSRVTISKDNSKSQVSLKLSSVTAADTAVYYCAKQGGLLFYAMDYWGQGTLVTVSS |
| | 42D20_VH_hz6 (SEQ ID NO: 21) | QVQLQESGPGLVKPSETLSLTCTVSGFSLIDYGVSWIRQPPGKGLEWIGVIWGGGKIYYNS VLKSRVTISKDNSKSQVSLKLSSVTAADTAVYYCAKQGGLLFYAMDYWGQGTLVTVSS |
| Light chain variable region | 42D20_VL_hz0 (SEQ ID NO: 22) | DIVMTQSPDSLAVSLGERATINCKSSQSLLNSYSQKNYLAWYQQKPGQPPKLLIYFASTRE SGVPDRFSGSGSGTDFTLTISSLQAEDVAVYYCQQHYNTPFTFGAGTKLELKR |
| | 42D20_VL_hz1 (SEQ ID NO: 23) | DIVMTQSPDSLAVSLGERATINCKSSQSLLNSYSQKNYLAWYQQKPGQSPKLLIYFASTRE SGVPDRFSGSGSETDFTLTISSLQAEDLAVYFCQQHYNTPFTFGAGTKLELKR |
| | 42D20_VL_hz2 (SEQ ID NO: 24) | DIVMTQSPDSLAVSLGERATINCKSSQSLLYSYSQKNYLAWYQQKPGQSPKLLIYFASTRE SGVPDRFSGSGSETDFTLTISSLQAEDLAVYFCQQHYNTPFTFGAGTKLELKR |
| | 42D20_VL_hz3 (SEQ ID NO: 25) | DIVMTQSPDSLAVSLGERATINCKSSQSLLNTYSQKNYLAWYQQKPGQSPKLLIYFASTR ESGVPDRFSGSGSETDFTLTISSLQAEDLAVYFCQQHYNTPFTFGAGTKLELKR |

ANNEX TABLE II-2 -continued

Humanized sequences based on murine antibody 42D20

| | |
|---|---|
| 42D20_VL_hz4 (SEQ ID NO: 26) | DIVMTQSPDSLAVSLGERATINCKSSQSLLNKYSQKNYLAWYQQKPGQPPKLLIYFASTR ESGVPDRFSGSGSGTDFTLTISSLQAEDVAVYYCQQHYNTPFTFGAGTKLELKR |

ANNEX TABLE II-3

Humanized antibodies comprising humanized sequences based on murine antibody 42D20

42D20 hz10

| Heavy chain variable | 42D20_VH_hz1 (SEQ ID NO: 16) | | | Light chain variable | 42D20_VL_hz0 (SEQ ID NO: 22) | | |
|---|---|---|---|---|---|---|---|
| region | CDR-H1 | CDR-H2 | CDR-H3 | region | CDR-L1 | CDR-L2 | CDR-L3 |
| CHOTHIA | GFSLIDY (SEQ ID NO: 51) | WGDGK (SEQ ID NO: 55) | QGGLLFYAMD Y (SEQ ID NO: 59) | CHOTHIA | KSSQSLLNSYSQKN YLA (SEQ ID NO: 61) | FASTRES (SEQ ID NO: 63) | QQHYNTPFT (SEQ ID NO: 65) |

42D20 hz11

| Heavy chain variable | 42D20_VH_hz1 (SEQ ID NO: 16) | | | Light chain variable | 42D20_VL_hz1 (SEQ ID NO: 23) | | |
|---|---|---|---|---|---|---|---|
| region | CDR-H1 | CDR-H2 | CDR-H3 | region | CDR-L1 | CDR-L2 | CDR-L3 |
| CHOTHIA | GFSLIDY (SEQ ID NO: 51) | WGDGK (SEQ ID NO: 55) | QGGLLFYAMD Y (SEQ ID NO: 59) | CHOTHIA | KSSQSLLNSYSQKN YLA (SEQ ID NO: 61) | FASTRES (SEQ ID NO: 63) | QQHYNTPFT (SEQ ID NO: 65) |

42D20 hz13

| Heavy chain variable | 42D20_VH_hz1 (SEQ ID NO: 16) | | | Light chain variable | 42D20_VL_hz3 (SEQ ID NO: 25) | | |
|---|---|---|---|---|---|---|---|
| region | CDR-H1 | CDR-H2 | CDR-H3 | region | CDR-L1 | CDR-L2 | CDR-L3 |
| CHOTHIA | GFSLIDY (SEQ ID NO: 51) | WGDGK (SEQ ID NO: 55) | QGGLLFYAMD Y (SEQ ID NO: 59) | CHOTHIA | KSSQSLLNTYSQK NYLA (SEQ ID NO: 67) | FASTRES (SEQ ID NO: 63) | QQHYNTPFT (SEQ ID NO: 65) |

42D20 hz43

| Heavy chain variable | 42D20_VH_hz4 (SEQ ID NO: 19) | | | Light chain variable | 42D20_VL_hz3 (SEQ ID NO: 25) | | |
|---|---|---|---|---|---|---|---|
| region | CDR-H1 | CDR-H2 | CDR-H3 | region | CDR-L1 | CDR-L2 | CDR-L3 |
| CHOTHIA | GFSLIDY (SEQ ID NO: 51) | WGDGK (SEQ ID NO: 55) | QGGLLFYAMD Y (SEQ ID NO: 59) | CHOTHIA | KSSQSLLNTYSQK NYLA (SEQ ID NO: 67) | FASTRES (SEQ ID NO: 63) | QQHYNTPFT (SEQ ID NO: 65) |

42D20 hz63

| Heavy chain variable | 42D20_VH_hz6 (SEQ ID NO: 21) | | | | 42D20_VL_hz3 (SEQ ID NO: 25) | | |
|---|---|---|---|---|---|---|---|
| region | CDR-H1 | CDR-H2 | CDR-H3 | | CDR-L1 | CDR-L2 | CDR-L3 |
| CHOTHIA | GFSLIDY (SEQ ID NO: 51) | WGDGK (SEQ ID NO: 55) | QGGLLFYAMD Y (SEQ ID NO: 59) | CHOTHIA | KSSQSLLNTYSQK NYLA (SEQ ID NO: 67) | FASTRES (SEQ ID NO: 63) | QQHYNTPFT (SEQ ID NO: 65) |

ANNEX TABLE III-1

| Murine antibody 20M12 and chimeric antibody 20M12 xiIgG<br>Murine antibody 20M12 and chimeric antibody 20M12 xiIgG |
| --- |

| Heavy chain variable region (SEQ ID NO: 27) | QVQLQQSGPELVKPGASVRISCKASGYTFTSYYIHWVKQR<br>PGQGLEWIGWIYPGNANNKYNENFKGKATLTADKSSSTA<br>YMQLSSLTSEDSAVYFCARSVYYFDYWGQGTTLTVSS | Light chain variable region (SEQ ID NO: 28) | SVVMTQTPKFLLVSAGDRVTITCKASQSVSNDVAWYQ<br>QKPGQSPKLLIYYASNRNTGVPDRFTGSGYGTDFTFNIS<br>TVQAEDLAVYFCQQDYSSPYTFGGGTKLEIK |
| --- | --- | --- | --- |

| | CDR-H1 | CDR-H2 | CDR-H3 | | CDR-L1 | CDR-L2 | CDR-L3 |
| --- | --- | --- | --- | --- | --- | --- | --- |
| CHOTHIA | GYTFTSY---<br>(SEQ ID<br>NO: 70) | -----YPGNAN---<br>------<br>(SEQ ID NO: 74) | --SVYYFDY<br>(SEQ ID<br>NO: 78) | CHOTHIA | KASQSVSNDVA<br>--<br>(SEQ ID<br>NO: 45) | ----YASNRNT<br>(SEQ ID<br>NO: 80) | QQDYSSPYT<br>(SEQ ID<br>NO: 49) |
| ABM | GYTFTSYYIH<br>(SEQ ID<br>NO: 71) | ---WIYPGNANNK-<br>------<br>(SEQ ID NO: 75) | --SVYYFDY<br>(SEQ ID<br>NO: 78) | ABM | KASQSVSNDVA<br>--<br>(SEQ ID<br>NO: 45) | ----YASNRNT<br>(SEQ ID<br>NO: 80) | QQDYSSPYT<br>(SEQ ID<br>NO: 49) |
| KABAT | -----SYYIH<br>(SEQ ID<br>NO: 72) | ---WIYPGNANNKY<br>NENFKG<br>(SEQ ID NO: 76) | --SVYYFDY<br>(SEQ ID<br>NO: 78) | KABAT | KASQSVSNDVA<br>--<br>(SEQ ID<br>NO: 45) | ----YASNRNT<br>(SEQ ID<br>NO: 80) | QQDYSSPYT<br>(SEQ ID<br>NO: 49) |
| CONTACT | ----TSYYIH<br>(SEQ ID<br>NO: 73) | WIGWIYPGNANNK-<br>------<br>(SEQ ID NO: 77) | ARSVYYFD-<br>(SEQ ID<br>NO: 79) | CONTACT | ------SNDVAWY<br>(SEQ ID<br>NO: 46) | LLIYYASNRN-<br>(SEQ ID<br>NO: 81) | QQDYSSPY-<br>(SEQ ID<br>NO: 50) |

ANNEX TABLE III-2

| humanized sequences based on murine antibody 20M12 |
| --- |

| Heavy chain variable region | 20M12_VH_hz0<br>(SEQ ID NO: 29)<br>20M12_VH_hz1<br>(SEQ ID NO: 30) | QVQLVQSGAEVKKPGASVKVSCKASGYTFTSYYIHWVRQAPGQRLEWMGWIYPGNAN<br>NKYNENFKGRVTITRDTSASTAYMELSSLRSEDTAVYYCARSVYYFDYWGQGTLVTVSS<br>QVQLVQSGAEVKKPGASVKVSCKASGYTFTSYYIHWVRQAPGQRLEWMGWIYPGNAN<br>NKYNENFKGRVTITADKSASTAYMELSSLRSEDTAVYYCARSVYYFDYWGQGTLVTVSS |
| --- | --- | --- |
| Light chain variable region | 20M12_VL_hz0<br>(SEQ ID NO: 31)<br>20M12_VL_hz1<br>(SEQ ID NO: 32) | EIVMTQSPATLSVSPGERATLSCKASQSVSNDVAWYQQKPGQAPRLLIYYASNRNTGIPA<br>RFSGSGSGTEFTLTISSLQSEDFAVYYCQQDYSSPYTFGGGTKVEIK<br>EVVMTQSPATLSVSPGERATLSCKASQSVSNDVAWYQQKPGQAPRLLIYYASNRNTGIPA<br>RFSGSGSGTEFTLTISSLQSEDLAVYFCQQDYSSPYTFGGGTKVEIK |

ANNEX TABLE III-3

| Humanized antibodies comprising humanized sequences based on murine antibody 20M12 |
| --- |

| 20M12 hz01 | | | | | | | |
| --- | --- | --- | --- | --- | --- | --- | --- |
| Heavy chain variable | 20M12_VH_hz0 (SEQ ID NO: 29) | | | Light chain variable | 20M12_VL_hz1 (SEQ ID NO: 32) | | |
| region | CDR-H1 | CDR-H2 | CDR-H3 | region | CDR-L1 | CDR-L2 | CDR-L3 |
| CHOTHIA | GYTFTSY<br>(SEQ ID<br>NO: 70) | YPGNAN<br>(SEQ ID<br>NO: 74) | SVYYFDY<br>(SEQ ID<br>NO: 78) | CHOTHIA | KASQSVSNDVA<br>(SEQ ID<br>NO: 45) | YASNRNT<br>(SEQ ID<br>NO: 80) | QQDYSSPYT<br>(SEQ ID<br>NO: 49) |

| 20M12 hz11 | | | | | | | |
| --- | --- | --- | --- | --- | --- | --- | --- |
| Heavy chain variable | 20M12_VH_hz1 (SEQ ID NO: 30) | | | Light chain variable | 20M12_VL_hz1 (SEQ ID NO: 32) | | |
| region | CDR-H1 | CDR-H2 | CDR-H3 | region | CDR-L1 | CDR-L2 | CDR-L3 |
| CHOTHIA | GYTFTSY<br>(SEQ ID<br>NO: 70) | YPGNAN<br>(SEQ ID<br>NO: 74) | SVYYFDY<br>(SEQ ID<br>NO: 78) | CHOTHIA | KASQSVSNDVA<br>(SEQ ID<br>NO: 45) | YASNRNT<br>(SEQ ID<br>NO: 80) | QQDYSSPYT<br>(SEQ ID<br>NO: 49) |

ANNEX TABLE IV-1

| Murine antibody 30J3 and chimeric antibody 30J3 xiIgG |
|---|
| Murine antibody 30J3 and chimeric antibody 30J3 xiIgG |

| Heavy chain variable region (SEQ ID NO: 33) | EVQLQQSGPDLVKPGASVKISCKASGYSFTDYYMHWVKQS RGKGLEWIGRVNPNNGNTLYNQKPRGKAILTVDKSSSTAY MELRSLTSDDSAVYYCAREDRYAFAYWGQGTLVTVSA | | Light chain variable region (SEQ ID NO: 34) | DIVLTQSPASLAVSLGQRATISCRASQSVSTSSYTYMHW YQQKPGQPPKLLIKYASNLESGVPARFIGSGSGTDFTLNI HPVEEEDTATYYCQHTWEIPYTFGGGTKLEIK | | |

| | CDR-H1 | CDR-H2 | CDR-H3 | NO: 34) | CDR-L1 | CDR-L2 | CDR-L3 |
|---|---|---|---|---|---|---|---|
| CHOTHIA | GYSFTDY--- (SEQ ID NO: 82) | ------NPNNGN---- ----- (SEQ ID NO: 86) | --EDRYAFAY (SEQ ID NO: 90) | CHOTHIA | RASQSVSTSSYTY MH-- (SEQ ID NO: 92) | ----YASNLES (SEQ ID NO: 94) | QHTWEIPYT (SEQ ID NO: 96) |
| ABM | GYSFTDYYMH (SEQ ID NO: 83) | ---RVNPNNGNTL-- ----- (SEQ ID NO: 87) | --EDRYAFAY (SEQ ID NO: 90) | ABM | RASQSVSTSSYTY MH-- (SEQ ID NO: 92) | ----YASNLES (SEQ ID NO: 94) | QHTWEIPYT (SEQ ID NO: 96) |
| KABAT | -----DYYMH (SEQ ID NO: 84) | --- RVNPNNGNTLYNQKF RG (SEQ ID NO: 88) | --EDRYAFAY (SEQ ID NO: 90) | KABAT | RASQSVSTSSYTY MH-- (SEQ ID NO: 92) | ----YASNLES (SEQ ID NO: 94) | QHTWEIPYT (SEQ ID NO: 96) |
| CONTACT | ----TDYYMH (SEQ ID NO: 85) | WIGRVNPNNGNTL-- ----- (SEQ ID NO: 89) | AREDRYAFA- (SEQ ID NO: 91) | CONTACT | ------ STSSYTYMHWY (SEQ ID NO: 93) | LLIKYASNLE- (SEQ ID NO: 95) | QHTWEIPY- (SEQ ID NO: 97) |

What is claimed is:

1. An antibody molecule or fragment thereof, which comprises a heavy chain variable region (VH) and a light chain variable region (VL) comprising a combination of heavy and light chain CDRs selected from:

(1) CDR-H1 (GYTFTTY), CDR-H2 (YPGNVN), and CDR-H3 (GLYYFDY) shown in SEQ ID NOs: 35, 39, and 43; and, CDR-L1 (KASQSVSNDVA), CDR-L2 (YASNRYT), and CDR-L3 (QQDYSSPYT) shown in SEQ ID NOs: 45, 47, and 49;

(2) CDR-H1 (GYTFTTYYIH), CDR-H2 (WIYPGNVNTK), and CDR-H3 (GLYYFDY) shown in SEQ ID NOs: 36, 40, and 43; and, CDR-L1 (KASQSVSNDVA), CDR-L2 (YASNRYT), and CDR-L3 (QQDYSSPYT) shown in SEQ ID NOs: 45, 47, and 49;

(3) CDR-H1 (TYYIH), CDR-H2 (WIYPGNVNT-KYNEKFKG), and CDR-H3 (GLYYFDY) shown in SEQ ID NOs: 37, 41, and 43; and, CDR-L1 (KASQSVSNDVA), CDR-L2 (YASNRYT), and CDR-L3 (QQDYSSPYT) shown in SEQ ID NOs: 45, 47, and 49;

(4) CDR-H1 (TTYYIH), CDR-H2 (WIGWIYPGNVNTK), and CDR-H3 (ARGLYYFD) shown in SEQ ID NOs: 38, 42, and 44; and, CDR-L1 (SNDVAWY), CDR-L2 (LLIYYASNRY), and CDR-L3 (QQDYSSPY) shown in SEQ ID NOs: 46, 48, and 50;

(5) CDR-H1 (GFSLIDY), CDR-H2 (WGDGK), and CDR-H3 (QGGLLFYAMDY) shown in SEQ ID NOs: 51, 55, and 59; and, CDR-L1 (KSSQSLLNSYSQK-NYLA), CDR-L2 (FASTRES), and CDR-L3 (QQHYNTPFT) shown in SEQ ID NOs: 61, 63, and 65;

(6) CDR-H1 (GFSLIDYGVS), CDR-H2 (VIWGDG-KIY), and CDR-H3 (QGGLLFYAMDY) shown in SEQ ID NOs: 52, 56, and 59; and, CDR-L1 (KSSQSLLNSYSQKNYLA), CDR-L2 (FASTRES), and CDR-L3 (QQHYNTPFT) shown in SEQ ID NOs: 61, 63, and 65;

(7) CDR-H1 (DYGVS), CDR-H2 (VIWGDGKIYYNS-VLKS), and CDR-H3 (QGGLLFYAMDY) shown in SEQ ID NOs: 53, 57, and 59; and, CDR-L1 (KSSQSLLNSYSQKNYLA), CDR-L2 (FASTRES), and CDR-L3 (QQHYNTPFT) shown in SEQ ID NOs: 61, 63, and 65;

(8) CDR-H1 (IDYGVS), CDR-H2 (WLGVIWGDG-KIY), and CDR-H3 (AKQGGLLFYAMD) shown in SEQ ID NOs: 54, 58, and 60; and, CDR-L1 (LNSYS-QKNYLAWY), CDR-L2 (LLIYFASTRE), and CDR-L3 (QQHYNTPF) shown in SEQ ID NOs: 62, 64, and 66;

(9) CDR-H1 (GFSLIDY), CDR-H2 (WGDGK), and CDR-H3 (QGGLLFYAMDY) shown in SEQ ID NOs: 51, 55, and 59; and, CDR-L1 (KSSQSLLNTYSQK-NYLA), CDR-L2 (FASTRES), and CDR-L3 (QQHYNTPFT) shown in SEQ ID NOs: 67, 63, and 65;

(10) CDR-H1 (GFSLIDY), CDR-H2 (WGDAK), and CDR-H3 (QGGLLFYAMDY) shown in SEQ ID NOs: 51, 68, and 59; and, CDR-L1 (KSSQSLLNTYSQK-NYLA), CDR-L2 (FASTRES), and CDR-L3 (QQHYNTPFT) shown in SEQ ID NOs: 67, 63, and 65;

(11) CDR-H1 (GFSLIDY), CDR-H2 (WGGGK), and CDR-H3 (QGGLLFYAMDY) shown in SEQ ID NOs: 51, 69, and 59; and, CDR-L1 (KSSQSLLNTYSQK- NYLA), CDR-L2 (FASTRES), and CDR-L3 (QQHYNTPFT) shown in SEQ ID NOs: 67, 63, and 65;

(12) CDR-H1 (GYTFTSY), CDR-H2 (YPGNAN), and CDR-H3 (SVYYFDY) shown in SEQ ID NOs: 70, 74, and 78; and, CDR-L1 (KASQSVSNDVA), CDR-L2 (YASNRNT), and CDR-L3 (QQDYSSPYT) shown in SEQ ID NOs: 45, 80, and 49;

(13) CDR-H1 (GYTFTSYYIH), CDR-H2 (WIYPG-NANNK), and CDR-H3 (SVYYFDY) shown in SEQ ID NOs: 71, 75, and 78; and, CDR-L1 (KASQSVSNDVA), CDR-L2 (YASNRNT), and CDR-L3 (QQDYSSPYT) shown in SEQ ID NOs: 45, 80, and 49;

(14) CDR-H1 (SYYIH), CDR-H2 (WIYPG-NANNKYNENFKG), and CDR-H3 (SVYYFDY) shown in SEQ ID NOs: 72, 76, and 78; and, CDR-L1 (KASQSVSNDVA), CDR-L2 (YASNRNT), and CDR-L3 (QQDYSSPYT) shown in SEQ ID NOs: 45, 80, and 49;

(15) CDR-H1 (TSYYIH), CDR-H2 (WIGWIYPG-NANNK), and CDR-H3 (ARSVYYFD) shown in SEQ ID NOs: 73, 77, and 79; and, CDR-L1 (SNDVAWY), CDR-L2 (LLIYYASNRN), and CDR-L3 (QQD-YSSPY) shown in SEQ ID NOs: 46, 81, and 50;

(16) CDR-H1 (GYSFTDY), CDR-H2 (NPNNGN), and CDR-H3 (EDRYAFAY) shown in SEQ ID NOs: 82, 86, and 90; and, CDR-L1 (RASQSVSTSSYTYMH), CDR-L2 (YASNLES), and CDR-L3 (QHTWEIPYT) shown in SEQ ID NOs: 92, 94, and 96;

(17) CDR-H1 (GYSFTDYYMH), CDR-H2 (RVNPNNG-NTL), and CDR-H3 (EDRYAFAY) shown in SEQ ID NOs: 83, 87, and 90; and, CDR-L1 (RASQSVSTS-SYTYMH), CDR-L2 (YASNLES), and CDR-L3 (QHTWEIPYT) shown in SEQ ID NOs: 92, 94, and 96;

(18) CDR-H1 (DYYMH), CDR-H2 (RVNPNNGNT-LYNQKFRG), and CDR-H3 (EDRYAFAY) shown in SEQ ID NOs: 84, 88, and 90; and, CDR-L1 (RASQSVSTSSYTYMH), CDR-L2 (YASNLES), and CDR-L3 (QHTWEIPYT) shown in SEQ ID NOs: 92, 94, and 96; and

(19) CDR-H1 (TDYYMH), CDR-H2 (WIGRVNPNNG-NTL), and CDR-H3 (AREDRYAFA) shown in SEQ ID NOs: 85, 89, and 91; and, CDR-L1 (STS-SYTYMHWY), CDR-L2 (LLIKYASNLE), and CDR-L3 (QHTWEIPY) shown in SEQ ID NOs: 93, 95, and 97.

2. The antibody molecule or fragment thereof according to claim 1, wherein in the antibody molecule or fragment thereof, the heavy chain variable region comprises the amino acid sequence shown in SEQ ID NO: 7, 9, or 10, or an amino acid sequence having at least 75% identity to the amino acid sequence shown in SEQ ID NO: 7, 9, or 10; and, the light chain variable region comprises the amino acid sequence shown in SEQ ID NO: 8, 11, or 12, or an amino acid sequence having at least 75% identity to the amino acid sequence shown in SEQ ID NO: 8, 11, or 12; or, the heavy chain variable region comprises the amino acid sequence shown in SEQ ID NO: 13, 15, 16, 18, 19, 20, or 21, or an amino acid sequence having at least 75% identity to the amino acid sequence shown in SEQ ID NO: 13, 15, 16, 18, 19, 20, or 21; and, the light chain variable region comprises the amino acid sequence shown in SEQ ID NO: 14, 22, 23, or 25, or an amino acid sequence having at least 75% identity to the amino acid sequence shown in SEQ ID NO: 14, 22, 23, or 25; or the heavy chain variable region comprises the amino acid sequence shown in SEQ ID NO: 27, 29, or 30, or an amino acid sequence having at least 75% identity to the amino acid sequence shown in SEQ ID NO: 27, 29, or 30; and, the light chain variable region comprises the amino acid sequence shown in SEQ ID NO: 28, 31, or 32, or an amino acid sequence having at least 75% identity to the amino acid sequence shown in SEQ ID NO: 28, 31, or 32; or the heavy chain variable region comprises the amino acid sequence shown in SEQ ID NO: 33, or an amino acid sequence having at least 75% identity to the amino acid sequence shown in SEQ ID NO: 33; and, the light chain variable region comprises the amino acid sequence shown in SEQ ID NO: 34, or an amino acid sequence having at least 75% identity to the amino acid sequence shown in SEQ ID NO: 34.

3. The antibody molecule or fragment thereof according to claim 1, wherein the heavy chain variable region and the light chain variable region in the antibody molecule or fragment thereof are selected from combinations of amino acid sequences as follows:

(1) the amino acid sequence shown in SEQ ID NO: 7 or an amino acid sequence having at least 75% identity to the amino acid sequence shown in SEQ ID NO: 7; and, the amino acid sequence shown in SEQ ID NO: 8 or an amino acid sequence having at least 75% identity to the amino acid sequence shown in SEQ ID NO: 8;

(2) the amino acid sequence shown in SEQ ID NO: 9 or an amino acid sequence having at least 75% identity to the amino acid sequence shown in SEQ ID NO: 9; and, the amino acid sequence shown in SEQ ID NO: 11 or an amino acid sequence having at least 75% identity to the amino acid sequence shown in SEQ ID NO: 11;

(3) the amino acid sequence shown in SEQ ID NO: 9 or an amino acid sequence having at least 75% identity to the amino acid sequence shown in SEQ ID NO: 9; and, the amino acid sequence shown in SEQ ID NO: 12 or an amino acid sequence having at least 75% identity to the amino acid sequence shown in SEQ ID NO: 12;

(4) the amino acid sequence shown in SEQ ID NO: 10 or an amino acid sequence having at least 75% identity to the amino acid sequence shown in SEQ ID NO: 10; and, the amino acid sequence shown in SEQ ID NO: 11 or an amino acid sequence having at least 75% identity to the amino acid sequence shown in SEQ ID NO: 11;

(5) the amino acid sequence shown in SEQ ID NO: 10 or an amino acid sequence having at least 75% identity to the amino acid sequence shown in SEQ ID NO: 10; and, the amino acid sequence shown in SEQ ID NO: 12 or an amino acid sequence having at least 75% identity to the amino acid sequence shown in SEQ ID NO: 12;

(6) the amino acid sequence shown in SEQ ID NO: 13 or an amino acid sequence having at least 75% identity to the amino acid sequence shown in SEQ ID NO: 13; and, the amino acid sequence shown in SEQ ID NO: 14 or an amino acid sequence having at least 75% identity to the amino acid sequence shown in SEQ ID NO: 14;

(7) the amino acid sequence shown in SEQ ID NO: 16 or an amino acid sequence having at least 75% identity to the amino acid sequence shown in SEQ ID NO: 16; and, the amino acid sequence shown in SEQ ID NO: 22 or an amino acid sequence having at least 75% identity to the amino acid sequence shown in SEQ ID NO: 22;

(8) the amino acid sequence shown in SEQ ID NO: 16 or an amino acid sequence having at least 75% identity to the amino acid sequence shown in SEQ ID NO: 16;

and, the amino acid sequence shown in SEQ ID NO: 23 or an amino acid sequence having at least 75% identity to the amino acid sequence shown in SEQ ID NO: 23;

(9) the amino acid sequence shown in SEQ ID NO: 16 or an amino acid sequence having at least 75% identity to the amino acid sequence shown in SEQ ID NO: 16; and, the amino acid sequence shown in SEQ ID NO: 25 or an amino acid sequence having at least 75% identity to the amino acid sequence shown in SEQ ID NO: 25;

(10) the amino acid sequence shown in SEQ ID NO: 19 or an amino acid sequence having at least 75% identity to the amino acid sequence shown in SEQ ID NO: 19; and, the amino acid sequence shown in SEQ ID NO: 25 or an amino acid sequence having at least 75% identity to the amino acid sequence shown in SEQ ID NO: 25;

(11) the amino acid sequence shown in SEQ ID NO: 21 or an amino acid sequence having at least 75% identity to the amino acid sequence shown in SEQ ID NO: 21; and, the amino acid sequence shown in SEQ ID NO: 25 or an amino acid sequence having at least 75% identity to the amino acid sequence shown in SEQ ID NO: 25;

(12) the amino acid sequence shown in SEQ ID NO: 27 or an amino acid sequence having at least 75% identity to the amino acid sequence shown in SEQ ID NO: 27; and, the amino acid sequence shown in SEQ ID NO: 28 or an amino acid sequence having at least 75% identity to the amino acid sequence shown in SEQ ID NO: 28;

(13) the amino acid sequence shown in SEQ ID NO: 29 or an amino acid sequence having at least 75% identity to the amino acid sequence shown in SEQ ID NO: 29; and, the amino acid sequence shown in SEQ ID NO: 32 or an amino acid sequence having at least 75% identity to the amino acid sequence shown in SEQ ID NO: 32;

(14) the amino acid sequence shown in SEQ ID NO: 30 or an amino acid sequence having at least 75% identity to the amino acid sequence shown in SEQ ID NO: 30; and, the amino acid sequence shown in SEQ ID NO: 32 or an amino acid sequence having at least 75% identity to the amino acid sequence shown in SEQ ID NO: 32; or,

(15) the amino acid sequence shown in SEQ ID NO: 33 or an amino acid sequence having at least 75% identity to the amino acid sequence shown in SEQ ID NO: 33; and, the amino acid sequence shown in SEQ ID NO: 34 or an amino acid sequence having at least 75% identity to the amino acid sequence shown in SEQ ID NO: 34.

4. The antibody molecule or fragment thereof according to claim 1, wherein the antibody molecule or fragment thereof binds to a poliovirus receptor-like molecule 4 (Nectin-4).

5. The antibody molecule or fragment thereof according to claim 4, wherein the antibody molecule or fragment thereof binds to human or cyno Nectin-4.

6. The antibody molecule or fragment thereof according to claim 1, wherein the antibody molecule is a murine antibody, a chimeric antibody or a fully or partially humanized antibody; and, the fragment is a single-chain variable fragment (scFv), disulfide-stabilized Fv fragment (dsFv), (disulfide-stabilized Fv fragment)$_2$ (dsFv)$_2$, Fab fragment, Fab' fragment, F(ab')$_2$ fragment, or variable fragment (Fv) of the antibody molecule.

7. The antibody molecule or fragment thereof according to claim 1, wherein the antibody molecule is a humanized monoclonal antibody.

8. The antibody molecule or fragment thereof according to claim 7, wherein the monoclonal antibody comprises a heavy chain constant region of an IgG1 type and a light chain constant region is of a kappa type.

9. A nucleic acid molecule comprising a nucleotide sequence encoding the antibody molecule or fragment thereof according to claim 1.

10. A vector comprising the nucleic acid molecule according to claim 9.

11. A host cell comprising the nucleic acid molecule according to claim 9.

12. A composition comprising the antibody molecule or fragment thereof according to claim 1.

13. The composition according to claim 12, wherein the composition is a pharmaceutical composition comprising a pharmaceutically acceptable carrier, adjuvant, or excipient.

14. A method for detecting or diagnosing a tumor or cancer, comprising contacting the antibody molecule or fragment thereof according to claim 1 with a sample from a subject.

15. A method for manufacturing an antibody-drug conjugate comprising conjugating the antibody molecule or fragment thereof according to claim 1 to a cytotoxic moiety.

16. An antibody-drug conjugate formed by conjugating an antibody molecule or fragment thereof according to claim 1 to a cytotoxic moiety.

17. The antibody-drug conjugate according to claim 16, wherein the cytotoxic moiety is a tubulin inhibitor, a topoisomerase inhibitor, or a DNA binding agent.

18. The antibody-drug conjugate according to claim 17, wherein the tubulin inhibitor is selected from the group consisting of Maytansinoids, Monomethyl auristatin E (MMAE), Monomethyl auristatin F (MMAF), Monomethyl Dolastatin 10, Tubulysin and its derivatives, Cryptophycin and its derivatives, and Taltobulin;

the topoisomerase inhibitor is selected from the group consisting of PNU-159682, the metabolite of doxorubicin and its derivatives, and SN38, the metabolite of irinotecan (CPT-11) and its derivatives; and the DNA binding agent is selected from the group consisting of PBD and its derivatives and Duocarmycine and its derivatives.

19. A method for treating a tumor or cancer, comprising administering to a subject in need thereof the antibody molecule or fragment thereof according to claim 1, or the antibody-drug conjugate according to claim 14.

20. The method according to claim 19, wherein the tumor or cancer is a tumor or cancer in which Nectin-4 is highly expressed.

21. The method according to claim 19, wherein the tumor or cancer is a solid tumor.

22. The method according to claim 19, wherein the tumor or cancer is bladder cancer, pancreatic cancer, breast cancer, lung cancer, gastric cancer, esophageal cancer, ovarian cancer.

23. The method according to claim 22, wherein the breast cancer is triple negative and/or basal subtypes; and the lung cancer is non-small cell lung cancer.

24. The method according to claim 19, wherein the subject is a human.

25. A kit comprising the antibody molecule or fragment thereof according to claim 1, or the antibody-drug conjugate according to claim 14.

26. The method according to claim 14, wherein the tumor or cancer is a tumor or cancer in which Nectin-4 is highly expressed.

27. The antibody molecule or fragment thereof according to claim 1, wherein the antibody molecule is a monoclonal antibody or a single chain antibody.

28. The antibody molecule or fragment thereof according to claim 1, wherein the antibody molecule or fragment thereof further comprises a constant region.

29. The antibody molecule or fragment thereof according to claim 1, wherein the antibody molecule or fragment thereof further comprises a murine or human heavy chain constant region (CH) and/or a light chain constant region (CL).

30. The antibody molecule or fragment thereof according to claim 1, wherein the antibody molecule or fragment thereof comprises a heavy chain and a light chain.

31. The antibody molecule or fragment thereof according to claim 1, wherein the antibody molecule or fragment thereof comprises a heavy chain constant region of an IgG, IgA, IgM, IgD, or IgE and/or a light chain constant region of a kappa or lambda type.

* * * * *